US012788114B2

(12) United States Patent
Converse et al.

(10) Patent No.: US 12,788,114 B2
(45) Date of Patent: Nov. 10, 2026

(54) CLOSURE DEVICES INCLUDING INCREMENTAL RELEASE MECHANISMS AND METHODS THEREFOR

(71) Applicant: BOA Technology, Inc., Denver, CO (US)

(72) Inventors: Christopher Converse, Boulder, CO (US); Eric Irwin, Denver, CO (US); Randon Kruse, Denver, CO (US); Mark Soderberg, Conifer, CO (US); Aaron Venturini, Littleton, CO (US)

(73) Assignee: BOA Technology Inc., Denver, CO (US)

( * ) Notice: Subject to any disclaimer, the term of this patent is extended or adjusted under 35 U.S.C. 154(b) by 0 days.

(21) Appl. No.: 18/335,381

(22) Filed: Jun. 15, 2023

(65) Prior Publication Data

US 2024/0074541 A1 Mar. 7, 2024

Related U.S. Application Data

(63) Continuation of application No. 17/197,668, filed on Mar. 10, 2021, now Pat. No. 11,717,056, which is a (Continued)

(51) Int. Cl.
*A43C 11/16* (2006.01)
*A43B 3/38* (2022.01)

(Continued)

(52) U.S. Cl.
CPC .............. *A43C 11/165* (2013.01); *A43B 3/38* (2022.01); *A43C 3/00* (2013.01); *A43C 11/00* (2013.01);

(Continued)

(58) Field of Classification Search
CPC ............. Y10T 24/3724; Y10T 24/2183; Y10T 24/2483; A43C 11/165; A43C 11/008; A43C 11/00
See application file for complete search history.

(56) References Cited

U.S. PATENT DOCUMENTS 3,743,280 A * 7/1973 Martinez ................ A63B 21/28 273/109
7,516,914 B2 * 4/2009 Kovacevich ......... A43C 11/165 242/395

(Continued)

*Primary Examiner* — Jason W San
*Assistant Examiner* — Michael S Lee
(74) *Attorney, Agent, or Firm* — Kilpatrick Townsend & Stockton LLP; Clark F. Weight

(57) ABSTRACT

According to an embodiment, a device for tightening an article includes a housing, a spool rotatably positioned within the housing, a knob operably coupled with the spool to cause the spool to rotate within the housing, and a stop mechanism. The device is configured so that incremental rotation of the knob in a first direction causes a corresponding incremental rotation of the spool within the housing that incrementally tensions a tension member and thereby tightens the article. The device is also configured so that incremental rotation of the knob in a second direction causes a corresponding incremental rotation of the spool that incrementally loosens the tension member's tension. The stop mechanism is configured to prevent rotation of the spool in the second direction when the tension member's tension achieves or falls below a tension threshold.

20 Claims, 32 Drawing Sheets

Related U.S. Application Data continuation of application No. 16/367,029, filed on Mar. 27, 2019, now Pat. No. 10,959,492, which is a continuation of application No. 15/478,091, filed on Apr. 3, 2017, now Pat. No. 10,251,451, which is a continuation-in-part of application No. 14/328,521, filed on Jul. 10, 2014, now Pat. No. 9,706,814, and a continuation-in-part of application No. 14/198,419, filed on Mar. 5, 2014, now Pat. No. 9,610,185.

(60) Provisional application No. 61/869,377, filed on Aug. 23, 2013, provisional application No. 61/844,788, filed on Jul. 10, 2013, provisional application No. 61/772,935, filed on Mar. 5, 2013.

(51) Int. Cl.

| | |
|---|---|
| ***A43C 3/00*** | (2006.01) |
| ***A43C 11/00*** | (2006.01) |
| ***A43C 11/12*** | (2006.01) |
| ***A43C 11/14*** | (2006.01) |
| ***A61C 7/02*** | (2006.01) |
| ***A61F 5/01*** | (2006.01) |
| ***A61F 5/02*** | (2006.01) |
| ***F16G 11/12*** | (2006.01) |

(52) U.S. Cl.

CPC .......... *A43C 11/12* (2013.01); *A43C 11/1406* (2013.01); *A61C 7/026* (2013.01); *A61F 5/0104* (2013.01); *A61F 5/0118* (2013.01); *A61F 5/0123* (2013.01); *A61F 5/028* (2013.01); *F16G 11/12* (2013.01); *Y10T 24/2183* (2015.01)

(56) References Cited

U.S. PATENT DOCUMENTS

| | | | | |
|---|---|---|---|---|
| 7,694,354 | B2 * | 4/2010 | Philpott | A42B 3/08 2/416 |
| 9,101,181 | B2 | 8/2015 | Soderberg et al. | |
| 9,610,185 | B2 | 4/2017 | Capra et al. | |
| 9,743,714 | B2 | 8/2017 | Hammerslag et al. | |
| 2005/0247813 | A1 * | 11/2005 | Kovacevich | A42B 3/14 242/395 |
| 2006/0015988 | A1 * | 1/2006 | Philpott | A42B 3/14 2/410 |
| 2007/0006489 | A1 | 1/2007 | Case, Jr. et al. | |
| 2008/0066272 | A1 | 3/2008 | Hammerslag et al. | |
| 2009/0172928 | A1 * | 7/2009 | Messmer | A43C 7/00 242/407.1 |
| 2009/0272007 | A1 | 11/2009 | Beers et al. | |
| 2010/0139057 | A1 * | 6/2010 | Soderberg | B65H 75/4434 242/396.2 |
| 2011/0167543 | A1 * | 7/2011 | Kovacevich | F16G 11/12 2/417 |
| 2011/0266384 | A1 * | 11/2011 | Goodman | B65H 75/4431 29/434 |
| 2013/0092780 | A1 | 4/2013 | Soderberg et al. | |
| 2013/0345612 | A1 | 12/2013 | Bannister et al. | |
| 2014/0359981 | A1 | 12/2014 | Cotterman et al. | |
| 2015/0076272 | A1 * | 3/2015 | Trudel | A43C 7/00 242/381.4 |
| 2015/0313319 | A1 | 11/2015 | Ha | |

* cited by examiner

CLOSURE DEVICES INCLUDING INCREMENTAL RELEASE MECHANISMS AND METHODS THEREFOR

CROSS-REFERENCES TO RELATED APPLICATIONS

This application is a continuation of U.S. patent application Ser. No. 17/197,688 by Converse et al., entitled "CLOSURE DEVICES INCLUDING INCREMENTAL RELEASE MECHANISMS AND METHODS THEREFOR," filed Mar. 10, 2021, which is a continuation of U.S. patent application Ser. No. 16/367,029 by Converse et al., entitled "CLOSURE DEVICES INCLUDING INCREMENTAL RELEASE MECHANISMS AND METHODS THEREFOR," filed Mar. 27, 2019, now issued U.S. Pat. No. 10,959,492, which is a continuation of U.S. patent application Ser. No. 15/478,091 by Converse et al., entitled "CLOSURE DEVICES INCLUDING INCREMENTAL RELEASE MECHANISMS AND METHODS THEREFOR," filed Apr. 3, 2017, now issued U.S. Pat. No. 10,251,451, which is a continuation-in-part of U.S. application Ser. No. 14/328,521 by Converse et al., entitled "CLOSURE DEVICES INCLUDING INCREMENTAL RELEASE MECHANISMS AND METHODS THEREFOR," filed Jul. 10, 2014, now issued U.S. Pat. No. 9,706,814, which claims priority to U.S. Patent Application No. 61/844,788 by Converse et al., entitled "INCREMENTAL RELEASING DEVICES AND METHODS FOR APPAREL CLOSURE DEVICES," filed Jul. 10, 2013, and to U.S. Patent Application No. 61/869,377 by Converse et al., entitled "INCREMENTAL RELEASING DEVICES AND METHODS FOR APPAREL CLOSURE DEVICES," filed Aug. 23, 2013. U.S. patent application Ser. No. 15/478,091 is also a continuation-in-part of U.S. application Ser. No. 14/198,419 by Capra et al., entitled "SYSTEMS, METHODS, AND DEVICES FOR AUTOMATIC CLOSURE OF MEDICAL DEVICES," filed Mar. 5, 2014, now issued U.S. Pat. No. 9,610,185, which claims priority to U.S. Patent Application No. 61/772,935, filed Mar. 5, 2013. The entire disclosures of all aforementioned applications are hereby incorporated by reference, for all purposes, as if fully set forth herein.

BACKGROUND OF THE INVENTION

The present invention is related to closure devices for various articles, such as braces, medical devices, shoes, clothing, apparel, and the like. Such articles typically include closure devices that allow the article to be placed and closed about a body part. The closure devices are typically used to maintain or secure the article to the body part. For example, shoes are typically placed over an individual's foot and lace is tensioned and tied to close the shoe about the foot and secure the shoe to the foot. Conventional closure devices have been modified in an effort to increase the fit and/or comfort of the article about the body part. For example, shoe lacing configurations and/or patterns have been modified in an attempt to increase the fit and/or comfort of wearing shoes. Conventional closure devices have also been modified in an effort to decrease the time in which an article may be closed and secured about the body part. These modifications have resulted in the use of various pull cords, straps, and tensioning devices that enable the article to be quickly closed and secured to the foot.

BRIEF SUMMARY OF THE INVENTION

The embodiments described herein provide closure systems that may be used to increase and loosen a tension member's tension and thereby adjust the tightness of an article. The closure systems may be used to adjust the tightness of a variety of articles, such as shoes, braces, apparel, sporting equipment, and the like. In some embodiments, the closure system may have a component or mechanism that functions to limit the amount of loosening of the tension member. The component or mechanism may limit the amount of loosening of the tension member by restricting or preventing the transfer of input rotational forces to one or more internal system components. In some embodiments, the component or mechanism may transition between an engaged state and a disengaged state to either enable or disable the transfer of the input rotational forces to the internal system components.

According to one aspect, a reel for use with a lacing system for tightening an article includes a housing having an interior region and a spool positioned within the interior region of the housing and rotatable relative thereto. The spool includes an annular channel formed therein. A knob that is rotatable relative to the housing is operably coupled with the spool to cause the spool to rotate within the interior region of the housing. Incremental rotation of the knob in a first direction relative to the housing causes a corresponding incremental rotation of the spool within the interior region of the housing that incrementally gathers a tension member in the annular channel formed in the spool. Similarly, incremental rotation of the knob in a second direction relative to the housing causes a corresponding incremental rotation of the spool that incrementally releases the tension member from the annular channel formed in the spool. The reel also includes a stop mechanism that is configured to prevent rotation of the spool in the second direction when a tension of the lace achieves or decreases beyond a tension threshold.

According to another aspect, a closure system for tightening an article includes a housing having an interior region, a tensioning mechanism that is configured to tension a tension member and thereby tighten the article, a first mechanism that is transitionable between an engaged state and a disengaged state, and a second mechanism that is transitionable between an engaged state and a disengaged state. When in the engaged state, the first mechanism allows the tension member to be incrementally tensioned via a first operation of the tensioning mechanism while preventing loosening of the tension member's tension. When in the disengaged state, the first mechanism allow the tension member's tension to be incrementally loosened via a second operation of the tensioning mechanism. When in the disengaged state, the second mechanism allows the tension member's tension to be incrementally tensioned via the first operation of the tensioning mechanism and to be incrementally loosened via the second operation of the tensioning mechanism. When in the engaged state, the second mechanism prevents the tension member's tension from being incrementally loosened via the second operation of the tensioning mechanism. The second mechanism is transitionable from the disengaged state to the engaged state when the tension member's tension achieves or decreases beyond a tension threshold.

According to another aspect, a method for configuring a reel for use with a lacing system for tightening an article includes providing a housing having an interior region and positioning a spool within the interior region of the housing so that the spool is rotatable relative to the housing. The spool may have an annular channel formed therein. The method also includes operably coupling a knob with the spool to cause the spool to rotate within the interior region of the housing upon rotation of the knob, the knob being rotatable relative to the housing. Incremental rotation of the knob in a first direction causes a corresponding incremental rotation of the spool within the interior region of the housing that winds or gathers a tension member about the spool (e.g., incrementally gathers the tension member in an annular channel formed in the spool) and incremental rotation of the knob in a second direction causes a corresponding incremental rotation of the spool that incrementally releases the tension member from about the spool (e.g., incrementally releases the tension member from the annular channel formed in the spool). The method further includes configuring the reel with a stop mechanism that is configured to prevent rotation of the spool in the second direction when a tension of the lace achieves or decreases beyond a tension threshold.

According to another aspect, a closure system for tightening an article includes a housing having an interior region, a spool positioned within the interior region and rotatable relative thereto, a tension member coupled with the spool, a tensioning mechanism having a knob, an incremental release component operationally coupled with the spool, and a full release mechanism that is transitionable between an engaged state and a disengaged state. The tensioning mechanism is configured to effect tensioning of the tension member by winding the tension member around the spool upon rotation of the knob. The incremental release component includes one or more axially oriented teeth that engage with corresponding teeth of a toothed disc. The incremental release component is configured to effect incremental tensioning of the tension member upon rotation of the knob in a first direction by engaging the axially oriented teeth and to effect incremental loosening of the tension member's tension upon rotation of the knob in a second direction by disengaging the axially oriented teeth. Engagement of the axially oriented teeth allows the spool to rotate in a first direction while preventing rotation of the spool in a second direction and disengagement of the axially oriented teeth allows the spool to rotate in a second direction by an incremental amount. When the full release mechanism is in the engaged state, the tension member's tension may be incrementally tensioned or loosened upon said rotation of the knob and when the full release mechanism is in the disengaged state, the tension member's tension is automatically loosened.

According to another aspect, a closure system for tightening an article includes a housing having an interior region and a spool positioned within the interior region and rotatable relative thereto. A tension member is coupled with the spool. The closure system also includes a tensioning mechanism that is configured to rotate the spool within the interior region and thereby tension the tension member to tighten the article. The closure system further includes a tension release mechanism that is configured to allow the spool to be rotated in a first direction via a first operation of the tensioning mechanism to incrementally tension the tension member and to allow the spool to be rotated in a second direction via a second operation of the tensioning mechanism such that the tension member's tension is loosened in substantially infinitely small increments. In some embodiments, the closure system additionally includes a full release mechanism that is transitionable between an engaged state and a disengaged state. When in the engaged state, the full release mechanism allows the tension member's tension to be tensioned and loosened via said operation of the tensioning mechanism, and when in the disengaged state, the full release mechanism allows the tension member's tension to be automatically loosened.

BRIEF DESCRIPTION OF THE DRAWINGS

The present invention is described in conjunction with the appended figures.

Figure 1:
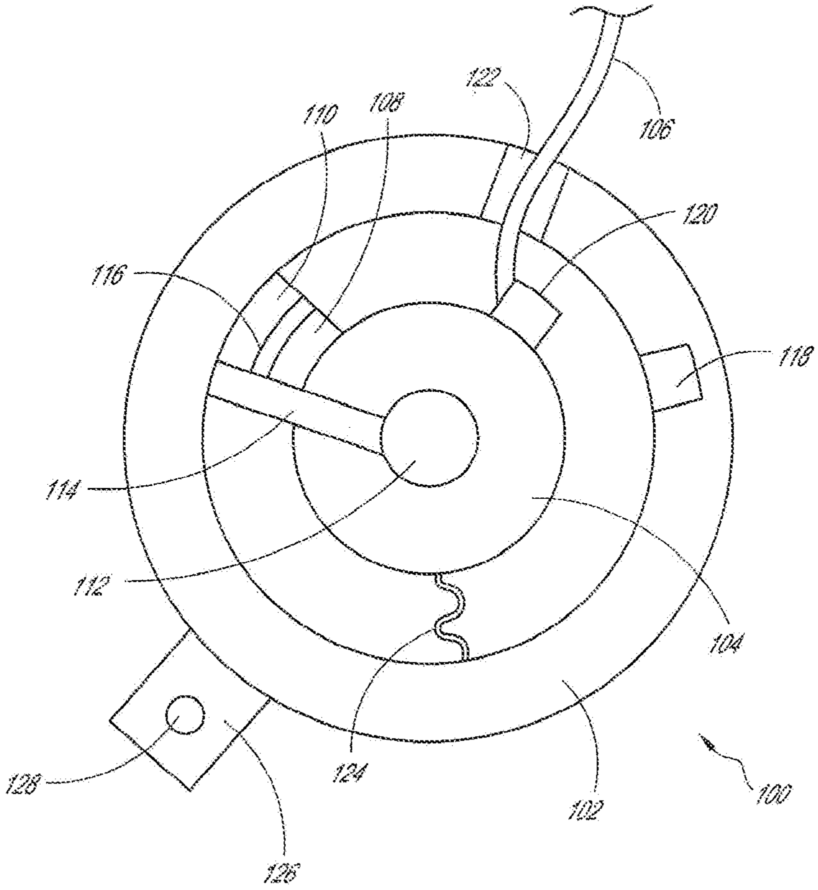
FIGS. 1-3 illustrate an embodiment of a reel based closure system and various components that may be included within the reel based closure system.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION OF THE INVENTION

Embodiments described herein provide various mechanisms that may be used to "incrementally" loosen or release tension on a tension member that is tensioned to close and/or tighten a variety of items, such as medical braces (back braces, knee braces, and the like), items of clothing (hats, gloves, and the like), sports apparel (boots, snowboard boots, ski boots, and the like), footwear (running shoes, cycling shoes, athletic shoes, outdoor shoes, and the like) and various other items. Such articles are commonly tensioned with a lace or cord that is positioned and/or guided about the article via one or more guides. For ease in describing the embodiments herein, the tension member will be generally referred to as a lace, although it should be realized that virtually any component that is capable of being tensioned may function as the tension member. As described herein, the guides that are used to position and/or guide the lace about the article may have a lumen, channel, or other recess within which the lace is positioned.

As used herein incrementally releasing lace tension means that the tension of or applied to the lace is loosened or otherwise adjusted gradually and often by regular degrees, increments, amounts, or steps. For example, in some embodiments the lace tension may be loosened or otherwise adjusted by discrete steps or amounts. In other embodiments, the lace tension may be loosed by infinitely small increments, steps, or amounts. The description of loosening the lace by infinitely small increments or amounts means that the loosening does not necessarily involve and/or is not achieved in discrete segments or steps. Rather, the lace is capable of being loosened by very minor, and sometimes nearly indistinguishable or insubstantial, amounts. In such embodiments, the lace is also capable of being loosened by a significant or substantial amount. The ability to both loosen the lace by infinitely small amounts or substantial amounts allows the user to quickly achieve a lace tension that is comfortable and/or preferred. It also allows the user to tension the lace by essentially amount rather than by discrete increments or segments.

A specific application of the incremental lace loosening concepts described herein involves reel based closure devices and systems, where a knob or other component is rotated, or otherwise operated, to wind the lace around a spool and to unwind lace therefrom. Many conventional reel based closure devices and systems are not capable of incrementally releasing lace tension. Rather, these conventional systems often fully loosen or release lace tension upon operation of a loosening mechanism. Stated differently, these conventional systems often loosen or release lace tension in a single step, or a few steps, and the lace tension is reduced to at or near essentially zero or minimal tension.

The incremental lace loosening embodiments described herein function in a manner that is opposite to these conventional loosening technologies in that the embodiments allow the tension on the lace to be loosened or adjusted by relatively small amounts or degrees without fully releasing or loosening the tension on the lace. This incremental lace loosening capability may be beneficial when relative small or minor adjustments of lace tension are desired. For example, a user may wish to release or loosen tension on the lace of a running or cycling shoe when the user is not actively using the shoe (i.e., running or cycling) so as to provide a more comfortable fit of the shoe. In such instances, the user may easily employ the incremental lace loosening embodiments described herein to slightly loosen the lace tension as desired without fully loosening the lace. Conventional closure systems that require fully loosening the lace would require the user to fully loosen the lace and then retighten the lace using the closure system until the desired lace tension and fit of the shoe is achieved. In such instances, the user may accidentally "overshoot" or over-tension the lace, which would require fully loosening and re-tensioning of the lace, such as by pulling open the device to loosen the lace and then re-tensioning the lace. Similarly, a patient may desire to adjust the lace tension of a brace by some small amount to provide a more comfortable fit and/or to account for swelling of a limb. The embodiments described herein allow the lace tension to be loosened or adjusted without requiring the lace to be fully loosened.

In some embodiments it may be desired to limit the amount of loosening that may be performed. For example, in embodiments that involve a reel based closure system, it may be desired to restrict or prevent loosening of the lace after the lace achieves or decreases beyond a tension threshold. Preventing further lace tension loosening may prevent a patient from removing a brace or medical device that is fit about a limb and/or prevent damage to the lace and/or internal components of the reel based closure system. For example, if the lace is fully loosened so that the tension is essentially zero, further rotation of the knob component in a loosening direction may cause the lace to "backwind" around the system's spool. Stated differently, too much rotation of the knob component in the loosening direction will cause the lace to be wound around the spool in a direction opposite that for which it was designed. Back winding of the lace may cause the lace to kink, tangle, twist, loop, and/or cause other problems that may compromise the integrity of the lace and/or closure system. Back winding may also damage other internal components of the closure system. The embodiments described herein restrict or prevent such undesired lace tension loosening. In some embodiments, the closure device may include one or more components or mechanisms that automatically restrict or prevent lace tension loosening after the lace achieves or decreases below a tension threshold. The components or mechanisms may automatically transition from one state to another to allow lace tension loosening when the lace tension is above the tension threshold and to prevent further loosening when the tension falls below the tension threshold.

Some embodiments also allow the lace to be fully loosened, such as by pulling axially upward on a knob component of the device, or by rotating the knob component in a loosening direction (e.g., ¼ turn), to loosen the lace and subsequently pushing axially downward on the knob component, or rotating the knob component in a tightening direction, to reengage the device and tension the lace. Accordingly, some embodiments allow both an incremental and full lace loosening approach. The full lace loosening embodiments allow the lace tension to be quickly loosened or released, which may be important when speed or time is important, such as sporting events that require a relatively quick change of footwear. Further, the embodiments that provide both incremental and full lace loosening capabilities provide the user with a unique combination of lace loosening speed and convenience in fine or minor lace tension adjustment.

A specific embodiment in which the incremental lace loosening mechanisms or devices may be used involves shoes. For ease in describing the embodiments herein, the disclosure will mainly describe the incremental lace loosening mechanisms/device being used for shoes, although it should be realized that the closure devices may be used for the various other items.

Figure 2:
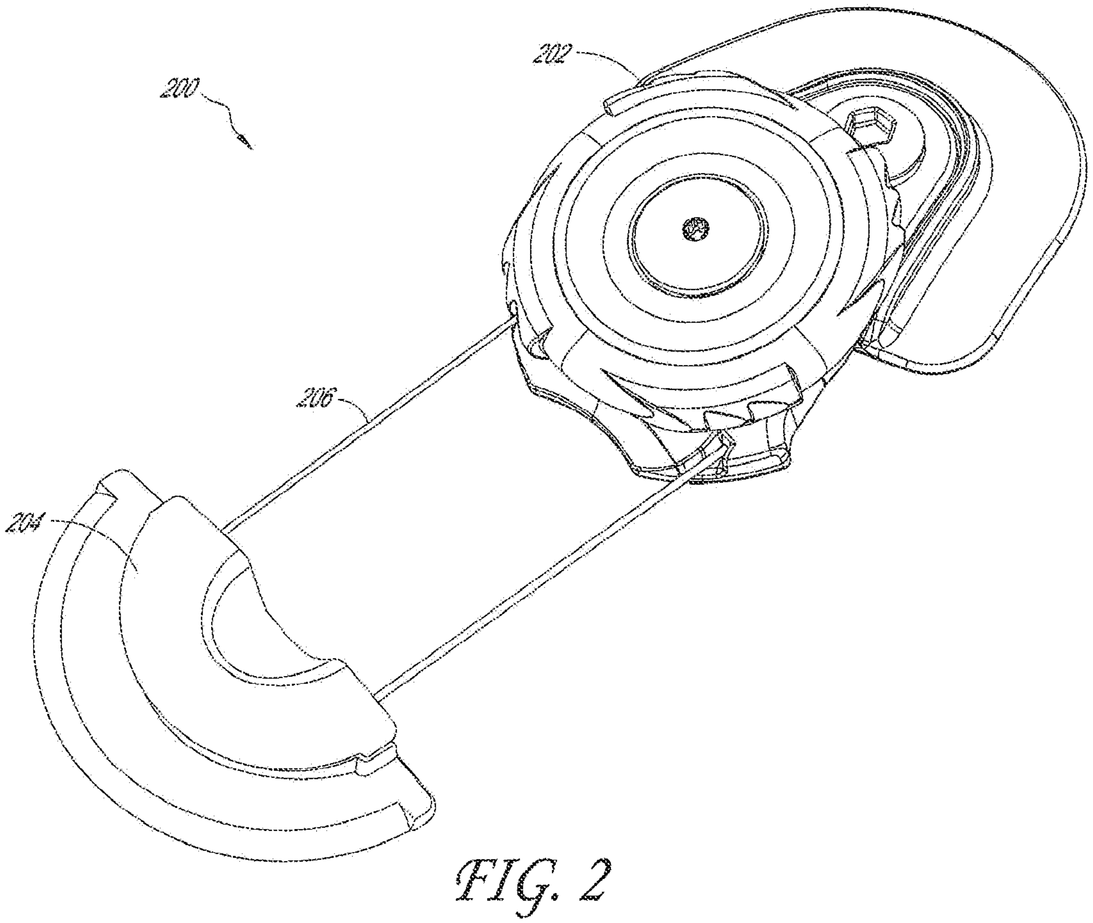
Figure 3:
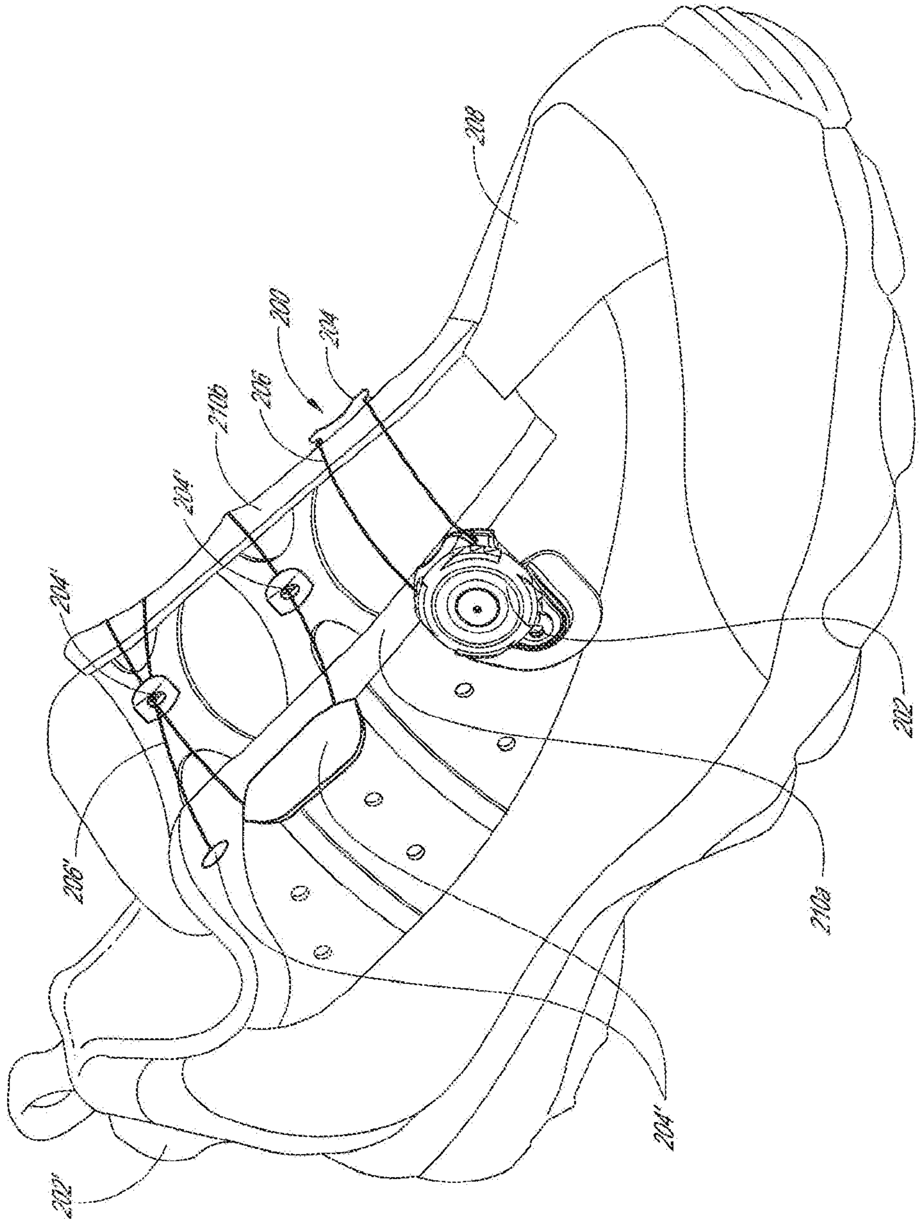

Referring now to FIGS. 1-3, illustrated is an embodiment of a reel based closure system. FIGS. 1-3 provide a general overview of the various components that may be included within a reel based closure system or device. The other embodiments described herein may include one or more of the components described and illustrated in FIGS. 1-3, but do not necessarily need to contain said components. FIG. 1 schematically illustrates an example embodiment of a reel assembly 100 for use with a closure device or system. The reel assembly 100 includes a housing 102, and a spool 104 that rotates relative to housing 102 to adjust tension on a lace 106. The spool 104 can be coupled to a first engagement member 108 and the housing 102 can be coupled to a second engagement member 110. The first and second engagement members 108, 110 can interface with each other to limit or otherwise influence the rotation of the spool 104 relative to the housing 102. For example, the engagement members 108, 110 can allow the spool 104 to rotate substantially unimpeded in a first direction so as to gather lace 106 into the reel assembly 100, and the engagement members 108, 110, when engaged with each other, can prevent the spool 104 from rotating in a second direction that releases lace 106 from the reel assembly 100. In some embodiments, the first engagement member 108 can include one or more pawls, and the second engagement member 110 can include a plurality of teeth.

The reel assembly 100 can include a knob 112 that can be configured to control rotation of the spool 104. For example, rotating the knob 112 in a first direction can cause the spool 104 to rotate in the first direction, thereby gathering lace into the reel assembly 100. Engagement members 108, 110 can incrementally lock the spool 104 against rotation in the second direction. In some embodiments, rotating the knob 112 in a second direction can cause the engagement members 108, 110 to disengage from each other to allow the spool 104 to rotate in the second direction, thereby releasing lace 106 from the reel assembly 100. In some embodiments, the engagement members 108, 110 can be configured to reengage after the spool 104 has rotated a predetermined amount in the second direction, thereby locking the spool 104 against further loosening until the knob 112 is again rotated in the second direction. In this manner, reel assembly 100 can provide for incremental release of the lace 106 from the reel assembly 100. In some embodiments, the reel 112 can include one or more drive members 114, which can be integral to, or coupled to, the knob 112, and which can interface with the spool 104, the first engagement member 108, and/or the second engagement member 110 to control rotation of the spool 104. In some embodiments, a protection element 116 can be provided to increase the durability of one or both of the engagement members 108, 110. For example, the protection element 116 can be a metal (or other suitably durable) cap that is placed on the portion of a pawl that interfaces with the teeth.

In some embodiments, the reel assembly 100 can include a debris diverter that can be configured to move debris away from the interface between the engagement members 108, 110. In some embodiments, the reel assembly 100 can include a lace retaining element 120 that can be configured to retain the lace 106 away from the walls of the housing 102 to prevent the lace 106 from backing up inside the reel assembly 100. In some embodiments, if the lace 106 is loosened when no tension is placed on the lace 106, the lace 106 can tend to unwind inside the reel assembly 100 and move radially outward away from the rotational axis of the spool 104. If the lace 106 moves radially outward and contacts the inner wall of the housing 102, friction between the housing 102 and the lace 106 can cause the lace to double back on itself inside the reel assembly 100. In some embodiments, the lace retaining element 120 can be configured to hold the lace 106 off of the housing 102 wall as the lace 106 is loosened, thereby facilitating the exiting of the lace 106 through hole 122 during loosening. In some embodiments, the reel assembly 100 can include a lace termination pocket 118 that provides a termination point for the lace.

In some embodiments, the reel assembly 100 can include a rotation limiter 124. The rotation limiter can be configured to prevent the spool 104 from being rotated too far in the first direction and/or in the second direction. If excessive lace 106 is drawn into the reel assembly 100, the lace 106 can jam the reel assembly 100. If the spool 104 is rotated in the second direction when the lace 106 is fully loosened, the reel assembly 100 can start to start to gather lace 106 in the wrong direction. The rotation limiter can be, for example, a stop cord that is coupled to the housing 102 and to the spool 104 such that rotation of the spool 104 takes up slack in the stop cord (e.g., by winding the stop cord around a channel on the spool 104 or around a pin or other structure of the housing 102). When the stop cord becomes tight, the spool 104 is prevented from further rotation.

The reel assembly 100 can include a mounting member 126. In some embodiments, the mounting member 126 can be a flange that is configured to be sewn, adhered, or otherwise coupled to an article (e.g., a shoe). In some embodiments, the mounting member 126 can be configured to removably attach to a base member (not shown) on the article so that the reel assembly 100 can be removed from the article, such as for repair or replacement of the reel assembly 100. The mounting member 126 can include a hole 128 that receives a fastener (e.g., a bolt) that secures the mounting member 126 to the base member on the article.

Although the embodiments described herein may be described as having various features integrated into a single reel assembly (e.g., the incremental release, protection element 116, debris diverter, lace retaining element 120, rotation limiter 124, and removable mounting member 126 of the reel assembly 100 of FIG. 1), other embodiments can be made to use only one of the described features, or any combination of the described features. Also, additional features can be incorporated into the reels described herein in addition to the features specifically described.

FIG. 2 is a perspective view of an example embodiment of a closure device or system 200. The closure system 200 can include a reel assembly 202, at least one lace guide 204, and a lace 206 that extends between the reel 202 and the lace guide 204. The reel assembly 202 can be configured to gather lace 206 to draw the lace guide 204 closer to the reel assembly 202 and tighten the closure system 200, and the reel assembly 202 can be configured to release lace 206 to loosen the closure system 200. Although only one lace guide 204 is shown in FIG. 2, any suitable number of lace guides 204 (e.g., 2, 3, 5, etc.) can be used.

In some embodiments, the lace 206 can be a highly lubricious cable or fiber having a high modulus of elasticity and a high tensile strength. In some embodiments, the cable can have multiple strands of material woven together. While any suitable lace can be used, some embodiments can utilize a lace formed from extended chain, high modulus polyethylene fibers. In some embodiments, SPECTRA' fiber (manufactured by Honeywell of Morris Township, N.J.) can be used. In some embodiments, the lace can be formed from a molded monofilament polymer. The lace or cable can have a diameter of at least about 0.02 inches and/or no more than about 0.04 inches, or at least about 0.025 inches and/or nor more than about 0.035 inches, although diameters outside these ranges can also be used. In some embodiments, the lace can have a core/sheath configuration where a first material is used for the lace core and a second material is used for a sheath that is positioned over the core. For example, SPECTRA™ or Dyneema® may be used for the lace core and polyester or another material may be used for the sheath.

The lace can be made of high modulus fibers that advantageously have a high strength to weight ratio, are cut resistant, and/or have very low elasticity. The lace can be formed of tightly woven fibers to provide added stiffness to the lace. In some embodiments, the lace can have enough column strength that the lace can be easily threaded through the lace guides, and into the reel and spool, or through the guides so as to form a loop of lace that can be easily grasped by a user. In some embodiments, the lace can have enough column strength that the lace can be pushed out of the reel without doubling back on itself, as discussed elsewhere herein.

FIG. 3 is a perspective view of the closure system 200 incorporated into a sports shoe 208. The closure system 200 can also be incorporated into any other suitable articles including, but not limited to, cycling shoes, boots, other footwear, belts, hats, gloves, braces, helmets, boot bindings, backpacks, or other suitable wearable articles, or any other item in which two portions are to be selectively drawn together and loosened. The shoe 208 can have a first side 210*a* and a second side 210*b*, and the closure system 200 can extend between the sides 210*a*, 210*b*. Thus, when the lace 206 of the closure system 200 is tightened, the sides 210*a*, 210*b* of the shoe 208 are drawn together, and when the lace 206 is loosened, the sides 210*a*, 210*b* of the shoe 208 are allowed to move apart. In the illustrated embodiment, the shoe 208 has a second reel 202' mounted to the heel portion of the shoe 208. The second reel 202' can be similar to, or the same as, the first reel 202. The second lace 206' can pass along a channel through the shoe 208 to the lace guides 204'. The second reel 202' can be configured to tighten a second lace 206' on an upper zone of the shoe 208, and the reel 202 can tighten a lower zone of the shoe 208. Many variations are possible. For example, a single reel can be used to adjust a single lace that extends through the full set of lace guides 204, 204', or more than two reels can be used. A reel assembly can be mounted onto tongue of the shoe 208, or on the side or heel (as shown in FIG. 3), or on any other suitable portion of the article.

Figure 4A:
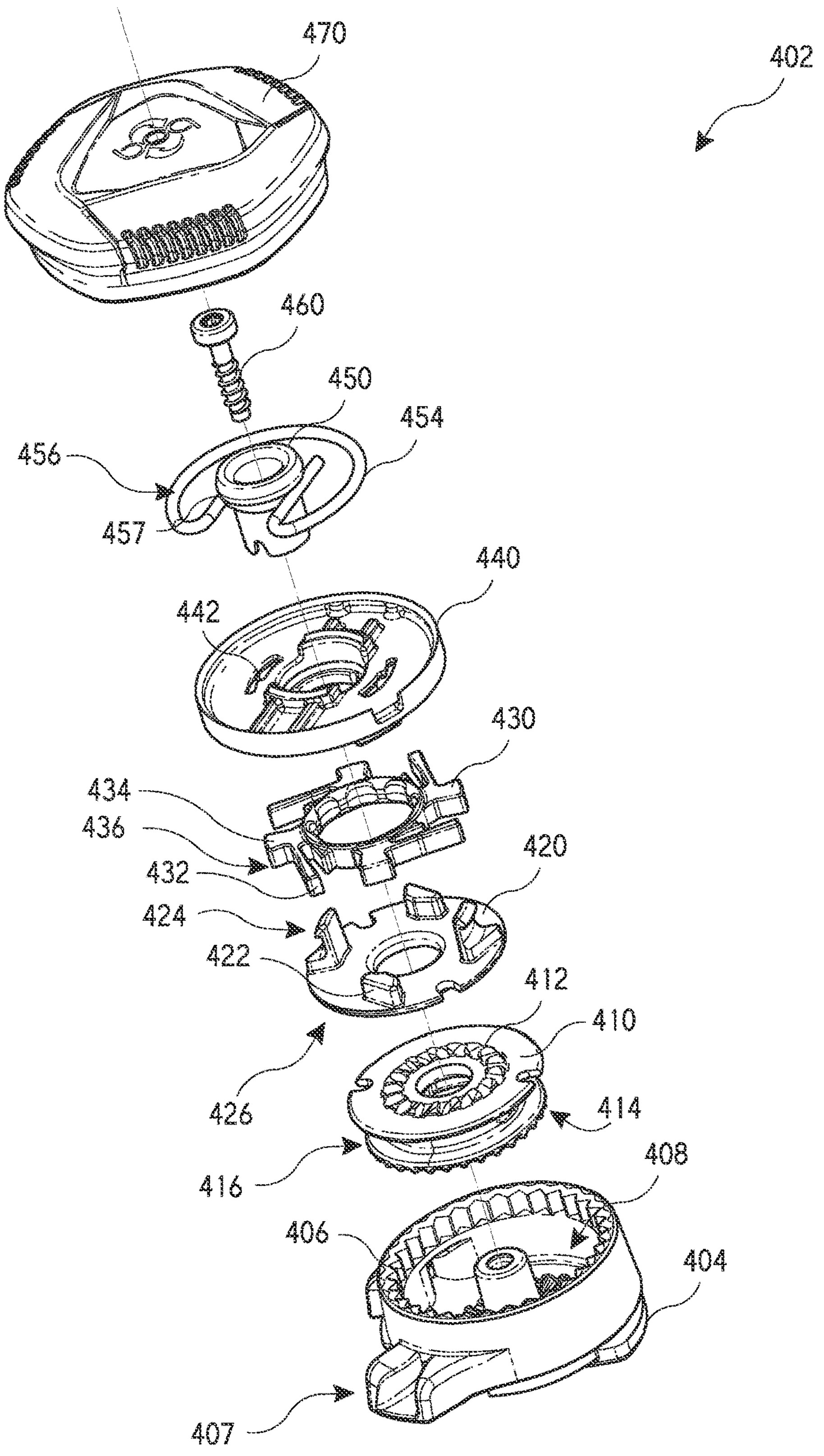
FIGS. 4A-B illustrate exploded perspective views of an embodiment of a reel assembly or reel based closure system that may be used to incrementally tighten or loosen a tension member.
Figure 4B:
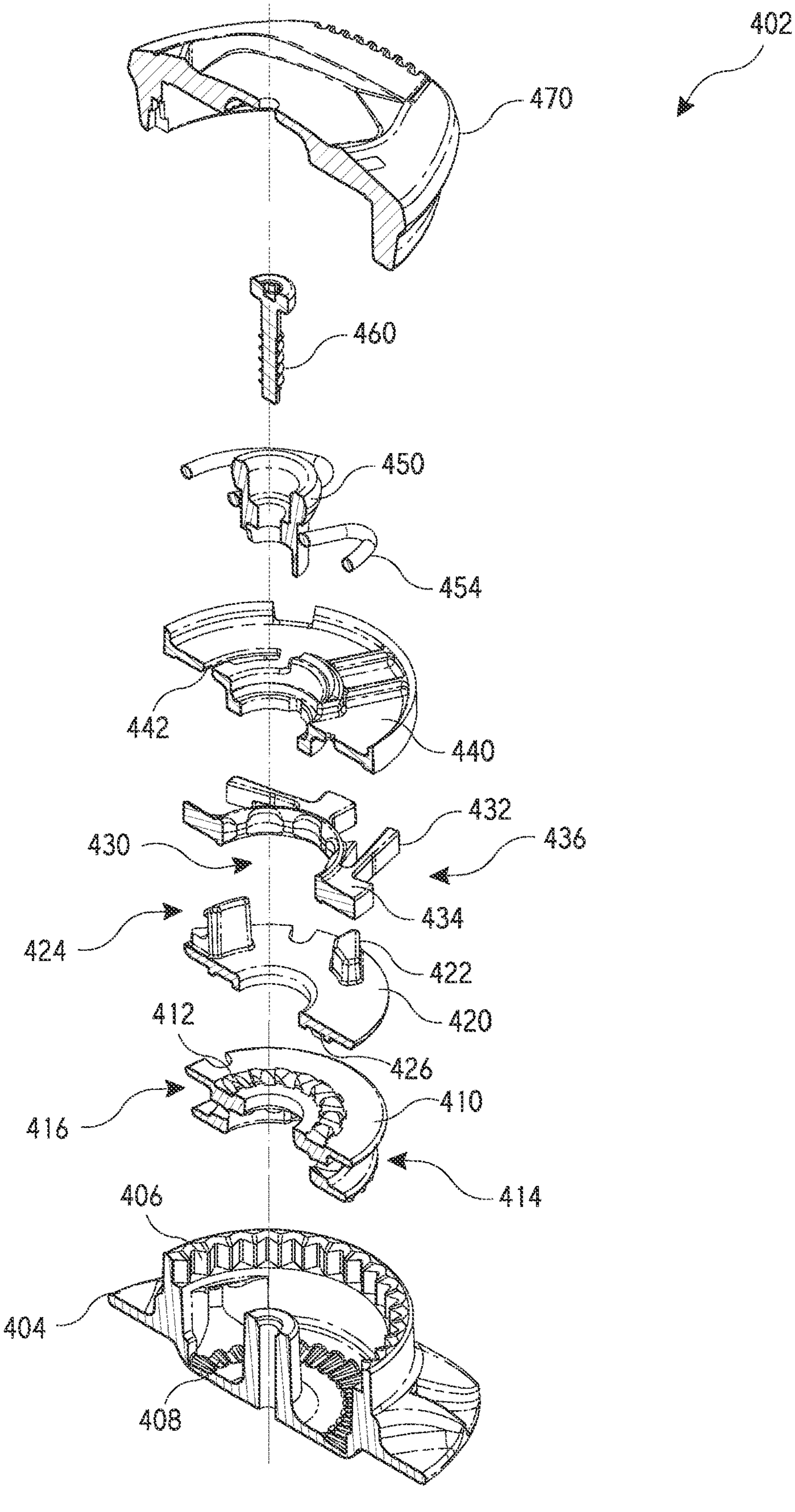

Referring now to FIGS. 4A and 4B, illustrated is an exploded perspective top view and an exploded cross-sectional perspective view, respectively, of a reel assembly 402. Reel assembly 402 includes a knob 470 that may be rotated by a user to wind lace (not shown) around a spool 410 of reel assembly 402. As knob 470 is rotated, drive members (not shown) of knob 470 rotate disc 440, which in turn rotates tension control disc 420. Tension control disc 420 is coupled with disc 440 via a pair of lipped components 424 that axially extend from a top surface of disc 420 and engage with corresponding apertures 442 of disc 440. The components 424 may snap into the apertures 442 of disc 440 to couple the two discs, 440 and 420, together with pawl disc 430 sandwich or positioned there between. Engagement of the discs, 440 and 420, via the components 424 and apertures 442 allows rotational forces input into knob 470 to be transferred from disc 440 to tension control disc 420. The disc 440 and tension control disc 420 are rotatable relative to the pawl disc 430 that is sandwiched between the two discs. This configuration allows drive components 422 of the tension control disc 420 to rotate relative to pawl disc 430 and thereby engage with components of pawl disc 430 to transfer tightening and loosening rotational forces to pawl disc 430.

Tension control disc 420 includes a plurality of drive components 422 that are used to drive and rotate pawl disc 430 in both a first direction and a second direction to tension and loosen the lace as described below. As shown in FIG. 4A, in one embodiment the tension control disc 420 may include four drive components 422 (i.e., two formed at the base of the components 424 and two independent of the components 424). The number of drive components corresponds with the number of pawl teeth 432 used and may be varied as desired between 1 and any number.

As briefly mentioned above, drive components 422 may drive, or otherwise cause rotation of, pawl disc 430 as the tension control disc 420 is rotated via disc 440 and knob 470. To drive pawl disc 430, the drive components 422 may be positioned within a space 436 between pawl teeth 432 and a drive member 434, which extends radially outward from a central core or portion of pawl disc 430. As knob 470 is rotated in a first or tightening direction (e.g., clockwise), drive components 422 contact the drive members 434 and transfer rotational forces from tension control disc 420 to pawl disc 430, which causes pawl disc 430 to rotate in the first or tightening direction. Rotation of the pawl disc 430 in the first or tightening direction causes the pawl teeth 432 to deflect radially inward and outward relative to housing teeth 406 in a ratchet like fashion. The pawl teeth 432 may be elongated members that are cantileverly mounted to, or otherwise supported by, drive members 434 and/or pawl disc 430. The cantilevered configuration of pawl teeth 432 allows the pawl teeth 432 to deflect inwardly and outwardly relative to housing teeth 406 in the ratchet like fashion.

The interaction between pawl teeth 432 and housing teeth 406 allows the pawl disc 430 to be rotated in the first or tightening direction while preventing counter rotation (e.g., counterclockwise rotation) of the pawl disc 430. The engagement of the pawl teeth 432 and housing teeth 406 also prevents rotation of other components of the reel assembly 402, such as tension control disc 420 and spool 410. For example, the engagement of the pawl teeth 432 and housing teeth 406 allows the spool 410 to be rotated in the first or tightening direction so as to wind lace (not shown) around a central channel 416 of spool 410, which tensions the lace. The interaction between pawl teeth 432 and housing teeth 406 also prevents counter rotation of the spool 410 to prevent unwinding of the lace from the central channel 416 of spool 410, and therefore prevents loosening of the lace.

The rotation of spool 410 is achieved via an interaction between teeth 412 and corresponding teeth 426 of tension control disc 420. The respective teeth, 412 and 426, of spool 410 and tension control disc 420 extend axially from the respective components in opposite directions and are configured to mate such that rotation of tension control disc 420 in the first or tightening direction causes rotation of spool 410 in the first or tightening direction. The interaction between teeth 412 and teeth 426 also prevents counter rotation of spool 410, and therefore prevents unwanted loosening of the lace.

The tension control disc 420 also enables incremental loosening of the lace when the knob 470 is rotated in a second or loosening direction (e.g., counterclockwise), which is opposite the first or tightening direction. Specifically, incremental lace tension loosening is achieved via drive components 422. Rotation of the knob 470 in the loosening direction causes tension control disc 420 to rotate in the loosening direction via disc 440 and the engagement of components 424 with apertures 442. As the tension control disc 420 rotates in the loosening direction, drive components 422 move and rotate slightly within space 436 into contact with the pawl teeth 432. A cammed, ramped, or sloped surface of drive components 422 "sweeps" or pushes the pawl teeth 432 out of engagement with the housing teeth 406. Stated differently, drive components 422 disengage the pawl teeth 432 from the housing teeth 406, which allow the pawl disc 430 and spool 410 to rotate in the loosening direction. The tension on the lace (not shown), in part, causes the spool 410 and tension control disc 420 (e.g., via teeth 412 and 426) to rotate in the loosening direction, which causes the pawl disc 430 to also rotate in the loosening direction via drive component 422. Rotation of the pawl disc 430 in the loosening direction causes the pawl teeth 432 to snap into engagement in a ratchet like fashion with housing teeth 406 that are adjacent the previously engaged housing teeth in the loosening direction. In this manner, rotation of the spool 410 in the loosening direction may be achieved in incremental or discrete steps, which allows the tension of the lace to be incrementally loosened or released.

In some embodiments, disc 440 may include protrusions on its bottom surface that function to "sweep" or push the pawl teeth 432 out of the housing teeth 406 as described above and/or drive rotation of pawl disc 430.

In some embodiments, to fully loosen or release the tension on the lace, the knob 470 may be pulled axially upward relative to housing 404 in order to disengage the pawl teeth 432 from the housing teeth 406 and thereby allow spool 410 to freely spin in the second or loosening direction. To enable the knob 470 to be pulled axially upward and disengage the pawl teeth 432 from housing teeth 406, a spring component 454 is coupled with a central bushing 450. Pulling the knob 470 axially upward causes the spring component 454 to axially move from a first annular groove or inclined face 457 of the bushing 450 to a second annular inclined face 456 of the bushing 450. In moving from the first annular inclined face 457 to the second annular inclined face 456, the spring component 454 deflects radially outward and inward. When positioned in the second annular inclined face 456, the spring component 454 holds or otherwise maintains the knob 470, disc 440, pawl disc 430, and tension control disc 420 in an axially raised position within the housing 404 wherein the pawl teeth 432 are disengaged from housing teeth 406. In the axially raised position, the teeth 426 of tension control disc 420 may also be disengaged from the teeth 412 of spool 410. In this configuration, spool 410 is able to spin or rotate freely in the loosening direction and thereby allow the lace tension to be fully loosened or released. In other embodiments, to fully loosen or release the tension on the lace, a button, lever, or other release mechanism may be pressed or operated.

The various components of reel assembly 402 may be coupled together via a fastening mechanism 460 (e.g., a bolt or screw) which is coupled with a central post of housing 404. Housing 404 may also include one or more lace channels 407 within which the lace may be threaded to access the central channel 416 of spool 410. As described above, the reel assembly 402 allows incremental releasing or loosening of lace tension as well as full or essentially complete releasing/loosening of the lace tension. Additional features of other reel assemblies are provided in U.S. patent application Ser. No. 13/273,060, filed Oct. 13, 2011, titled "Reel-Based Lacing System", the entire disclosure of which is incorporated herein by reference.

In many embodiments, it may be desirable to allow the spool 410 to be rotated in the loosening direction only as long as a minimal amount of tension exists in the lace. Stated differently, it may be desirable to prevent rotation of the spool 410 in the loosening direction when the lace tension achieves or decreases beyond a tension threshold, such as zero lace tension. Preventing further rotation of the spool 410 when the lace tension is at or near the tension threshold may prevent back winding of the lace and/or kinking or entangling of the lace within central channel 416 of spool 410. It may also prevent the lace from being "pushed" or forced out of the lace channels or ports 407.

Figure 4C:
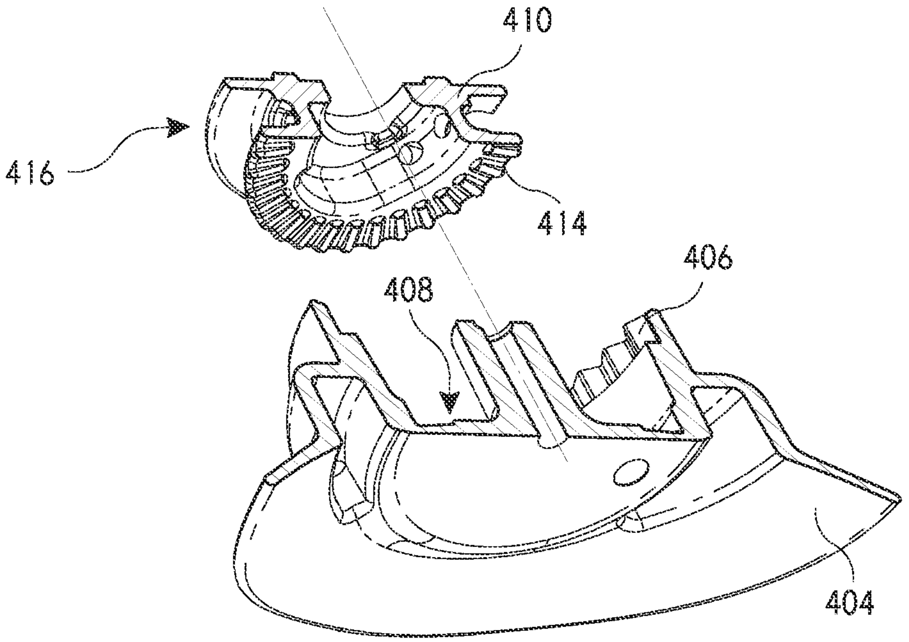
FIGS. 4C-D illustrate cross-sectional perspective views of the housing and spool of the reel assembly of FIGS. 4A-B.
Figure 4D:
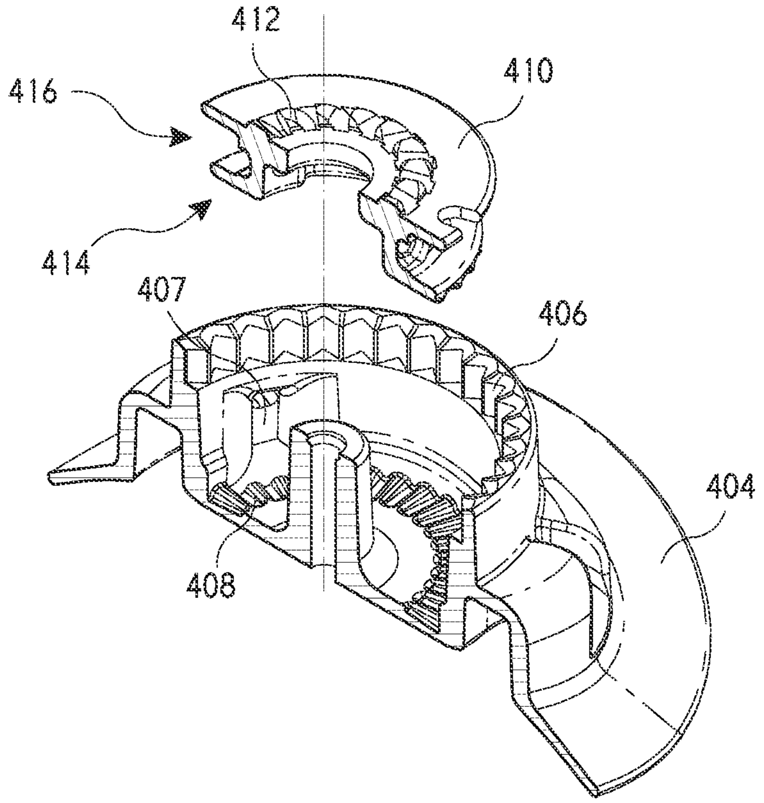

To prevent rotation of the spool 410 in the loosening direction when the lace tension is at or near the tension threshold (e.g., zero lace tension), spool 410 includes teeth 414 that are positioned on and axially extend from a bottom surface of the spool 410. The teeth 414 interact with corresponding teeth 408 that are positioned on and axially extend from an inner bottom surface of housing 404. FIGS. 4C and 4D illustrate the respective teeth, 414 and 408, of spool 410 and housing 404 in greater detail. The teeth, 414 and 408, are configured to be disengaged until the lace tension is at or near the tension threshold. Disengagement of the teeth, 414 and 408, allows the spool 410 to rotate in the tightening and loosening direction as described above to tension and loosen the lace. After the teeth, 414 and 408, engage, further rotation of the spool 410 in the loosening direction is prevented or limited. To allow engagement and disengagement of the teeth, 414 and 408, the spool 410 is configured to move axially upward and downward relative to housing 404.

In some embodiments, disengagement of the teeth, 414 and 408, may be facilitated or achieved by providing a slight taper or sloped configuration on teeth 412 and teeth 426. The taper/slope of teeth 412 and 426 may be oriented so that the spool 410 is forced or pulled axially upward relative to housing 404 and into engagement with tension control disc 420 when the tension control disc 420 rotates in the first or tightening direction and/or some amount of lace tension exists. For example, the taper/slope configuration of the teeth may cause teeth 412 of spool 410 to slide axially upward relative to and into further engagement with the teeth 426 of tension control disc 420 as the tension control disc 420 rotates in the tightening direction and/or as the lace tension is increased.

The lace tension and sloped/tapered teeth configuration may maintain the teeth 412 and 426 in the engaged configuration as the tension control disc 420 and spool 410 are rotated in the loosening direction. For example, as the tension control disc 420 rotates in the loosening direction, the tension in the lace causes the spool 410 to rotate in the loosening direction, which maintains contact and engagement between teeth 412 and teeth 426 thereby keeping the spool 410 in the axially raised position with teeth 414 and 408 disengaged. The amount of force or pressure exhibited between the teeth 412 of spool 410 and the teeth 426 of tension control disc 420 corresponds to the tension in the lace at any given time. As such, as the lace tension is loosened and nears zero, the force or pressure between the teeth 412 and 426 also decreases and nears zero, which allows the spool 410 to begin to move axially downward relative to tension control drive 420 and housing 404.

At some point, the spool 410 will move axially downward relative to housing 404 so that the teeth 414 of spool 410 engage with the teeth 408 of housing 404. Frictional engagement of the teeth, 414 and 408, prevents or limits further movement of spool 410 in the loosening direction. As the knob 470 and tension control disc 420 are rotated in the loosening direction after engagement of teeth 414 and 408, a rear surface of teeth 426 of tension control disc 420 will contact a rear surface of the teeth 412 of spool 410. The rear surfaces of teeth 426 and 412 are sloped or ramped so that contact between the rear surfaces of the teeth, 426 and 412, presses or forces the spool 410 axially downward relative to housing 404, which increases the frictional contact between teeth 414 and 408 and prevents further rotation of spool 410 in the loosening direction. The sloped the ramped configurations of teeth 426 and 412 also allows the tension control disc 420 and teeth 426 to slide axially up and over the teeth 412 and spool 410 as the tension control disc 420 is rotates in the loosening direction. In this manner, the knob 470, tension control disc 420, and the other components of reel assembly 402 (e.g., a pawl disc 430 and disc 440) may continue to be rotated in the loosening direction without causing rotation of the spool 410. In some embodiments, the knob 470 and/or other components may move slightly axially upward and downward as the tension control disc 420 slides axially up and over the spool teeth 412. In other embodiments, the knob 470 may be forced axially upward and into an open configuration when the knob 470 is rotated in the loosening direction after engagement of teeth 414 and 408. For example, the central bushing 450 may engage and lock or maintain the knob 470 in an axially upward and open configuration when the knob 470 is rotated in the loosening direction after engagement of teeth 414 and 408. As described herein, in the open configuration, the spool 410 may be allowed to freely spin within the housing 404.

In some embodiments, the teeth, 414 and/or 408, may be replaced by other frictional components, such as a rubber type gasket or material, abrasive materials, tacky materials, and the like. Even when the spool 410 is moved axially downward so that the teeth, 414 and 408, contact one another, the configuration of the teeth 426 of tension control disc 420 and the teeth 412 of spool 410 is such that rotation of the tension control disc 420 in the tightening direction causes the teeth 426 and 412 to contact one another and reengage. Stated differently, the teeth 426 of disc 420 and the teeth 412 of spool 410 are configured in an axially overlapping manner so that rotation of the knob 470 and tension control disc 420 causes the teeth 426 and 412 to contact one another as long as the knob 470 and other reel assembly components are not in the axially raised position relative to housing 404. As such, when the knob 470 is once again rotated in the tightening direction, the teeth 426 of tension control disc 420 will once again engage the teeth 412 of spool 410, which will cause the spool 410 to be forced or pulled axially upward and thereby disengage the teeth 414 and 408 of the spool 410 and housing 404, respectively. In this manner, the reel assembly 402 may be operated to re-tension the lace as previously described.

The embodiments described herein may be used to tension a variety of laces and lace patterns. For example, in some embodiments, a single "active" lace may traverse across a shoe or other article and may be tensioned by any of the incremental lace loosening closure devices described herein. The term single active lace means that a single lace is coupled with the closure device and tensioned thereby. Such laces often have a distal end that terminates on the shoe or article, or on a housing or other component of the closure device, and a proximal end that is coupled with the closure device (e.g., wound around a spool component) and tensioned by the closure device. In other embodiments, a dual active lace may traverse the shoe or other article and may be tensioned by an incremental lace loosening closure device. The term dual active lace means that two or more laces are coupled with the closure device and tensioned thereby, or that a proximal and distal end of a single lace are coupled with the closure device and tensioned thereby. The two or more laces may each have a distal end that terminates on the shoe or article, or on a housing or other component of the closure device, and a proximal end that is coupled with the closure device and tensioned thereby.

Figure 4E:
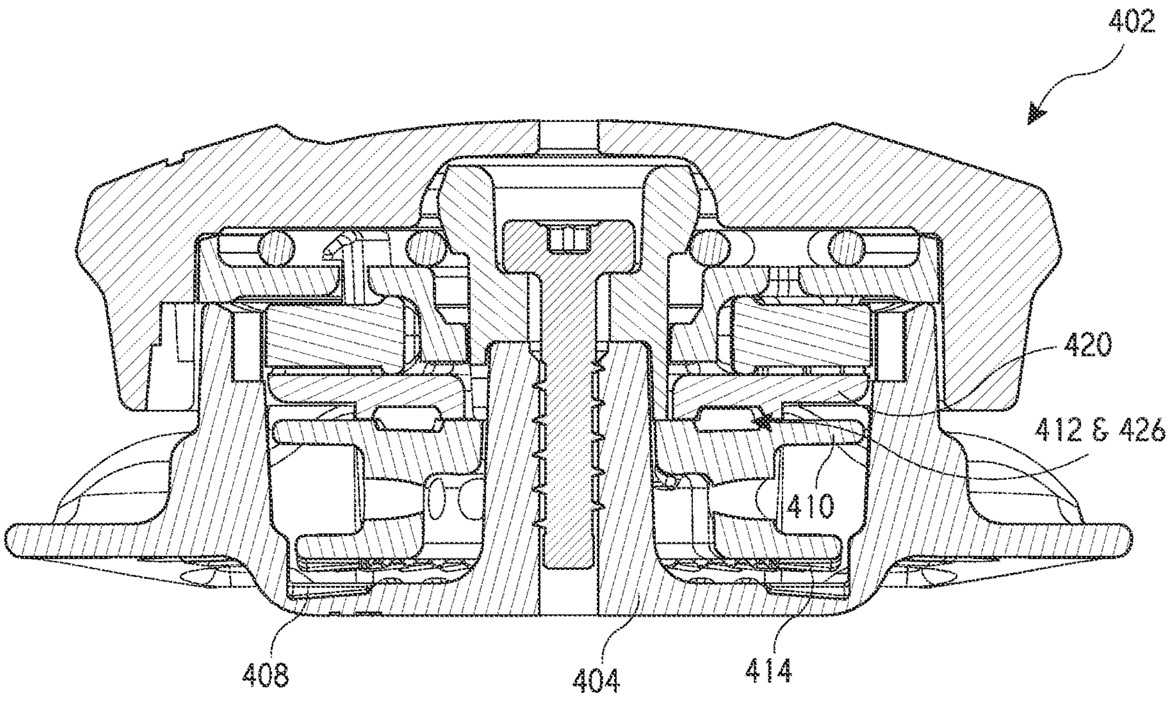
FIGS. 4E-G illustrate cross-sectional views of the assembled components of the reel assembly of FIGS. 4A-B.
Figure 4F:
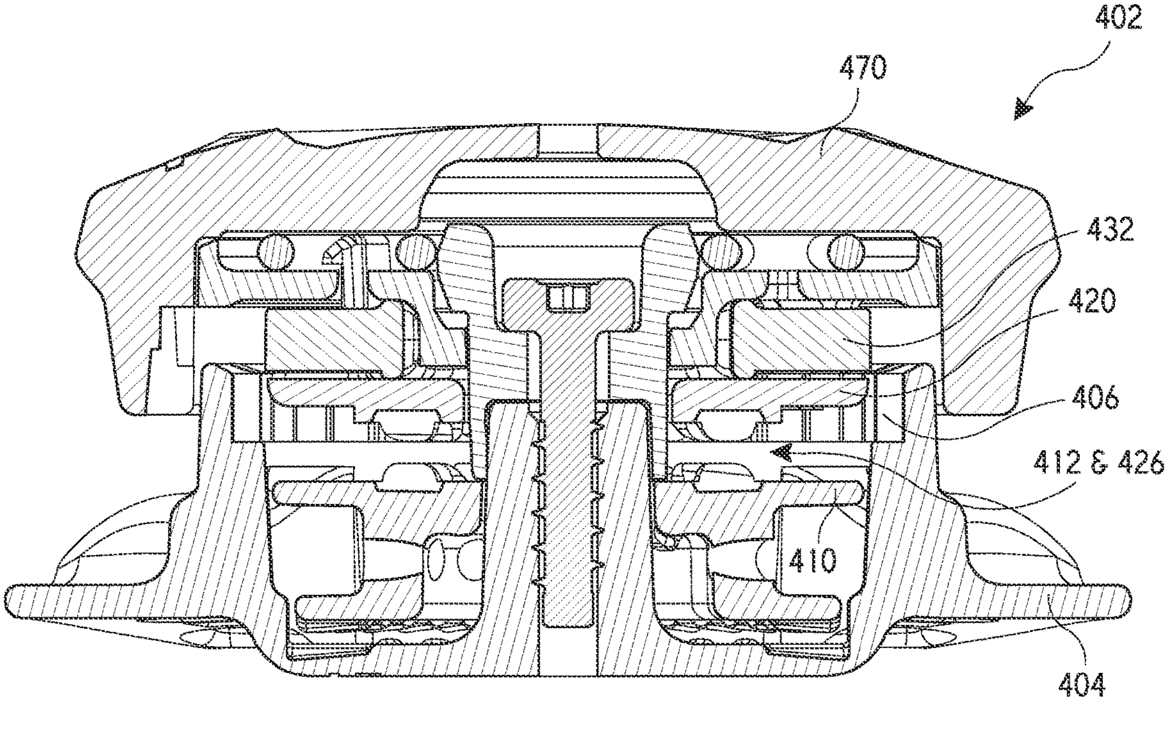
Figure 4G:
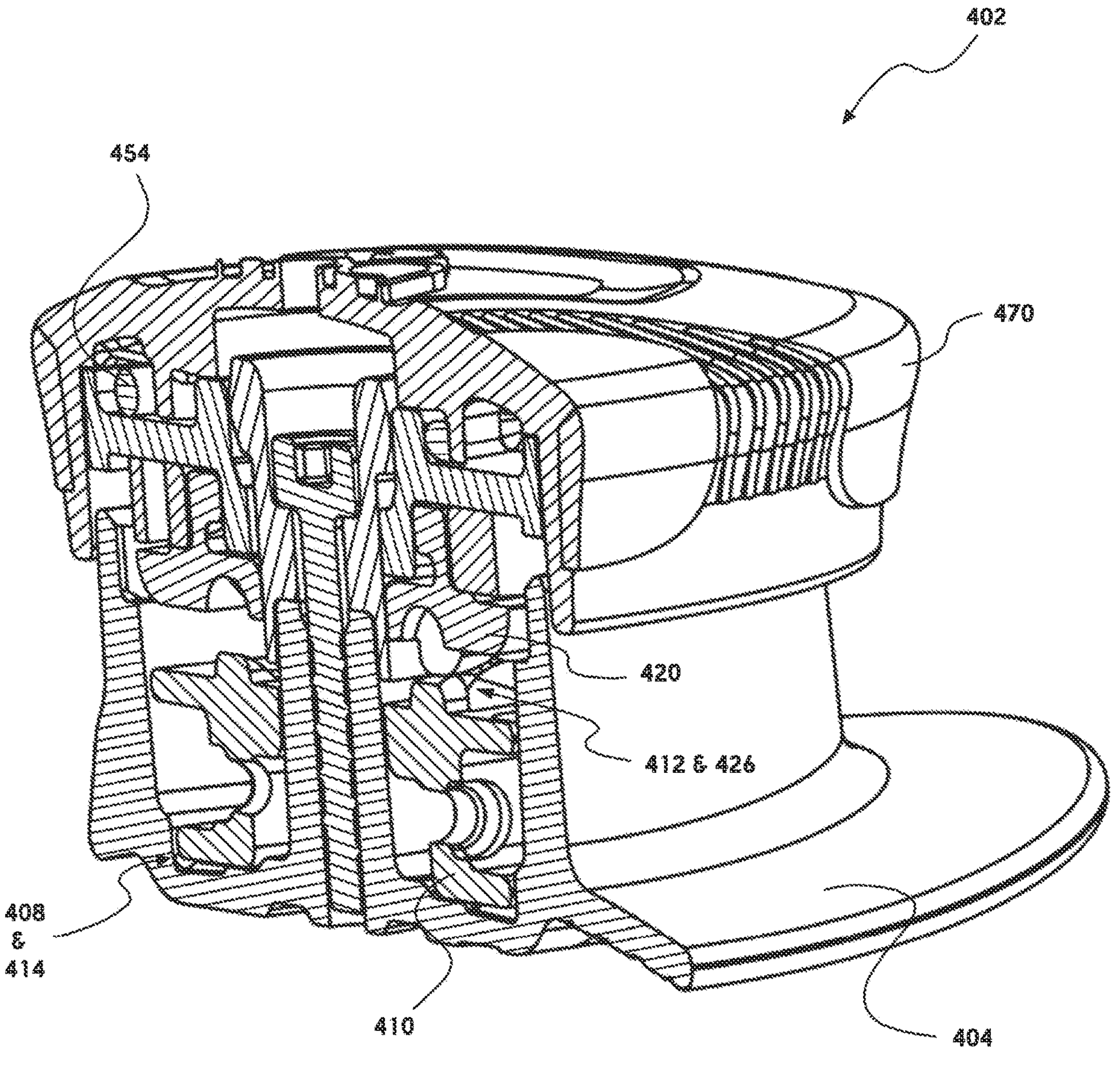

Referring now to FIGS. 4E-4G, illustrated are cross-sectional views of the reel assembly 402 in the various configurations described above. FIG. 4E illustrates the reel assembly 402 with the spool 410 fully engaged with tension control disc 420. As shown in FIG. 4E, in this configuration the teeth 414 of spool 410 are disengaged from the teeth 408 of housing 404 such that a gap exists between the teeth 408 and 414. In contrast, the teeth 426 of tension control disc 420 are fully engaged with the teeth 412 of spool 410 such that the spool 410 is pulled or forced axially upward and into full engagement with tension control disc 420. In this configuration, spool 410 is able to be rotated in both the tightening and loosening direction to incrementally tension and/or loosen lace (not shown) of reel assembly 402.

FIG. 4F illustrates the reel assembly 402 with the knob 470 and other components (i.e., pawl disc 430, tension control disc 420, and disc 440) raised axially relative to housing 404 such that pawl teeth 432 are disengaged from the housing teeth 406 and such that teeth 412 and 426 of spool 410 and tension control disc 420, respectively, are disengaged. In this configuration, the spool 410 is able to freely rotate in the loosening direction to fully release or loosen the tension of the lace of reel assembly 402.

FIG. 4G illustrates the reel assembly 402 with the teeth 408 of housing 404 fully engaged with the teeth 414 of spool 410. FIG. 4G also illustrates the back surfaces of teeth 412 and 426 contacting one another such that the spool 410 is forced or pressed axially downward to increase the frictional contact between teeth 408 and 414 and thereby prevent rotation of spool 410 in the loosening direction. FIG. 4G further illustrates the teeth 412 and 426 sliding axially up and over one another as the knob 470 and tension control disc 420 are rotated in the loosening direction. As previously described, in some embodiments the knob 470, tension control disc 420, and/or other components (pawl disc 430 and disc 440) may move slightly axially upward and downward as teeth 426 slide up and over spool teeth 412.

In some embodiments, a spring mechanism—e.g., spring washer and the like—(not shown) may be positioned between the spool 410 and the tension control disc 420 to provide an axially downward force on the spool 410. The axially downward force provided by the spring mechanism may cause the spool 410 to move axially downward while some amount of tension remains in the lace. To facilitate downward movement of the spool 410 via the spring mechanism, the angle or taper of the teeth 412 and the teeth 426 of the tension control disc 420 may be adjusted or decreased so that engagement of the teeth does not aggressively pull the spool 410 axially upward. For example, the angle or taper of the teeth 412 and teeth 426 may be 10 degrees or less, 5 degrees or less, and the like, as measured from a plane parallel to an axis of the spool to allow the teeth 412 and the teeth 426 to easily disengage via the spring mechanism. In this manner, the teeth 408 and 414 of housing 404 and spool 410, respectively, may engage with one another to prevent further rotation of spool 410 while some amount of tension remains in the lace. This arrangement may keep or maintain a relatively tight wind of the lace about the spool 410 so as to prevent kinking, buckling, entangling, or other lace issues from occurring within housing 404. This arrangement may also prevent a user from fully loosening the lace tension to prevent the user from removing an article from a limb, such as a brace. Such embodiments may be employed to ensure that a minimum amount of tension remains in the lace to ensure, for example, that a brace or other article is being worn properly. For example, a physician may prescribe a minimum fit or brace pressure for a patient and the closure system may be used to ensure that the patient never loosens the brace beyond the prescribed minimum fit.

In some embodiments, the spring mechanism may be varied to provide a desired amount of axial force on spool 410. For example, a relatively flexible spring mechanism may be used when a small axial force is desired, or a relatively stiff spring mechanism may be used when a large axial force is desired. An intermediate spring stiffness may likewise be used when an intermediate axial force is desired.

Figure 5:
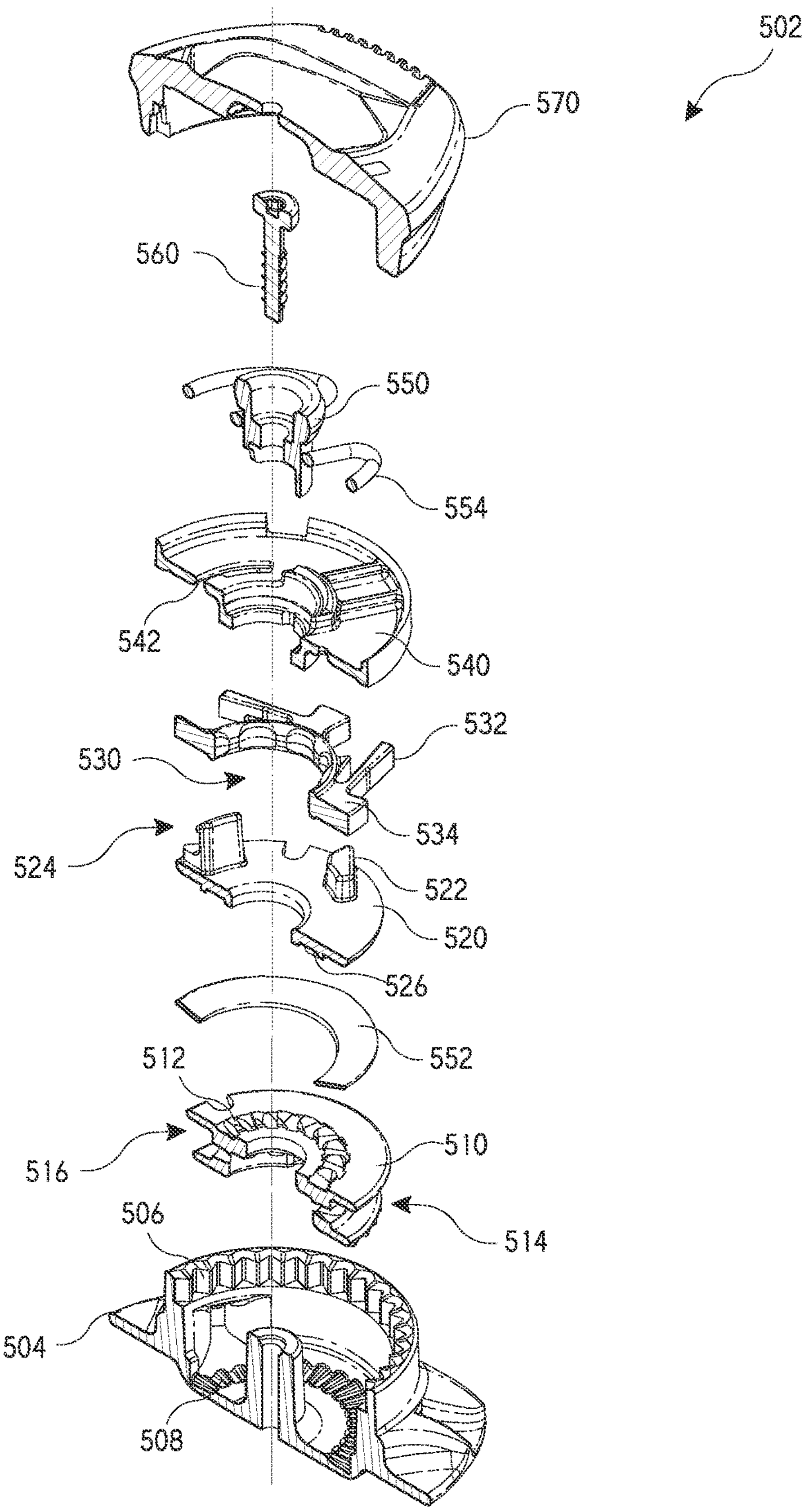
FIG. 5 illustrates an exploded cross-sectional perspective view of another embodiment of a reel assembly that may be used to incrementally tighten or loosen a tension member.

Referring now to FIG. 5, illustrated is a cross sectional view of another embodiment of an incremental lace loosening reel assembly 502. Reel assembly 502 is similar to reel assembly 402 in that reel assembly 502 includes a housing 504, knob 570, spool 510, disc 540, tension control disc 520, and pawl disc 530. Rotation of the knob 570 causes disc 540, pawl disc 530, and tension control disc 520 to rotate as described above. The pawl teeth 532 of pawl disc 530 interact with housing teeth 506 of housing 504 to hold the spool 510 in place as described above. As knob 570 is rotated in a loosening direction, the pawl teeth 532 of pawl disc 530 are swept out of contact with the housing teeth 506 of housing 504 as previously described to allow the spool 510 to counter-rotate and thereby loosen the lace. To prevent back-winding of the lace about spool 510, or in other words to prevent over-rotation of the spool 510 in the loosening direction, the spool 510 is configured to move axially upward and downward within housing 504 such that a stop mechanism (i.e., teeth 514 and 508 of housing 504 and spool 510, respectively) engage and disengage to limit counter-rotation of the spool 510 as previously described. The spool teeth 512 are also angled as previously described to allow the teeth 526 of tension control disc 520 to deflect axially upward and over the spool teeth 512 when teeth 514 and 508 are engaged. The various other components of reel assembly 502 (e.g., components 560, 550, 554, 542, 534, 522, 524, and 516) may function similar to the corresponding component of reel assembly 402.

Unlike reel assembly 402, however, reel assembly 502 includes a spring washer 552 that is positioned between the spool 510 and tension control disc 520 and that functions to bias the spool 510 axially downward and into engagement with the stop mechanism (i.e., biases engagement of teeth 514 and 508). The spring washer 552 allows the stop mechanism to be engaged at a lace tension threshold that may be substantially greater than zero. The use of the spring washer 552 may be important in medical brace applications and/or to further ensure that the lace and/or internal components of reel assembly 502 are protected.

In some embodiments, the reel assembly 502 may not configured to allow a user to pull axially upward on knob 570 to disengage the spool teeth from the housing teeth and thereby allow the spool 510 to freely rotation within housing 504 to fully loosen the lace. Rather, the spool teeth and housing teeth of reel assembly 500 may always be engaged such that tensioning and loosening of the lace is achieved by rotation and counter-rotation of the knob 570.

Figure 6A:
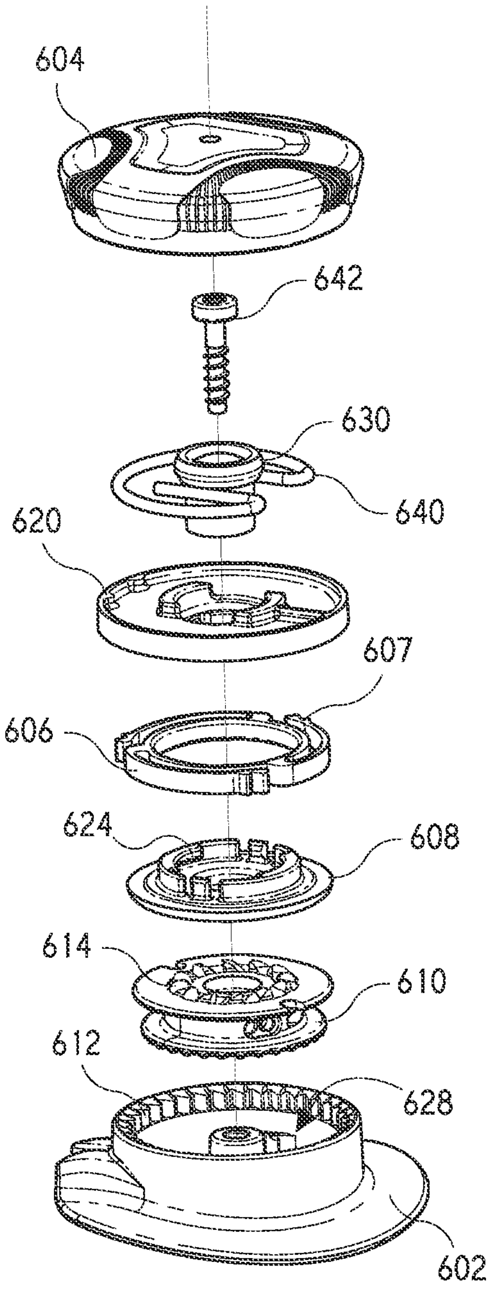
FIGS. 6A-B illustrate exploded perspective views of an embodiment of a reel assembly or reel based closure device that is capable of providing essentially infinite tension member loosening increments or amounts.
Figure 6B:
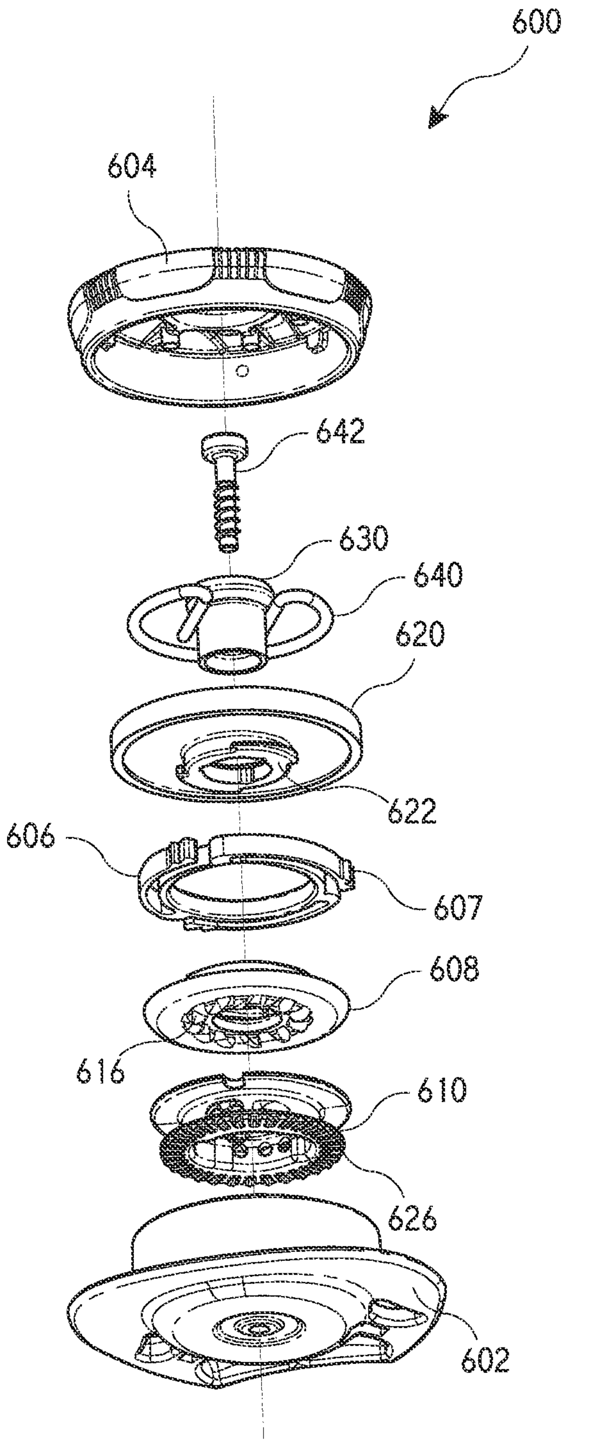
Figure 6C:
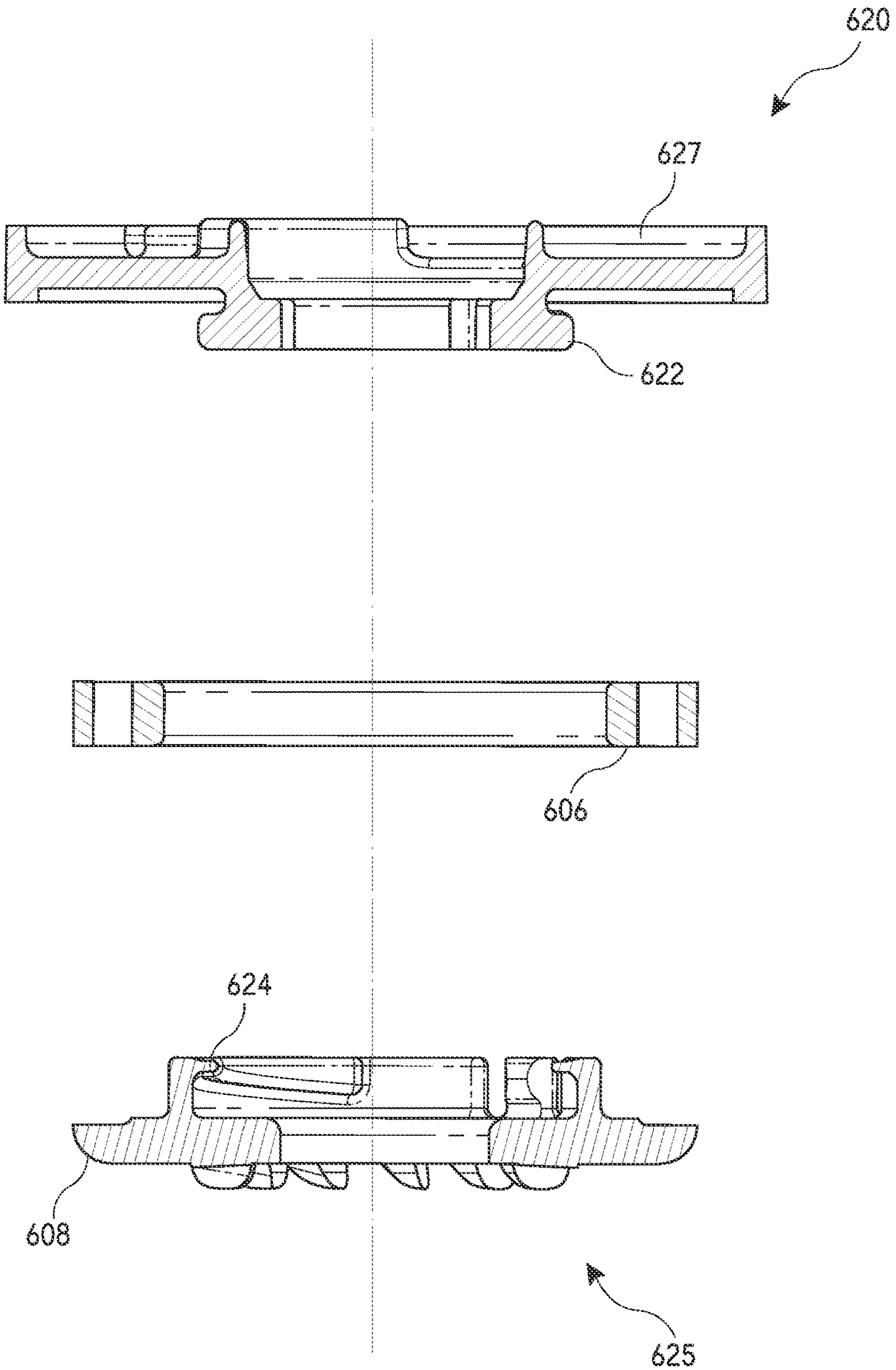
FIGS. 6C-E illustrate exploded perspective views of a tension release mechanism of the reel assembly of FIGS. 6A-B.
Figure 6D:
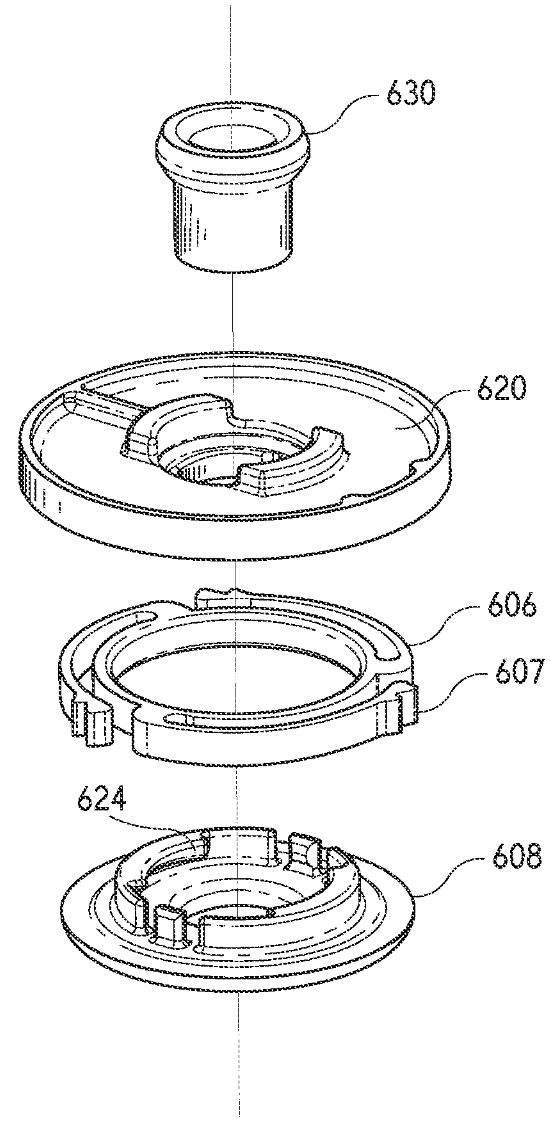
Figure 6E:
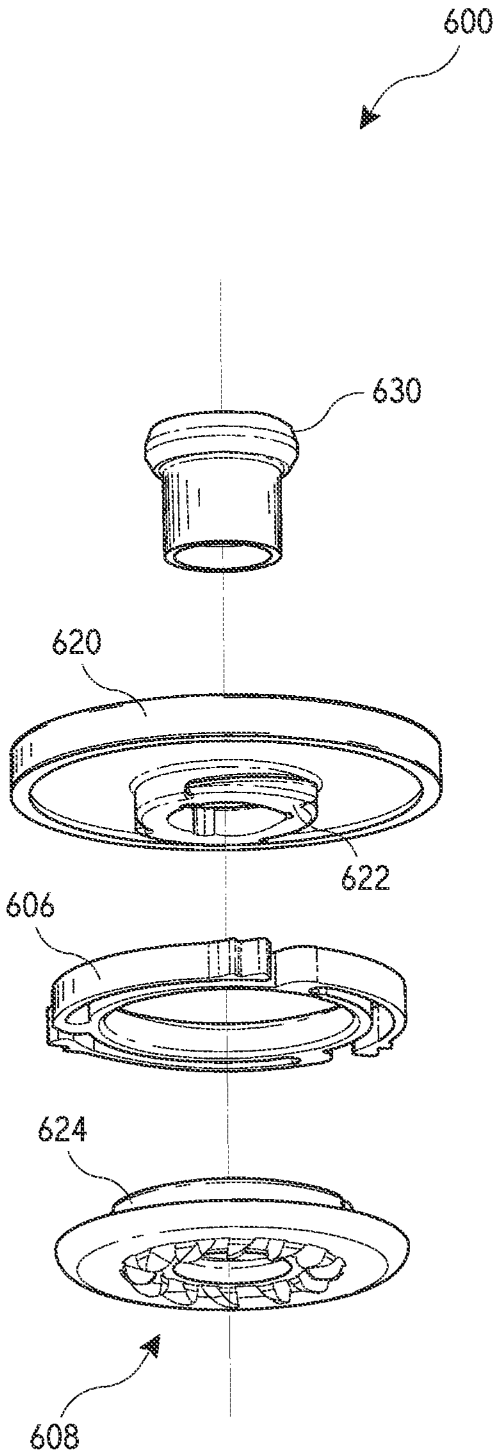
Figure 6F:
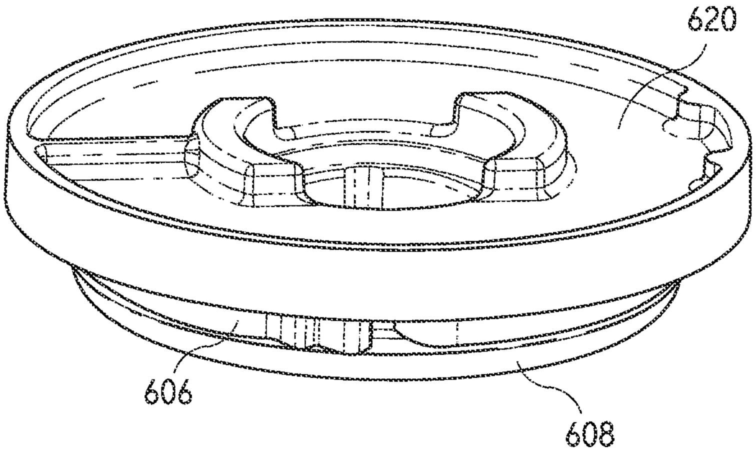
FIG. 6F illustrates a perspective view of the assembled components of the tension release mechanism of FIGS. 6C-E.
Figure 6G:
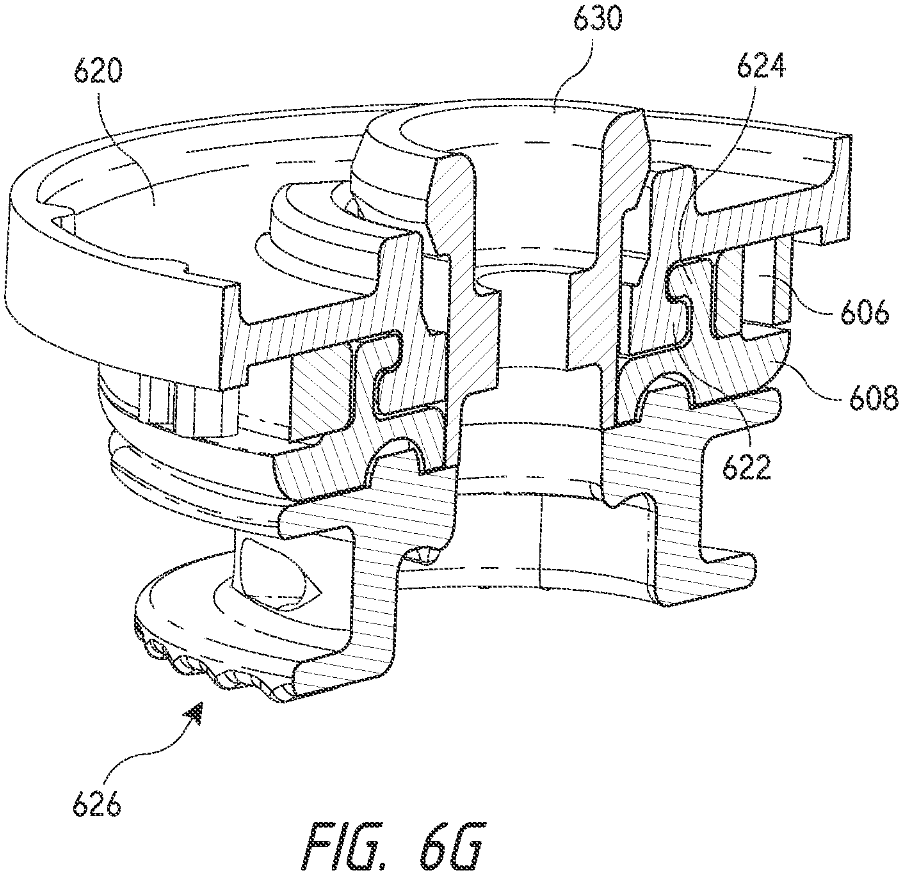
FIG. 6G illustrates a cross-sectional perspective view of the assembled components of the reel assembly of FIGS. 6A-B.

Referring now to FIGS. 6A-G, illustrated is another embodiment of an incremental lace loosening device or system. In this embodiment, the lace loosening device or system is capable of providing essentially infinite lace loosening increments, steps, or amounts. Stated differently, instead of allowing the lace to be loosened in discrete steps or amounts, the lace loosening system of FIGS. 6A-G allows micro-adjustments of lace tension to be made. The system includes a reel assembly 600 having a tensioning mechanism or knob 604 that is rotatable by the user in a tightening and loosening direction to tension and loosen the lace as desired. The knob 604 includes a tension release mechanism that is configured to allow a spool 610 to be rotated in a first direction via a first operation of the knob 604 to incrementally tension the lace and to allow the spool 610 to be rotated in a second direction via a second operation of the knob 604 such that the tension member's tension is releasable in substantially infinitely small increments. Specifically, the tension release mechanism includes a first clutch component or disc 620 that couples with a second clutch component or disc 608. The second disc 608 is in turn coupled with the spool 610 around which the lace is wound. A pawl disc 606 is positioned between the first disc 620 and the second disc 608. The components fit within an interior region of housing 602. FIG. 6G illustrates the assembled components of reel assembly 600 without the housing 602.

As described in greater detail herein below, the first disc 620 and the second disc 608 are axially aligned and frictionally engageable so that a first operation of the knob 604 (i.e., rotation of the knob in the tightening direction) frictionally engages the first disc 620 and the second disc 608 to allow the spool to be rotated in the first direction and so that a second operation of the knob 604 (i.e., rotation of the knob in the loosening direction) disengages the first disc 620 and the second disc 608 to allow the spool 610 to be rotated in the loosening direction. The spool 610 is allowed to rotate in the loosening direction until rotation of the knob 604 in the loosening direction is ceased whereupon the first disc 620 reengages with the second disc 608 if the lace's tension is greater than a tension threshold (e.g., near zero tension). In some embodiments, the tension release mechanism (i.e., first disc 620 and second disc 608) may also be configured to prevent the lace's tension from being loosened via rotation of the knob 604 in the loosening direction after the lace's tension achieves or decreases beyond the tension threshold.

The pawl disc includes pawl teeth 607 that interact with housing teeth 612 of housing 602 as described herein to allow the spool 610 to be wound in the tightening direction and to prevent unwinding of the spool 610 in the loosening direction. Similarly, the spool 610 includes spool teeth 614 that interact with teeth 616 positioned on the bottom surface of the second disc 608. Engagement of the teeth 616 and 614 prevent the spool 610 from rotating in the loosening direction.

As shown in greater detail in the cross sectional side view of FIG. 6C and the perspective views of FIGS. 6D and 6E, the first disc 620 includes a central protrusion that extends axially downward. The central protrusion includes cam surfaces 622 that interact with cam surfaces 624 of an axially upward extending protrusions of second disc 608. The cam surfaces, 622 and 624, are oppositely ramped or angled such that rotation of the first disc 620 in the tightening direction relative to second disc 608 causes the ramped or angled surfaces to slide into frictional engagement, or to increase frictional engagement, which pulls the second disc 608 axially upward relative to first disc 620, or vice versa. Rotation of the first disc 620 in the loosening direction relative to the second disc 608 causes the ramped or angled surfaces to slide out of frictional engagement, or decreases frictional engagement, which allows the second disc 608 to move axially downward relative to first disc 620, or vice versa.

As shown, the cam surfaces 622 of first disc 620 fit axially under the cam surfaces 624 of second disc 608. As the knob 604 and first disc 620 are rotated in the tightening direction, cam surfaces 622 slide relative to cam surfaces 624 to increase the frictional engagement or contact between the two components, which pulls the second disc 608 axially upward relative to first disc 620. Movement of the second disc 608 axially upward relative to first disc 620 compresses or pinches the pawl disc 606 between the first disc 620 and second disc 608 as shown in FIG. 6F, which locks or maintains the discs (i.e., the first disc 620, second disc 608, and pawl disc 606) in position. The pawl disc 606 is rotationally maintained or locked in place relative to housing 602 via the interaction between the pawl teeth 607 and the housing teeth 612. The spool 610 is maintained or locked in rotational position relative to the housing 602 via the pressed or pinched pawl disc 606 and the interaction between the spool teeth 614 and the teeth 616 of second disc 608. In this manner, the components of reel assembly 600 are held in rotational position relative to the housing 602 and counter-rotation (i.e., rotation in the loosening direction) is prevented.

Further rotation of the knob 604 in the tightening direction causes the first disc 620, the second disc 608, and the pawl disc 606 to also rotate in the tightening direction via the interaction between the cam surfaces 622 and 624 and the compression of the pawl disc 606 between the first and second discs 620 and 608. Rotation of the second disc 608 in the tightening direction also causes the spool 610 to rotate in the tightening direction via interaction of the teeth 614 and 616, which allows the lace to be further tensioned.

When the knob 604 is counter-rotated or rotated in the loosening direction, the cam surfaces 622 and 624 begin to frictionally disengage, which allows the second disc 608 to move axially downward and loosens the compressive pressure exerted on the pawl disc 606. As the compressive pressure exerted on the pawl disc 606 is reduced, the second disc 608 becomes frictionally unlocked from the pawl disc 606 and is able to slip or rotate in the loosening direction, which allows the lace tension to be loosened. As long as a predetermined amount of tension exists in the lace, the lace will cause the spool 610 to rotate in the loosening direction, which causes the second disc 608 to also rotate in the loosening direction. Rotation of the second disc 608 in the loosening directions causes the cam surfaces 624 to rotate relative to the cam surfaces 622 of first disc 620 thereby frictionally reengaging the cam surfaces 624 and 622 and discs 620 and 608. This reengagement of the cam surfaces, 624 and 622, and the respective discs, 608 and 620, recompresses the pawl disc 606 and locks the discs in position, thereby preventing further counter-rotation of the discs.

The slippage of the second disc 608 relative to first disc 620 may be relatively instantaneous such that a user is unable to detect or otherwise notice the slippage of the second disc 608. Similarly, the frictional re-engagement of the first disc 620 and second disc 608 may be unnoticeable or undetectable by the user such that as the user stops counter rotation of the knob 604 (i.e., rotation of the knob 604 in the loosening direction), the user may be unable to detect or notice any additional movement of the second disc 608 or any other internal component. Rather, the user may believe that rotation of the knob 604 in either the tightening or loosening direction results in immediate rotation of the second disc 608 and spool 610 corresponding to an immediate tensioning or loosening of the lace. Since the rotation of the second disc 608 may be virtually identical to the rotation of the knob 604, the reel assembly 600 provides essentially an infinite amount and relatively precise lace loosening adjustment. Stated differently, a user may counter rotate the knob 604 by essentially infinitely small increments, degrees, or amounts, which causes loosening of the lace by correspondingly small increments, degrees, or amounts. The tension release mechanism (i.e., first disc 620 and second disc 608) of reel assembly 600 allows the spools 610 to be releaseably locked in any angular orientation within the housing upon cessation of counter-rotation of the knob 604. This allows the lace's tension to be loosened or released in substantially infinitely small increments as described above.

In some embodiments, the cam surfaces 622 may be directly incorporated with the knob 604 rather than being included on a separate disc 620. Similarly, the second disc 608 may be incorporated with the spool 610 rather than using separate components. Other components of reel assembly 600 may likewise be integrated to reduce the overall component count.

In some embodiments, the reel assembly 600 may include a stop mechanism that prevents rotation of the spool 610 in the loosening direction after the lace's tension achieves or decreases beyond a tension threshold. For example, a bottom surface of the spool 610 includes teeth 626 that extend axially downward from a bottom surface of the spool 610. As described above, the teeth 626 may engage with corresponding teeth 628 that extend axially upward from an inner surface of the housing 602 to prevent or restrict rotation of the spool 610 in the loosening direction after the lace's tension achieves or decreases beyond a tension threshold. As described above, the spool 610 may move axially upward and downward to engage and disengage the stop mechanism (i.e., engage and disengage teeth 626 and 628). In some embodiments, as the knob 602 is rotated in the loosening direction after the teeth 626 and 628 are engaged, the cam surfaces 622 and 624 may be configured to skip over or relative to one another. In other embodiments, engagement of the teeth 626 and 628 may prevent further rotation of the knob 604 in the loosening direction.

In some embodiments, the reel assembly 600 may also include a full release mechanism that is transitionable between an engaged state and a disengaged state. The full release mechanism may include a bushing 630 and spring component 640 as previously described that transition between the engage state and the disengaged state when the knob 604 is pulled axially upward or pushed axially downward relative to housing 602. In such embodiments, when the full release mechanism is in the engaged state (i.e., positioned axially downward relative to housing 602), the knob 604 may be rotated to tension or loosen the lace. When the full release mechanism is in the disengaged state (i.e., positioned axially upward relative to housing 602), the lace's tension may be automatically and/or fully loosened or released.

In some embodiments, the pawl disc 606 may be configured to fit around the cam surface 624 of second disc 608. This configuration may allow the first disc 620 and second disc 608 to more easily compress the pawl disc 606 and/or allow greater compressive pressures to be exerted on the pawl disc 606.

Figure 7A:
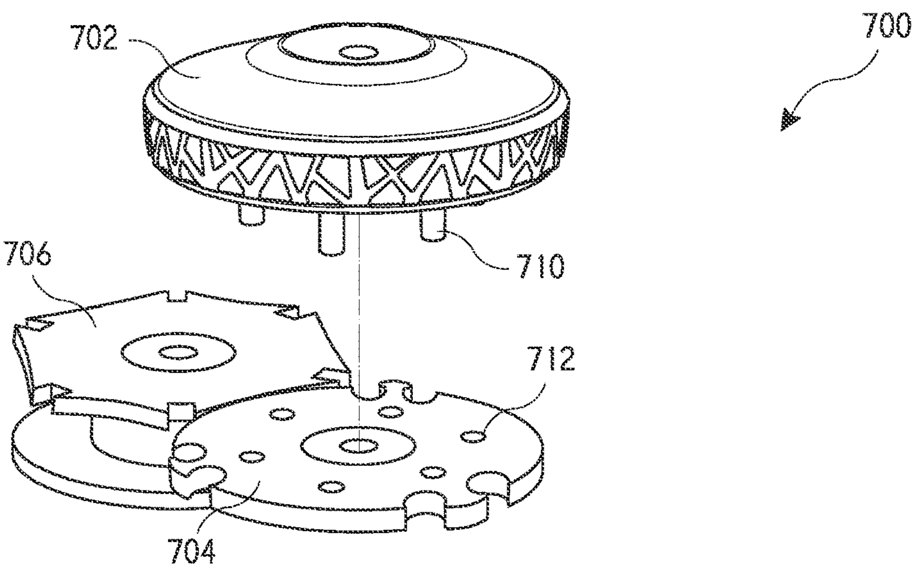
FIGS. 7A-B illustrate another embodiment of a reel assembly that may be used to incrementally loosen a tension member.
Figure 7B:
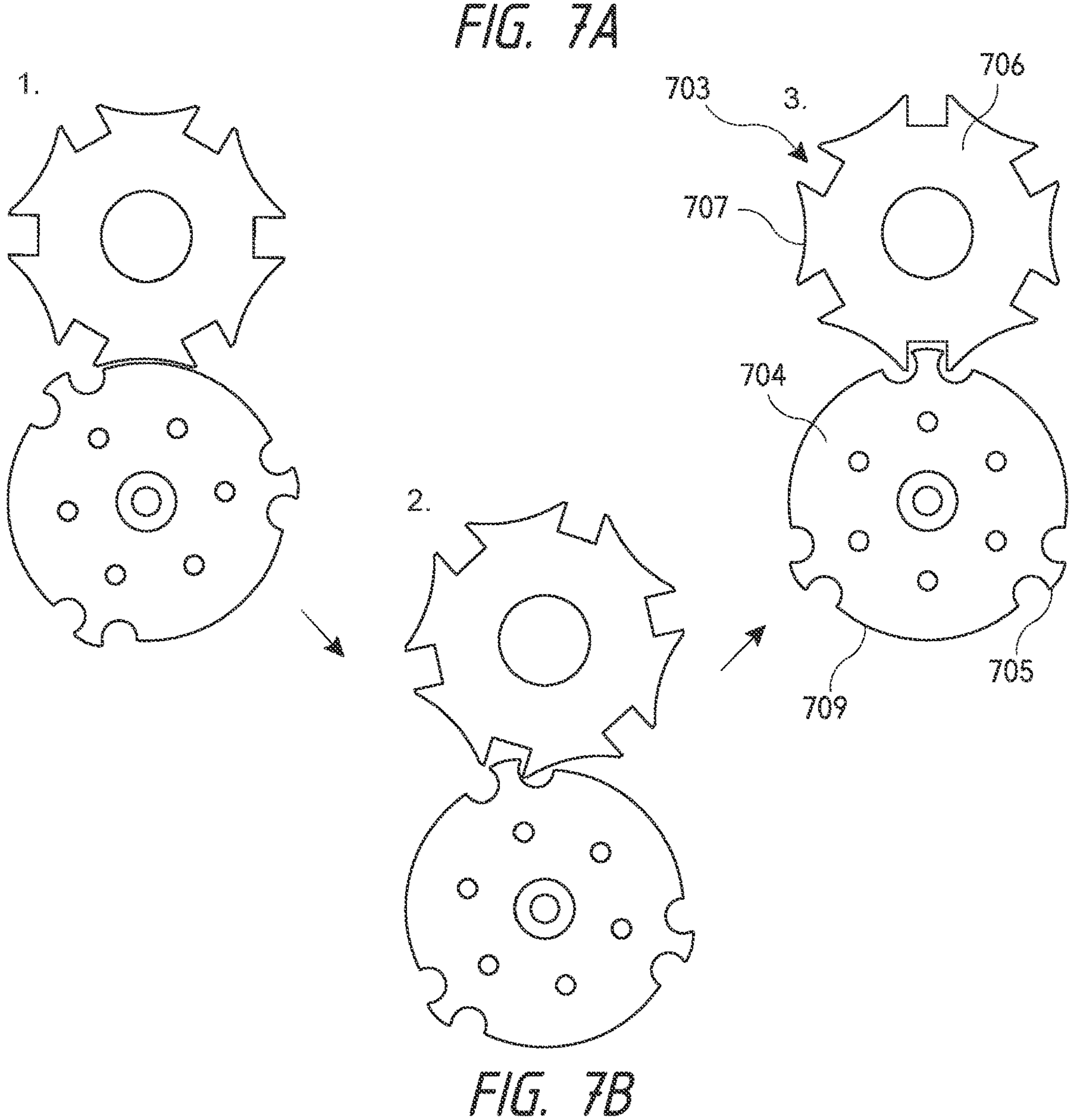

Referring now to FIGS. 7A and 7B, illustrated is another embodiment of an incremental lace loosening system. Specifically, FIGS. 7A and 7B illustrate a reel assembly 700 having a knob 702 that is rotatable by a user as described herein. The knob 702 couples with a drive disc 704 that is rotated as the user rotates knob 702. The drive disc 704 may include a plurality of apertures 712 through which corresponding shafts 710 of the knob 702 are inserted in order to drive rotation of disc 704 via rotation of knob 702. Drive disc 704 in turn is used to drive spool 706 in both the tightening and loosening direction. Drive disc 704 includes gear teeth or cogs 705 that fit within recesses 703 of spool 706 in order to drive spool 706.

A profile of the outer surface 707 of spool 706 corresponds to a profile of the outer surface 709 of drive disc 704 such that during rotation of the drive disc 704 while the teeth 705 and recesses 703 are disengaged, the outer surface 709 of drive disc 704 slides along the outer surface 707 of spool 706. The configuration of the outer surfaces, 707 and 709, of the spool 706 and drive disc 704, respectively, prevents rotation of the spool 706 in the loosening direction because any such rotation causes the outer surface 707 of the spool 706 to contact the outer surface 709 of the drive disc 704. In this manner, the spool 706 and drive disc 704 are essentially locked in place by the configuration of the outer surfaces, 707 and 709, of the components. The embodiment of FIGS. 7A and 7B provide a silent tightening/loosening mechanism that generally requires less parts than other tightening mechanisms. The embodiment also allows for very small incremental tightening/loosening steps, which allows for precise lace tensions to be achieved.

Figure 8:
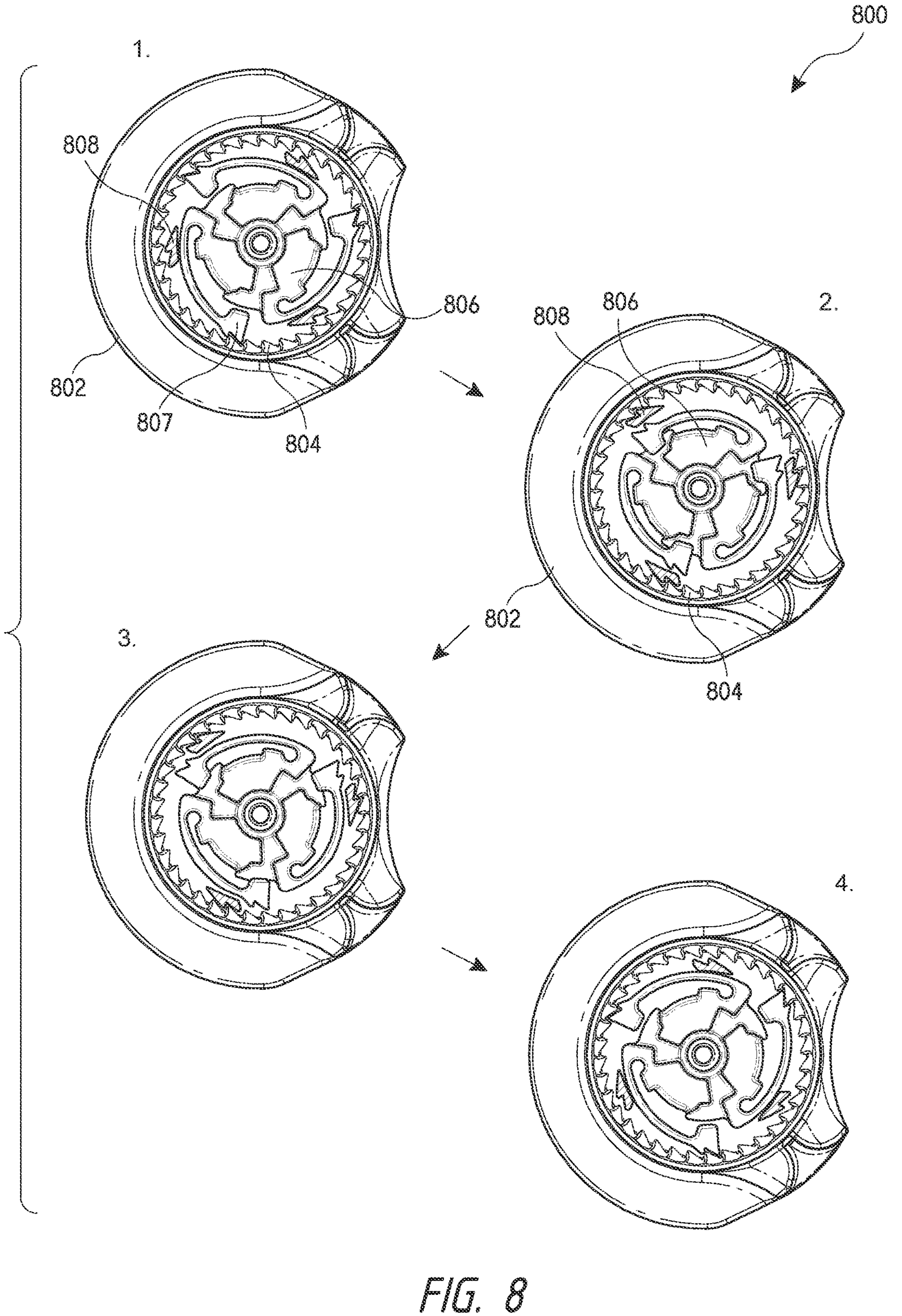
FIG. 8 illustrates another embodiment of a reel assembly that may be used to incrementally loosen a tension member.

Referring now to FIG. 8, illustrated is another embodiment of a device or system that allows the lace tension to be incrementally loosened. Specifically, FIG. 8 illustrates a reel assembly 800 having a pawl disc 806 that is positioned within a housing 802 as described herein such that the pawl teeth 807 of pawl disc 806 interact with the housing teeth 804 of housing 802 to prevent counter rotation of the spool (not shown). In order to allow the lace tension to be incrementally loosened, reel assembly 800 includes a plurality of sweeper arms 808 that are coupled with a knob (not shown) of reel assembly 800. As shown in image 2, as the knob of reel assembly 800 is counter rotated (i.e., rotated in the loosening direction), the sweeper arms 808 contact the pawl teeth 807 and sweep the pawl teeth 807 out of contact with the housing teeth 804. At the same time, sweeper arms 808 flex radially outward such that teeth of the sweeper arms 808 deflect into contact with the housing teeth 804 (image 2 and 3).

If tension exists within the reel assembly's lace, the tension will cause the spool (not shown) to counter rotate (i.e., rotate in the loosening direction), which will cause the pawl disc 806 to also counter rotate. Counter rotation of the pawl disc 806 will cause the pawl teeth 807 to become disengaged from the sweeper arms 808 and to radially deflect outward and into contact with the housing teeth 804 (image 4). If tension does not exist within the reel assembly's lace, the spool and pawl disc 806 will not counter rotate. Rather, the spool and pawl disc 806 will remain in relatively the same position engaged with the sweeper arms 808. In this manner, the lace may be loosened only while essentially some amount of tension remains in the lace, which may prevent some of the lace loosening problems identified above. The sweeper arms 808 will remain engaged with the housing teeth 804 until the knob (not shown) is released or rotated slightly in the tightening direction. In this manner, the incremental loosening of the lace is achieved via back-and-forth rotation of the reel assembly's knob. In some embodiments, the knob may be biased so as to disengage the sweeper arms 808 from the housing teeth 804 upon a user releasing the knob.

Figure 9A:
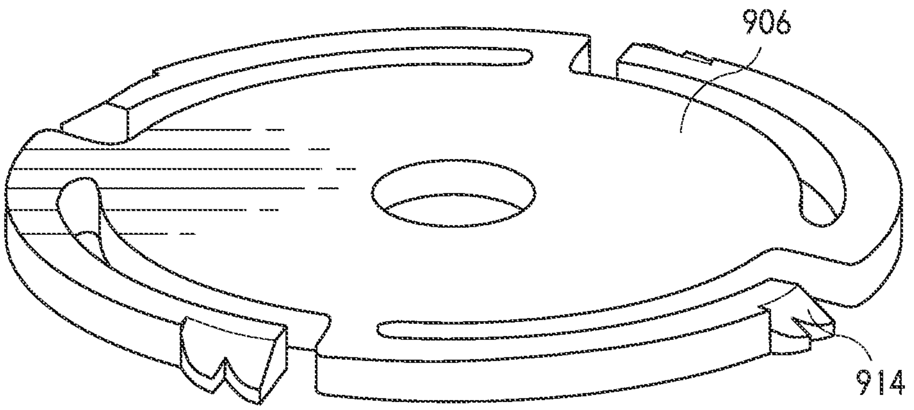
FIGS. 9A-C illustrate an embodiment of a reel assembly that is configured so that axially pressing a knob or button causes a tension member's tension to be incrementally loosened.
Figure 9B:
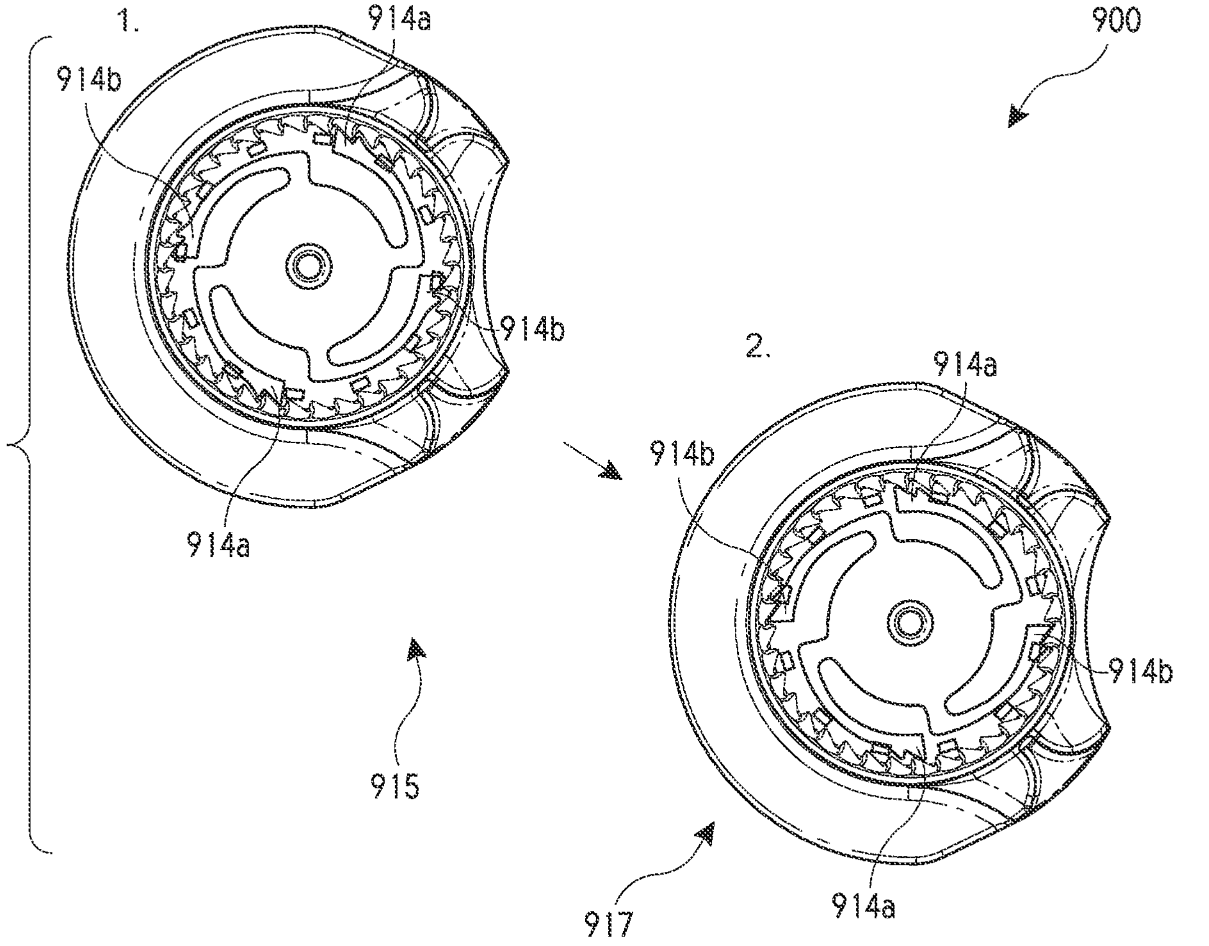
Figure 9C:
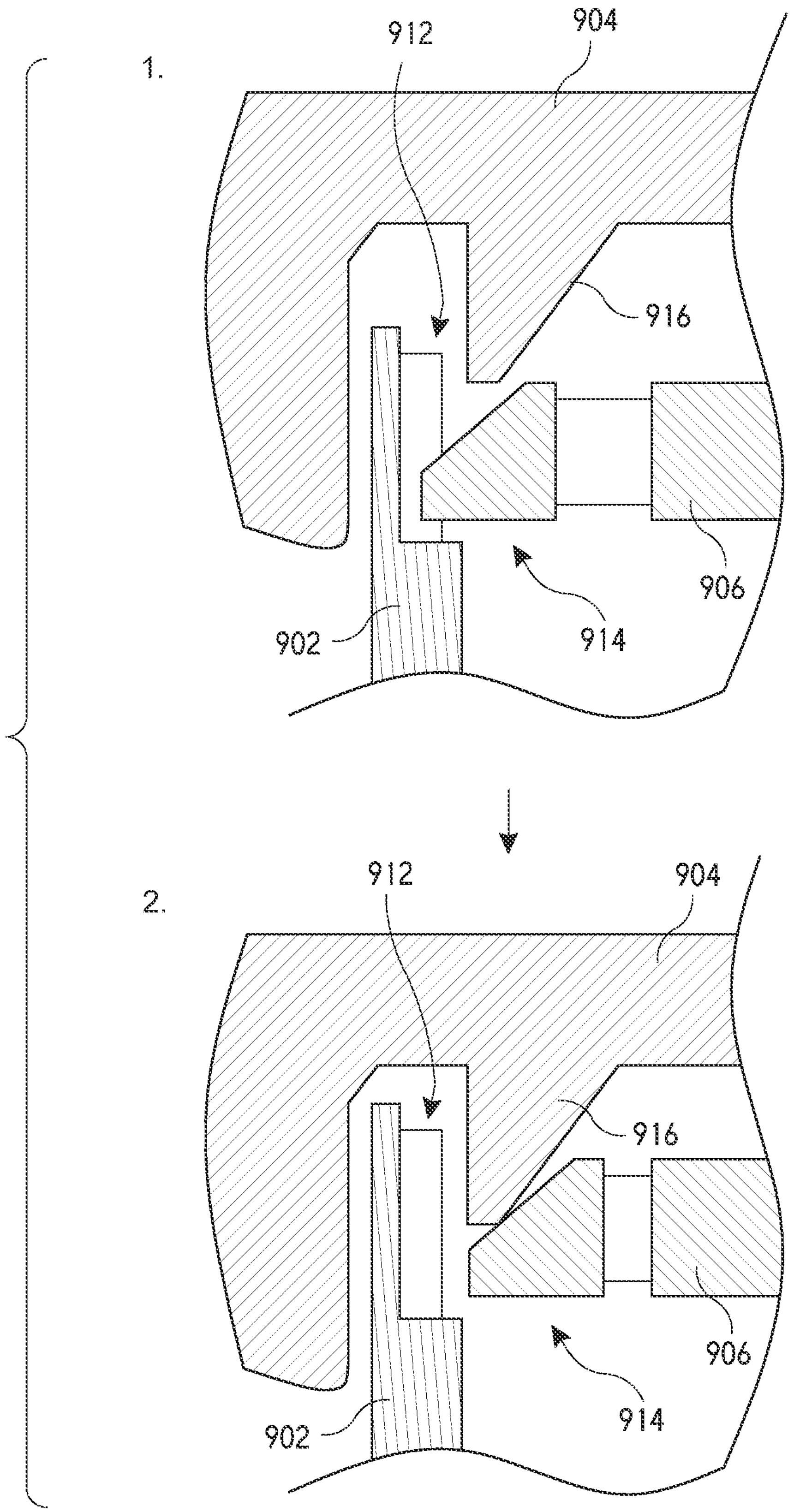
Figure 9D:
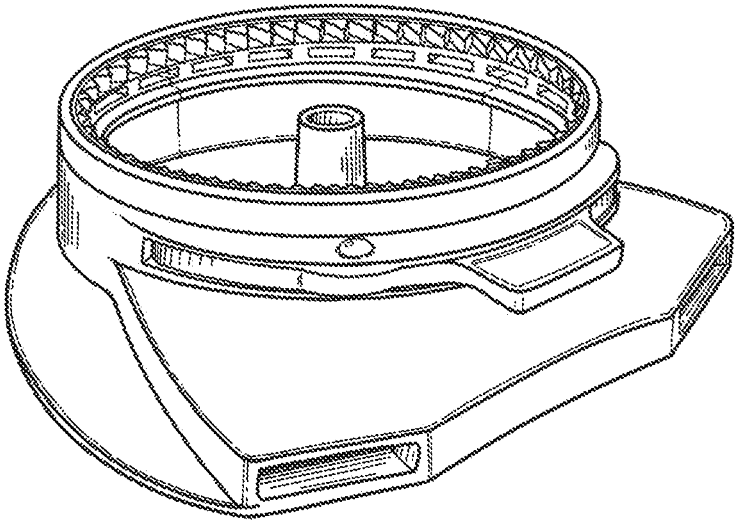
FIGS. 9D-H illustrate an embodiment of a reel assembly that is configured so that radially pressing a button causes a tension member's tension to be incrementally loosened.
Figure 9E:
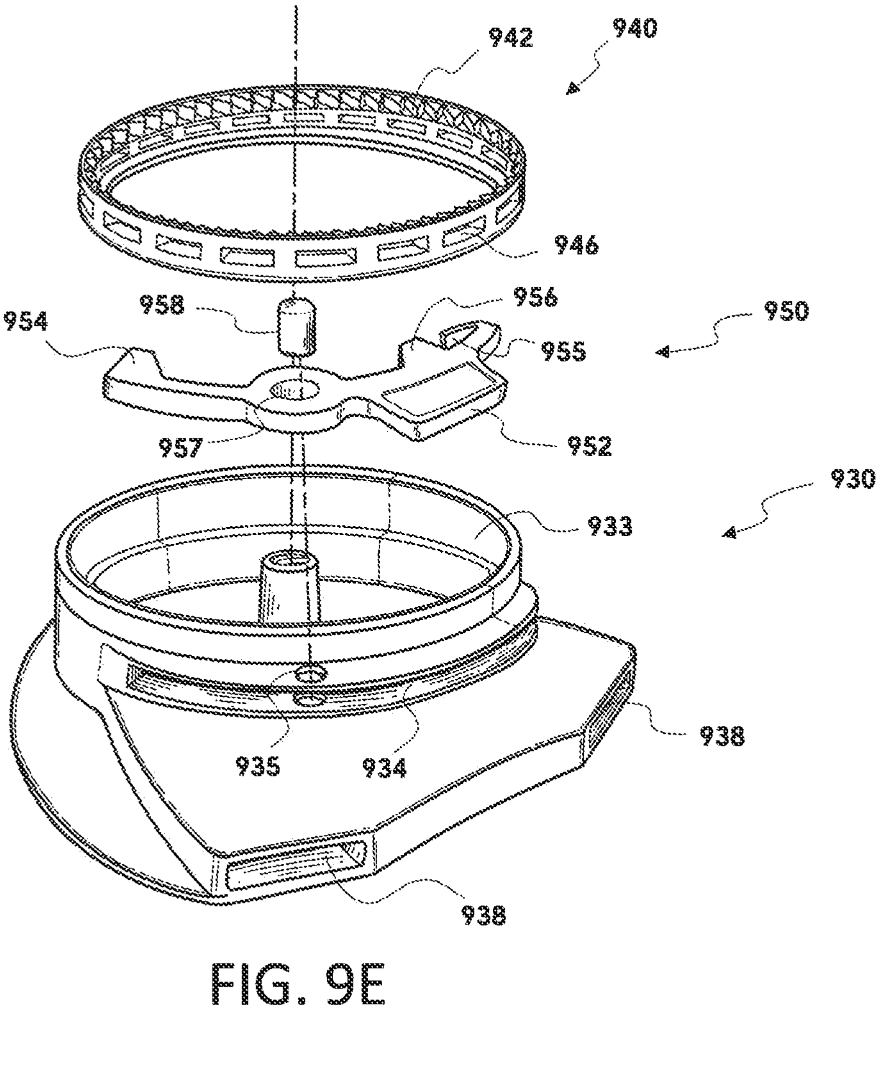
Figure 9F:
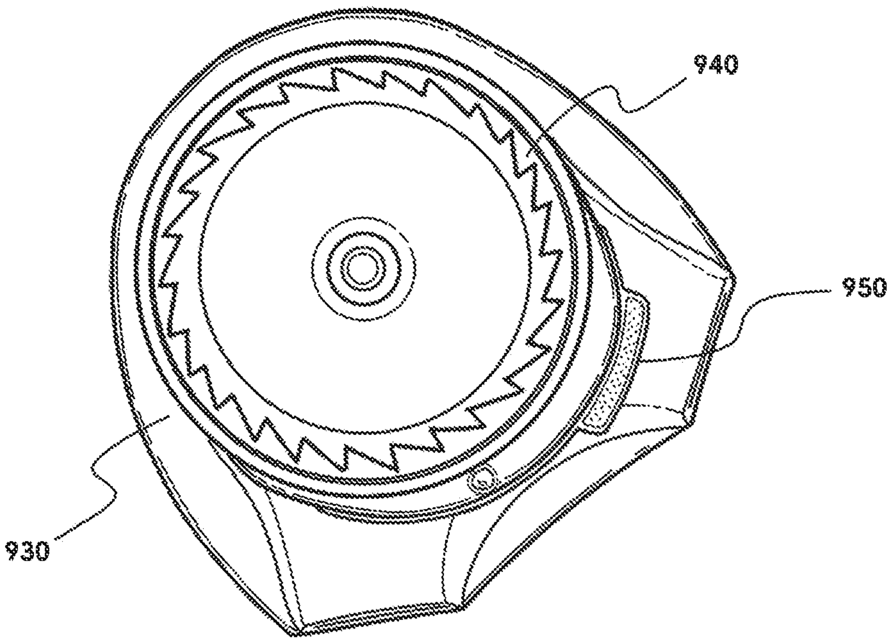

Referring now to FIGS. 9A-K, illustrated are embodiments of incremental lace loosening systems or devices in which pressing a knob or button causes the lace tension to be incrementally loosened. Specifically, FIGS. 9A-C illustrate a reel assembly 900 wherein pressing the knob 904 axially downward relative to the housing 902 causes the pawl teeth 914 of pawl disc 906 to be temporarily disengaged from the housing teeth 912 of housing 902. As shown in FIGS. 9A-C, the pawl teeth 914 have a chamfered or angled upper surface that is engaged by an axially downward extending protrusion 916 of knob 904. The downward extending protrusion 916 includes a chamfered or angled bottom surface that contacts the chamfered or angled upper surface of pawl teeth 914 to causes the pawl teeth 914 to deflect radially inward and out of engagement with the housing teeth 912 upon depression of the knob 904 axially downward relative to housing 902.

Disengagement of the pawl teeth 914 from the housing teeth 912 causes the spool (not shown) and pawl disc 906 to rotate in the loosening direction as long as some amount of tension remains in the lace. Rotation of the pawl disc 902 in the loosening direction causes the pawl teeth 914 to become disengaged from the protrusion 916 of knob 904, which causes the pawl teeth 914 to deflect radially outward and into engagement with the housing teeth 912. In this manner, incremental loosening of the lace is achieved each time the knob 904 is pressed axially downward.

In some embodiments, the pawl disc 906 may include a pair of teeth that are always engaged with the housing teeth 912 and a pair of teeth that are always disengaged from the housing teeth 912. For example, as shown in FIG. 9B, a first pair of pawl teeth 914*a* may be engaged with the housing teeth 912 while a second pair of pawl teeth 914*b* is disengaged from the housing teeth 912. The pairs of housing teeth, 912*a* and 912*b*, may be configured such that the pairs of teeth are a half step off from one another, or in other words so that the non-engaged pair of teeth is halfway engaged with the housing teeth 912. The knob 904 may be configured so that the protrusions 916 are always positioned axially above the pair of teeth (i.e., initially pawl teeth 914*a*) that are engaged with the housing teeth 912. Depression of the knob 904 causes the engaged pair of teeth 914*a* to disengage from housing teeth 912, which causes counter rotation of the pawl disc 906 as described above. As the pawl disc 906 counter-rotates, the previously disengaged teeth 914*b* will engage with the housing teeth 914 while the previously engaged teeth 914*a* remain disengaged from housing teeth 912. In this manner, depression of the knob 904 will cause the lace to be loosened in half steps increments. The half step increments may also help reduce the impact of the pawl teeth during engagement with the housing teeth, which may increase the life of the pawl teeth and reel assembly. In some embodiments, the knob 904 may rotate after each depression so that the protrusions 916 are always positioned axially above the pair of teeth that are engaged with the housing teeth 912.

Referring now to FIGS. 9D-H, illustrated is another embodiment of an incremental lace loosening system where depression of a button causes incremental loosening of the lace. The system of FIGS. 9D-H includes a housing 930 that is similar to the reel assembly housings previously described. For example, housing 930 includes lace ports 938 within which the lace enters and exits the housing 930. Unlike the other housings, however, housing 930 does not include housing teeth that are rigidly coupled with an interior space of the housing 930. Rather, a toothed ring or disc 940 is positioned within a cylindrical inner surface 933 of housing 930. The toothed ring 940 is configured to be rotatable within the cylindrical inner surface 933 of housing 930 rather than rigidly coupled therewith. The toothed ring 940 includes a plurality of teeth 942, which are configured to interact with pawl teeth (not shown) of a pawl disc (not shown) as previously described to prevent counter rotation of the pawl disc and a spool (not shown).

A button mechanism 950 is coupled with housing 930 to prevent rotation of the toothed ring 940. Specifically, housing 930 includes a recess or channel 934 within which the button mechanism 950 is positioned. To couple the button mechanism 950 with the housing 930, a pin 958 is inserted within an aperture 935 of the channel 934 and through a corresponding aperture 957 of button mechanism 950. Pin 958 pivotably couples the button mechanism 950 within channel 934. Button mechanism 950 includes a pressable portion 952 and two protrusions 954 and 956 that are positioned on opposite ends of the button mechanism 950.

Figure 9G:
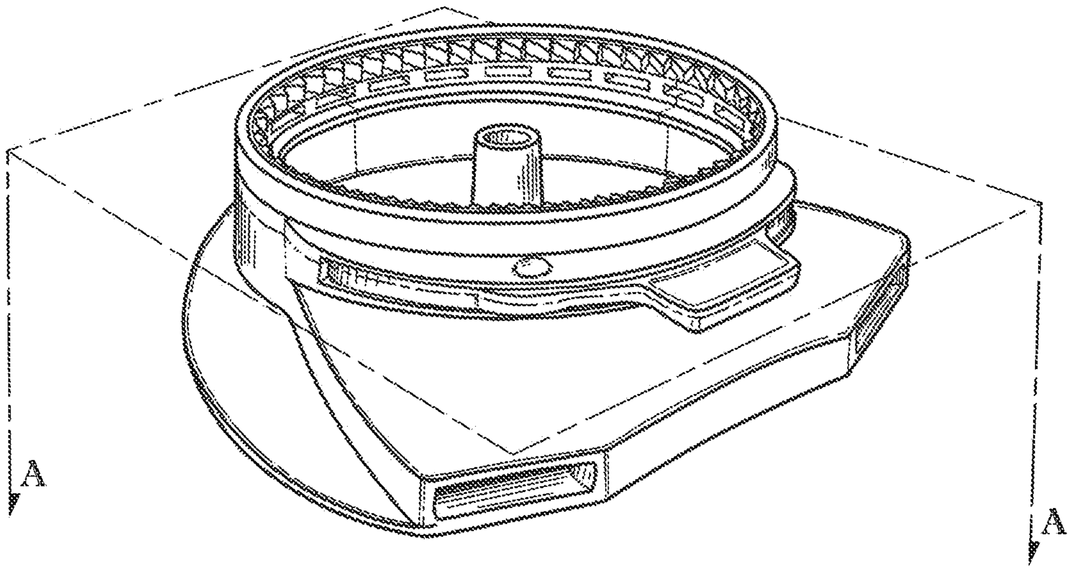
Figure 9H:
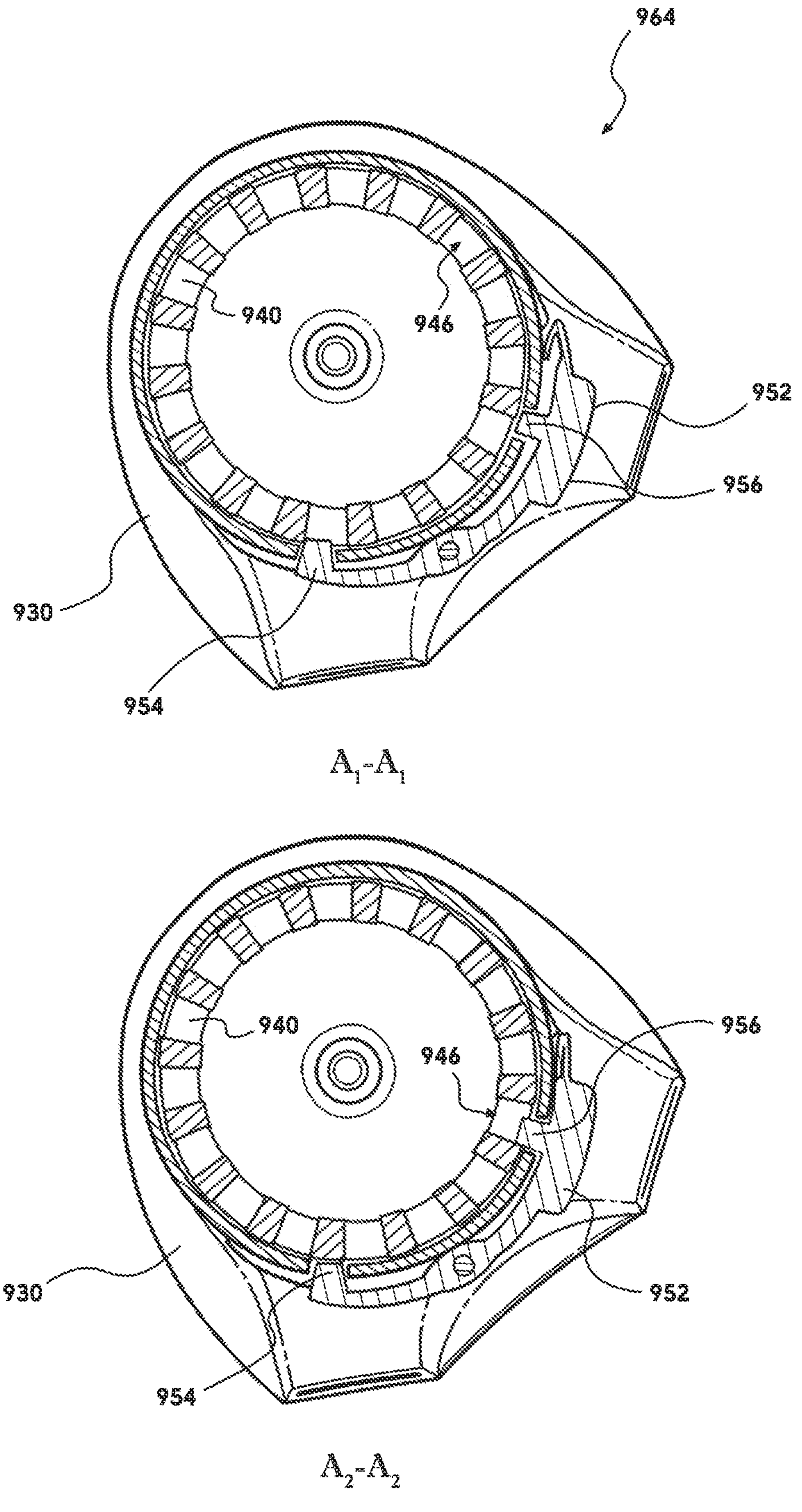

As shown in FIG. 9H, which is a top cross sectional view taken along plane A-A of FIG. 9G, as the button mechanism 950 pivots within channel 934 via radially pressing of portion 952, one of the protrusions, 954 or 956, pivots radially through an aperture or window of housing 930 and into the cylindrical inner surface 933 while the other protrusion, 954 or 956, pivots radially outside of the cylindrical inner surface 933. Radially pressing portion 952 of button mechanism 950 causes the protrusions, 954 and 956, to displace radially into and out of the inner cylindrical surface 933 of housing 930.

The toothed ring 940 includes a plurality of apertures or recesses 946 within which the protrusions, 954 and 956, of button mechanism 950 are positionable. As long as one of the protrusions, 954 or 956, is positioned within one of the recesses 946 of the toothed ring 940, the toothed ring 940 will be prevented from rotating. Radially pressing the portion 952 of button mechanism 950 to pivot the protrusions, 954 and 956, however, will allow the toothed ring 940 to temporarily rotate in the loosening direction. For example, as shown in FIG. 9H, in a first state protrusion 954 is positioned within one of the recesses 946 of toothed ring 940 while protrusion 956 is displaced outside of the recesses 946. Depressing the portion 952 causes button mechanism 950 to pivot such that protrusion 954 is pivoted out of the recesses 946 while protrusion 956 is pivoted into another recesses 946.

The protrusions, 954 and 956, are configured so that as the protrusions pivot into and out of the recesses 946, the toothed ring 940 incrementally rotates in the loosening direction. For example, as protrusion 956 is pivoted within a recess 946, the toothed ring 940 will rotate slightly in the loosening direction before a wall of the recess 946 contacts the protrusion 956. Similarly, as protrusion 954 is pivoted within a recess 946, the toothed ring 940 will rotate slightly in the loosening direction before a wall of the recess 946 contacts protrusion 954. In this manner, each time the portion 952 is pressed, the toothed ring 940 will be allowed to rotate in the loosening direction by some incremental amount. The button mechanism 950 may include a spring 955, or other biasing mechanism, that biases the button mechanism 950 toward the first state with protrusion 954 positioned within a recess 946. Stated differently, as a user releases portion 952, the button mechanism 950 may automatically pivot so that protrusion 954 is positioned within a recess 946. In this manner, a user may merely press and release portion 952 of button mechanism 950 to cause incremental loosening of the lace. Because the toothed ring 940 is able to rotate in the loosening direction, the pawl disc (not shown), spool (not shown), and/or other components (e.g., knob and the like) that are coupled with the toothed ring 940 are also able to rotate.

Rotation of the toothed ring 940 in the loosening direction is actuated by lace tension. As such, when the lace tension is essentially fully loosened or released, counter-rotation of the toothed ring 940 and other reel assembly components with be prevented or limited. For example, as the lace tension pulls on the spool (not shown), a counter-rotational force is transmitted to the spool and any components coupled therewith, such as the toothed ring 940. The counter-rotational force that is transmitted to the toothed ring 940 via the lace tension and spool will cause the toothed ring to counter rotate as the portion 952 is pressed. In this manner, the toothed ring 940 and spool will only rotate as long as some level of tension exists within the lace and will not rotate when the lace tension is fully loose or released.

Figure 9I:
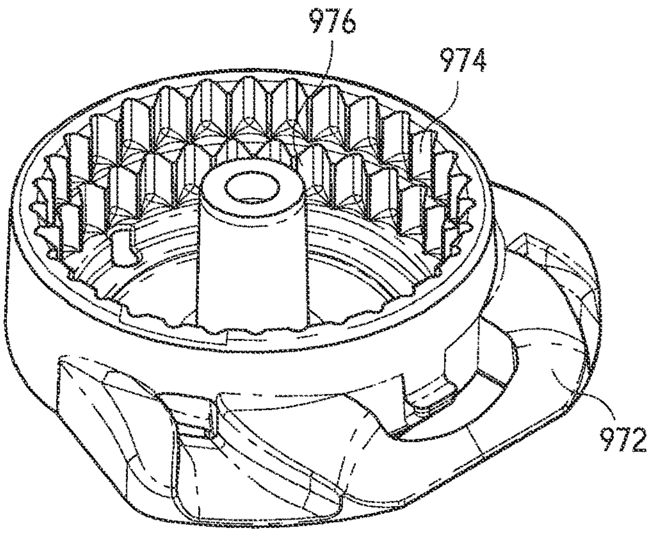
FIGS. 9I-K illustrate an embodiment of a reel assembly that is configured so that axially pressing a knob or button causes a pawl disc to displace axially within the reel assembly's housing to incrementally loosen a tension member's tension.
Figure 9J:
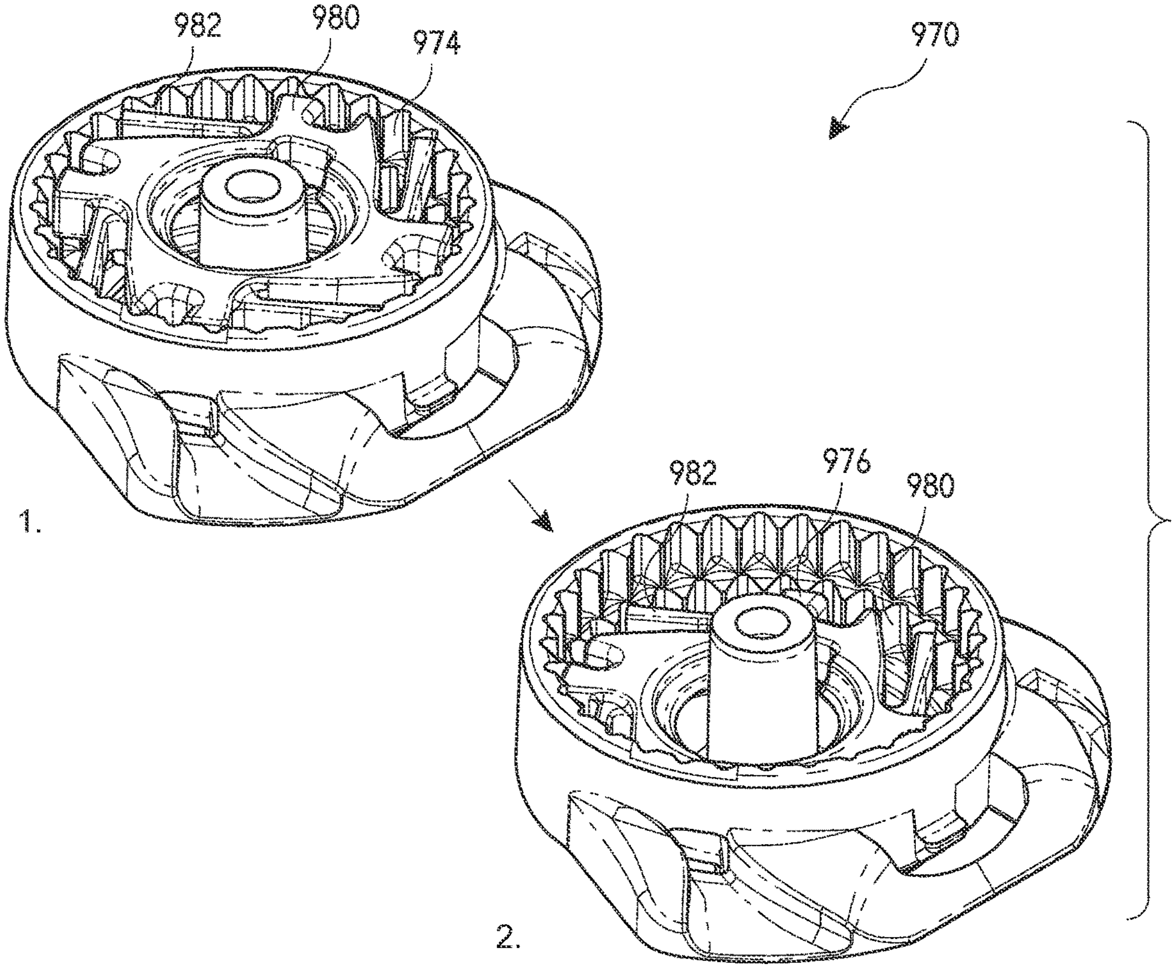
Figure 9K:
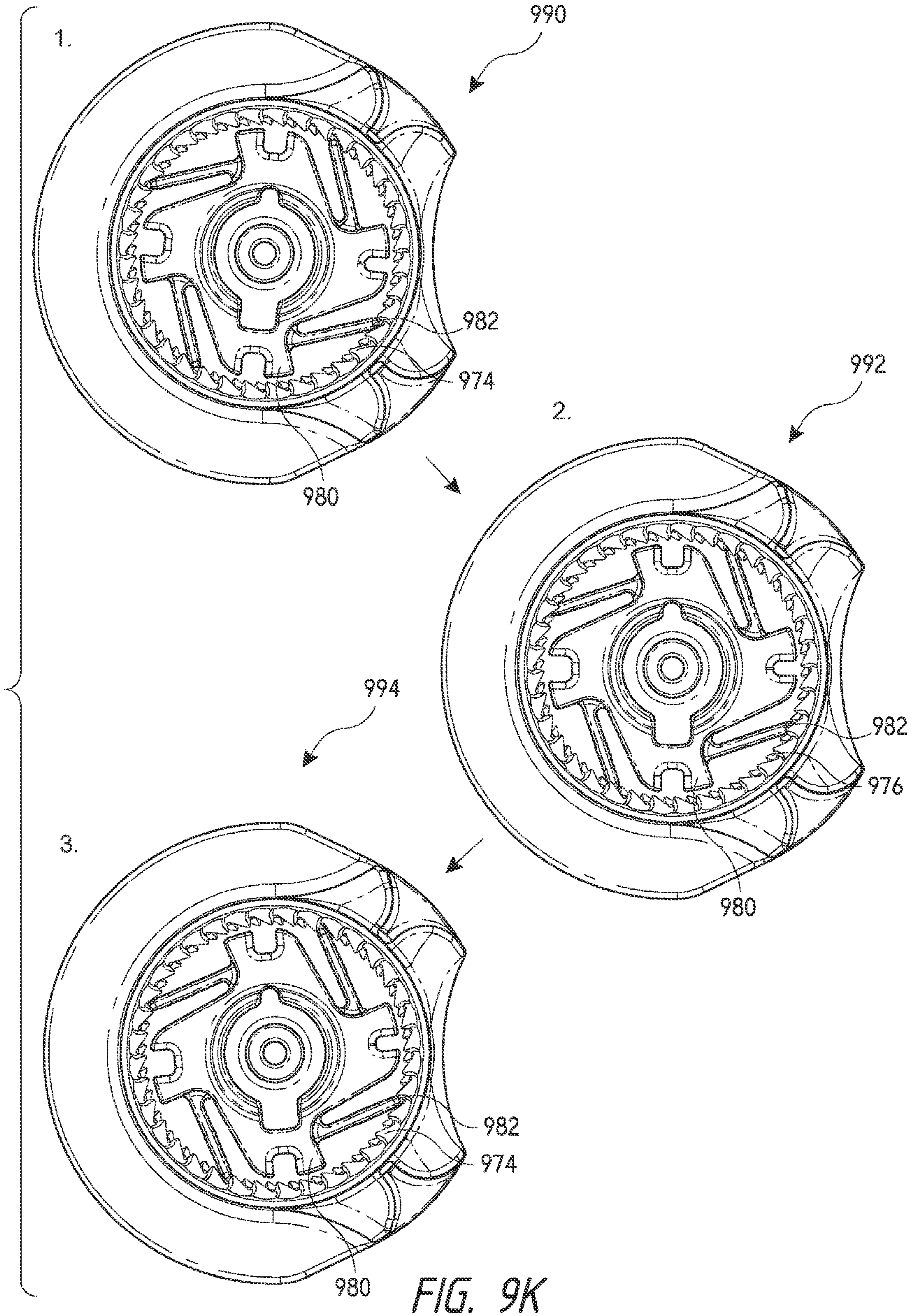

Referring now to FIGS. 9I-K, illustrated is another embodiment of an incremental lace loosening system. The reel assembly 970 of this system achieves incremental lace loosening as a pawl disc 980 displaces axially upward and downward within the reel assembly's housing 972. Specifically, housing 972 includes a first level of housing teeth 976 and a second level of housing teeth 974 that is positioned axially above the first level of housing teeth 976. As the pawl disc 980 is pressed axially downward relative to the housing 972, the pawl teeth 982 are forced from the second level of housing teeth 974 into the first level of housing teeth 976. Similarly, as the pawl disc 980 is moved axially upward relative to the housing 972, the pawl teeth 982 are forced from the first level of housing teeth 976 into the second level of housing teeth 974.

The levels of housing teeth, 976 and 974, are arranged such that each movement from one level of housing teeth to the other level of housing teeth causes an incremental counter-rotation of the pawl disc 980 and any components coupled therewith (e.g., the spool, knob, and the like) in the loosening direction. In some embodiments, each movement between housing teeth levels may cause a half step rotation—or in other words, may cause the pawl disc 980 to rotate approximately ½ the circular pitch of the housing teeth. For example, as shown in 990 of FIG. 9K, the pawl teeth 982 may be initially engaged with the second housing teeth 974. As shown in 992 of FIG. 9K, the pawl disc 980 may be moved axially downward relative to housing 972 so that the pawl teeth 982 engage with the first housing teeth 976 and the pawl disc 980 rotates a half step in the loosening direction. As shown in 994 of FIG. 9K, the pawl disc 980 may then be moved axially upward relative to housing 972 so that the pawl teeth 982 reengage with the second housing teeth 974 and the pawl disc 980 again rotates a half step in the loosening direction.

The pawl disc 980 may be moved axially downward and/or upward by pressing on and releasing the reel assembly's knob (not shown). Further, the pawl disc 980 may be biased toward the second housing teeth level 974 so that upon release of the reel assembly's knob, the pawl disc 980 automatically adjust axially upward into engagement with the second housing teeth level 974. In this manner, a user may effectuate incremental loosening of the lace tension by repeatedly pressing on the reel assembly's knob.

In some embodiments, incremental loosening of lace tension can be achieved via the lace guides rather than or in addition using the reel assembly. For example, the lace guides may be adjusted so as to incrementally decrease the tension on the lace, or the system may include an additional component that may be adjusted to incrementally loosen the tension on the lace. FIGS. 10A-11I illustrate various embodiments of lace guides that may be used to incrementally loosen tension on the lace.

Figure 10A:
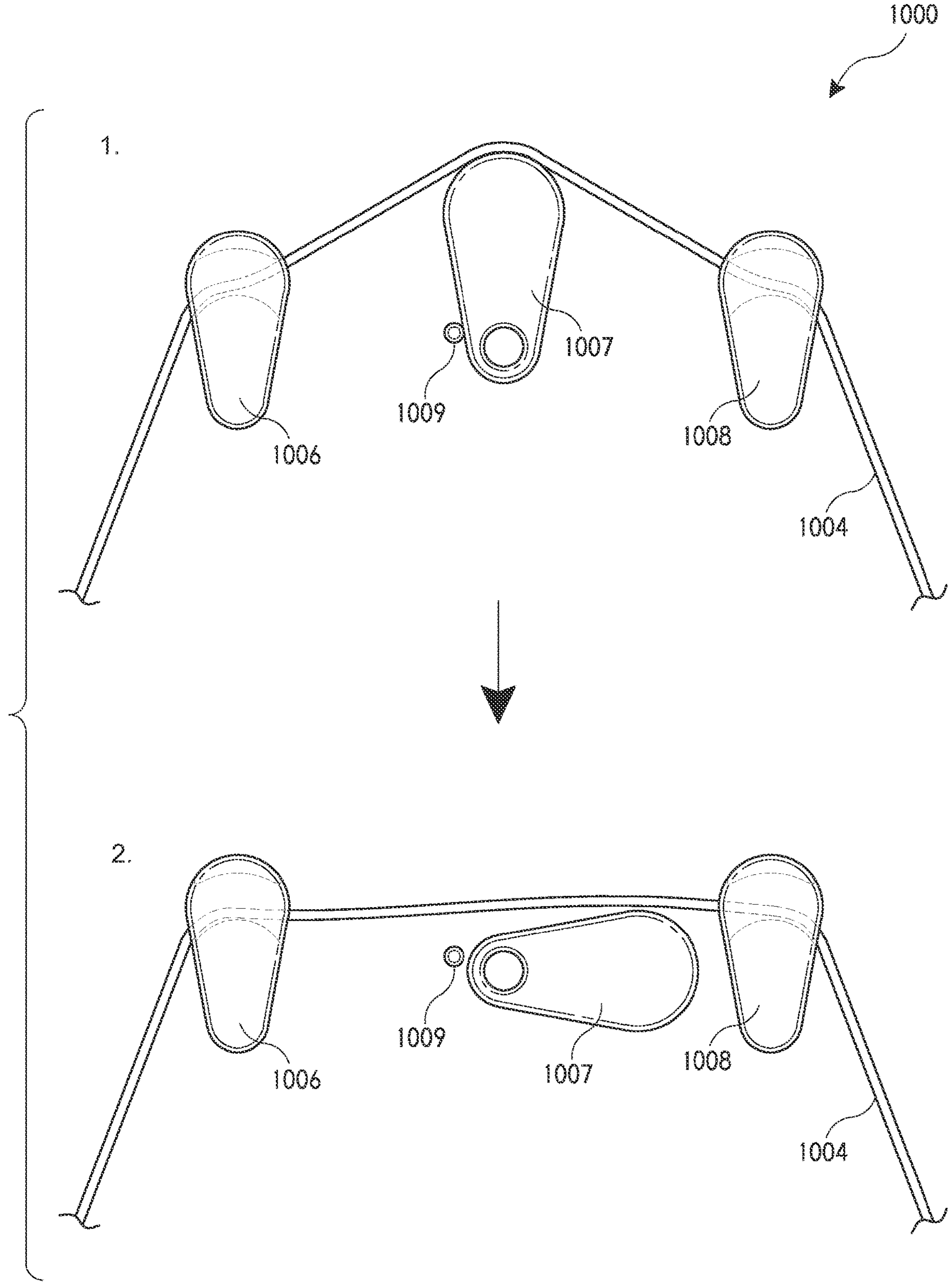
FIGS. 10A-C illustrate an embodiment of a tension member guide that is moveable into and out of a path of a tension member to respectively increase or loosen the tension member's tension.
Figure 10B:
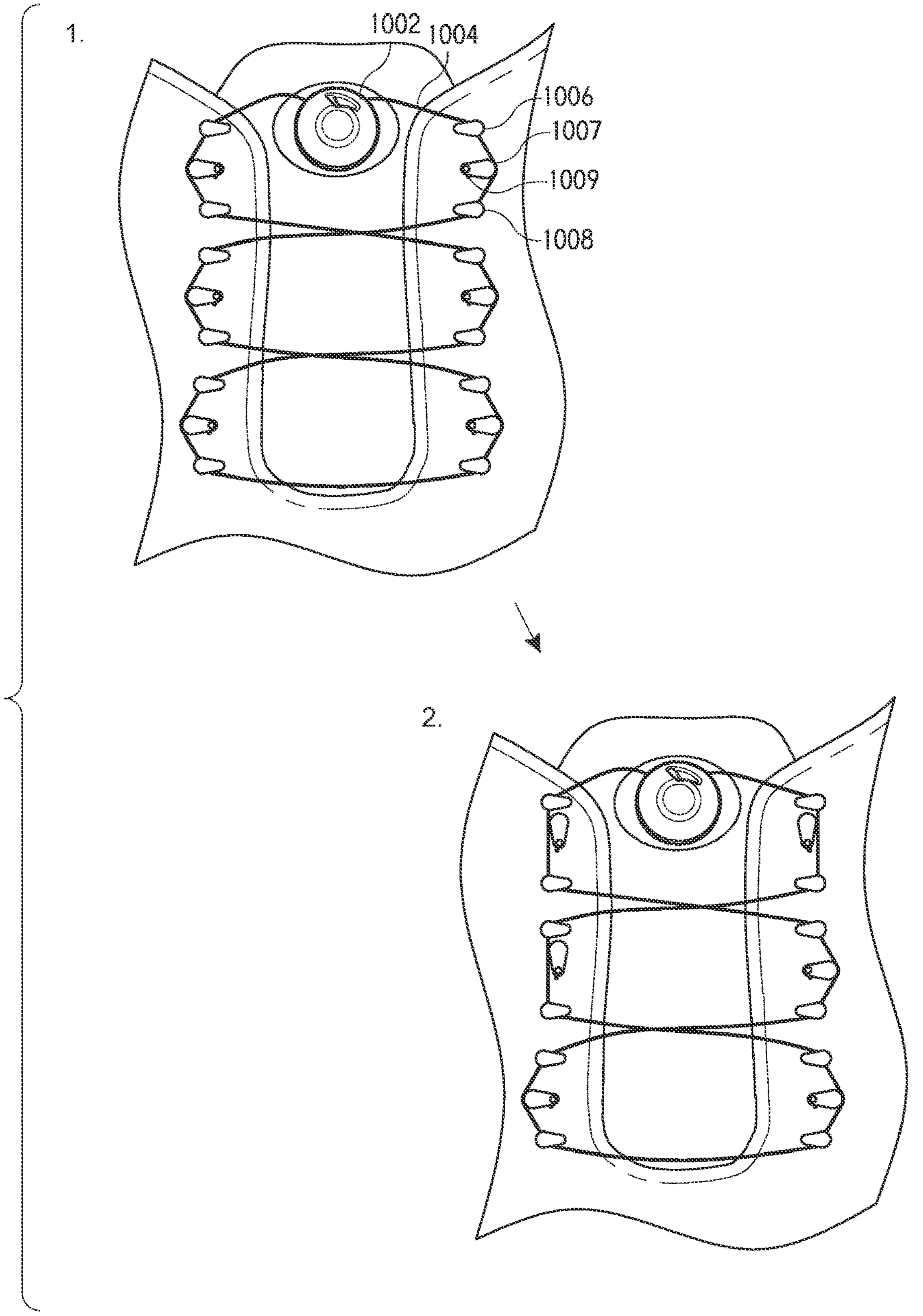
Figure 10C:
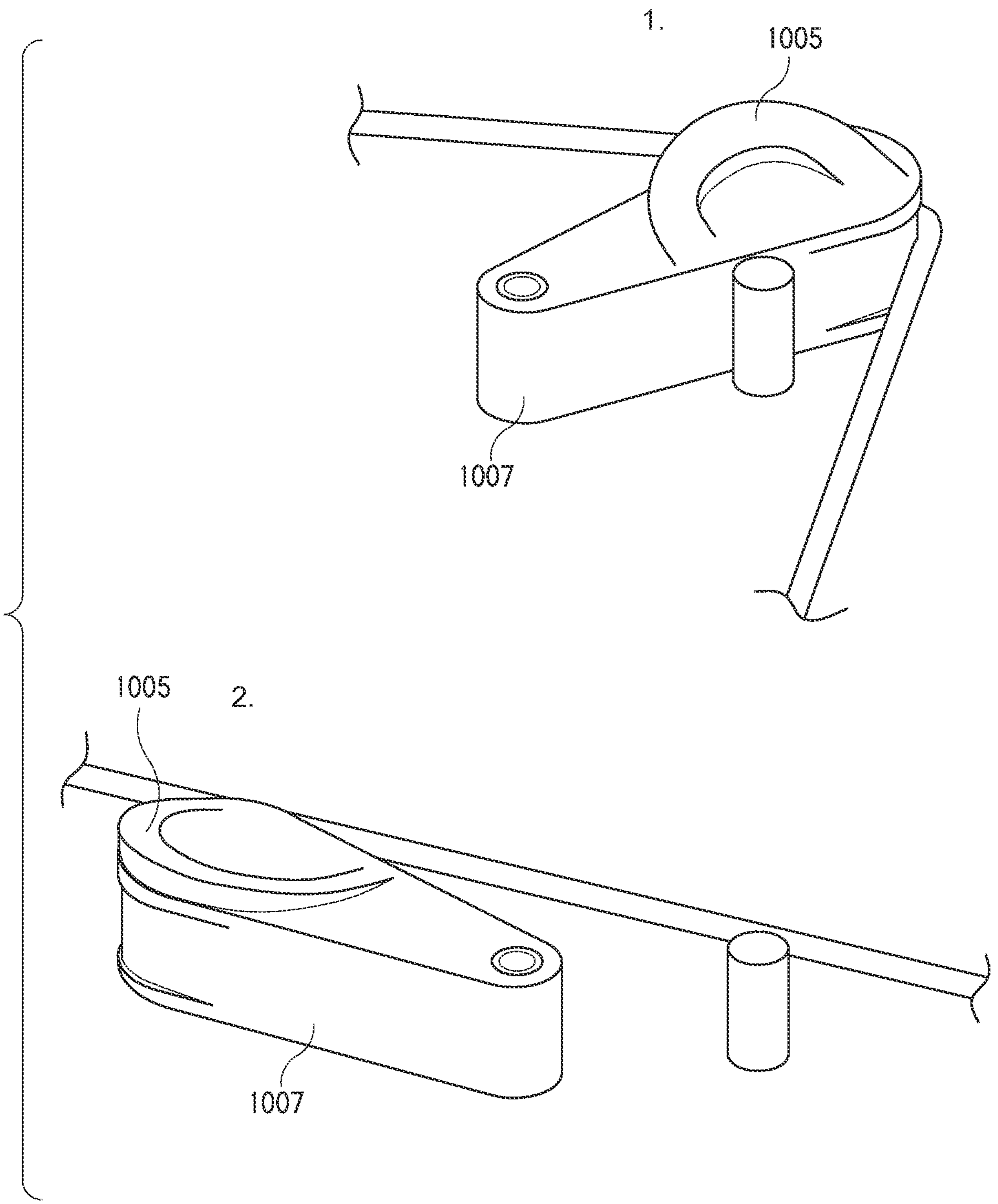

Referring now to FIGS. 10A-C, illustrated is an embodiment in which a guide 1007 is used to incrementally loosen tension on the lace. Specifically, the lacing system 1000 includes a reel assembly 1002 that is operated as described herein to tension lace 1004. The lace 1004 is wound around a plurality of guides (i.e., guides 1006, 1007, and 1008) that direct the lace 1000 along a lace path of the lacing system 1000. The lacing system 1000 includes a plurality of guide systems positioned longitudinally along the lace path. Each guide system includes a first end guide 1006, a second end guide 1008, and an intermediate guide 1007 that is positioned between the first end guide 1006 and the second end guide 1008. Each guide system redirects the lace 1004 from a first direction to a second direction.

The intermediate guide 1007 is adjustable so as to incrementally loosen the tension on the lace by varying the lace path of the guide system. The intermediate guide 1007 functions similar to a cam component to engage and disengage the lace 1004 and thereby affect the lace path and tension. For example, the intermediate guide 1007 may pivot between a first position (i.e., 1 of FIGS. 10A-C) in which the intermediate guide 1007 engages the lace 1004 and a second position (i.e., 2 of FIGS. 10A-C) in which the intermediate guide 1007 disengages the lace 1004. Because the intermediate guide 1007 engages the lace 1004 in the first position, the overall lace path is longer and the tension in the lace 1004 is increased as the lace 1004 slightly stretches and/or the laced article (e.g., a shoe) is closed more tightly. Similarly, because the intermediate guide 1007 does not engage the lace 1004 in the second position, the overall lace path is shorter and the tension in the lace 1004 is decreased as the lace 1004 relaxes and/or the laced article (e.g., a shoe) is slightly opened. The above scenario assumes that the overall lace length in the system remains unchanged. Stated differently, the above scenario assumes that no lace is added or removed as the intermediate guide 1107 is adjusted.

In some embodiments, the intermediate guide 1007 may engage a stop member 1009 when the intermediate guide 1007 is positioned in the first position. The stop member 1009 may prevent the intermediate guide 1007 from rotating out of the first position, in which the intermediate guide 1007 engages the lace 1004. The intermediate guide 1007 may also be positioned such that the pressure exerted on the intermediate guide 1007 from the lace 1004 presses or maintains the intermediate guide 1007 in contact or engagement with the stop member 1009. For example, the intermediate guide 1007 may be positioned slightly off center from a pivot of the intermediate guide 1007 such that the lace tension biases the intermediate guide 1007 to rotate toward and/or into engagement with the stop member 1009. Since the intermediate guide 1007 is biased slightly toward the stop member 1009, rotation of the intermediate guide 1007 away from the stop member 1009 may cause the tension in the lace to slightly increase before the intermediate guide 1007 is disengaged from the lace 1004 to decrease the lace tension.

In some embodiments, the intermediate guide 1007 may include a tab 1005 that is grippable by a user to aid in rotating the intermediate guide 1007 away from the stop member 1009. For example, the tab 1005 may allow a user to easily place a thumb or finger atop the intermediate guide 1007 and rotate the intermediate guide 1007 away from the stop member 1009. In some embodiments, the intermediate guide 1007 may include an internal spring (not shown) that biases the intermediate guide 1007 toward the stop member 1009 when tension is loosened from the lace 1004. In such embodiments, when the tension on the lace 1004 is fully loosened or released, the internal spring may cause the intermediate guide 1007 to pivot into engagement with the stop member 1009. As such, upon fully releasing the lace tension, the intermediate guides 1007 of the lacing system 1000 may return to the first position so that upon re-tensioning of the lace 1004 via reel assembly 1002, the intermediate guides 1007 may be used to incrementally loosen the lace 1004.

Although the guide systems in the embodiment of FIGS. 10A-C have been generally described as each including an intermediate guide 1007, in some embodiments one or more of the guide systems may not include an intermediate guide 1007. For example, guide systems positioned closer to a user's toe may not include an intermediate guide 1007 while guide systems positioned closer to the user's ankle or heel do include the intermediate guides. Such systems may allow the user to easily adjust the lace tension by placing the intermediate guides 1007 in areas that are more easily accessible to the user.

Figure 10D:
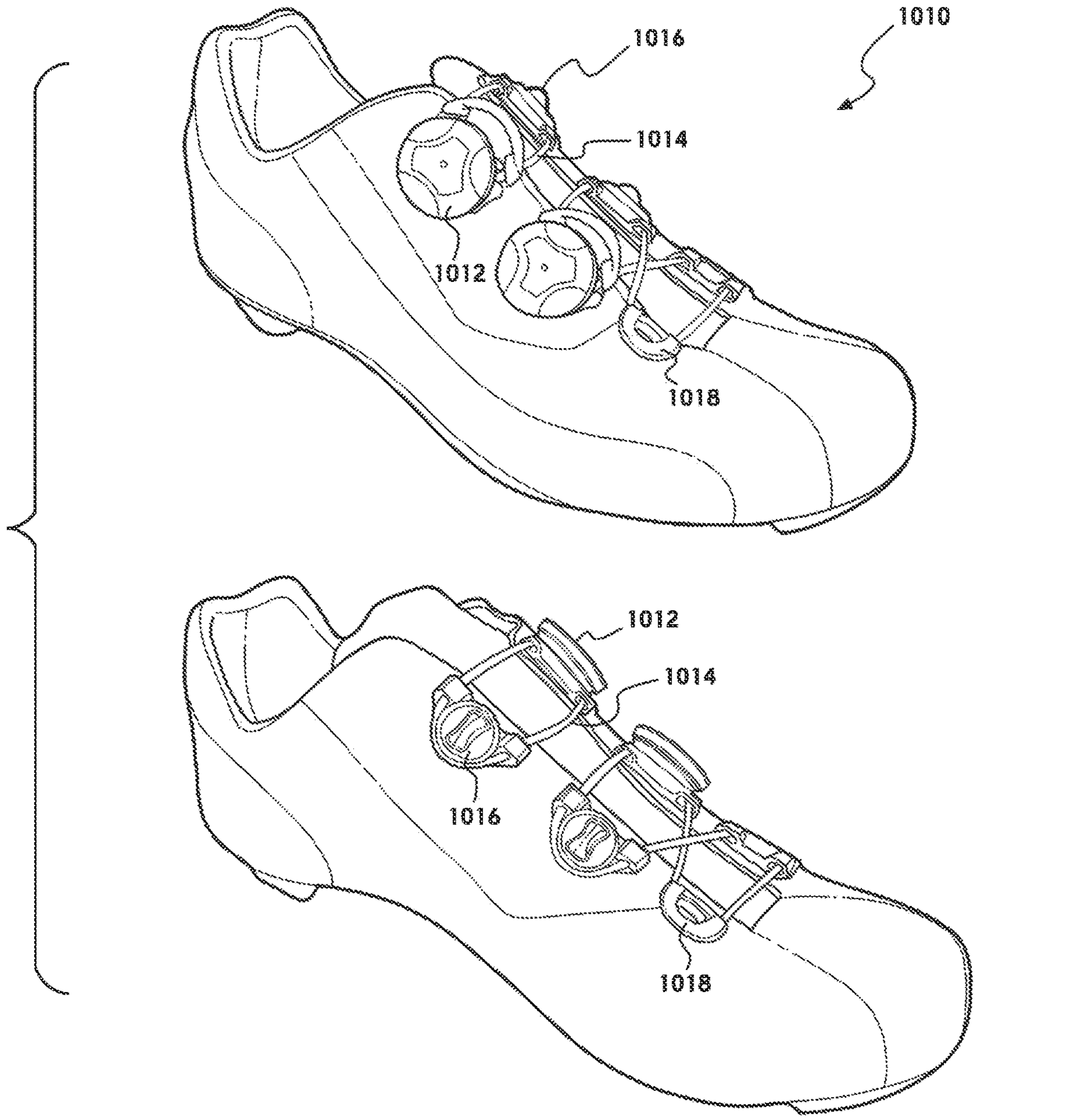
FIGS. 10D-E illustrate another embodiment of a tension member guide that is adjustable to alter the tension member's path to increase or loosen the tension member's tension.
Figure 10E:
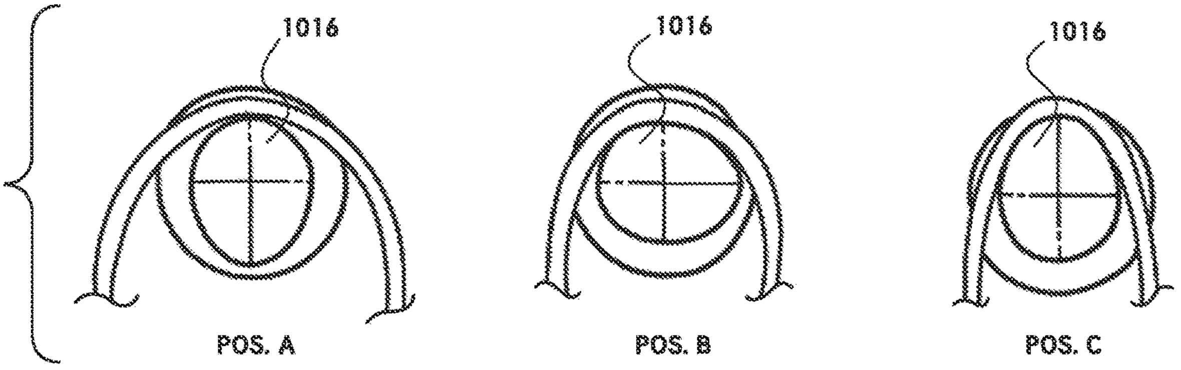

Referring now to FIGS. 10D and 10E, illustrated is another embodiment of the lacing system 1010 that includes an adjustable guide 1016 that may be used to incrementally loosen tension on the lace. The lacing system 1010 includes one or more of the adjustable guides 1016 and/or one or more reel assemblies 1012. As shown in FIGS. 10D and 10E, the adjustable guides 1016 may be positioned laterally across from a reel assembly 1012 and/or may include one or more non-adjustable lace guides 1018. In other embodiments, lacing system 1010 may include a single reel assembly 1012 and a combination of adjustable guides 1016 and/or non-adjustable guides 1018.

In some embodiments, the adjustable guide 1016 may have a non-circular profile or surface (e.g., oblong or oval configuration) such that rotation of the adjustable guide 1016 relative to the lace 1014 alters the lace path by affecting the contact or engagement of the guide 1016 with the lace 1014. In this manner, the guide 1016 may function similar to a cam component to affect the lace path and tension. For example, in a first position (position C), the adjustable guide 1016 may be rotated such that a large area or cam surface of the adjustable guide 1016 engages or contacts the lace 1014 and increases the lace path. Stated differently, the adjustable guide 1016 may engage the lace 1014 by a maximum amount. In this position (i.e., position C), the path of the lace 1014 may be fully extended so that the tension on the lace 1014 is at or near a maximum tension.

To decrease the tension on the lace, the adjustable guide 1016 may be rotated to a second position (position B), such that a smaller area or cam surface of the adjustable guide 1016 engages or contacts the lace 1014, or stated differently, so that the adjustable guide 1016 engages the lace 1014 by an amount less than position C. In this position (i.e., position B), the path of the lace 1014 may be decreased compared with position C so that the tension on the lace 1014 is decreased. To further decrease the tension on the lace, the adjustable guide 1016 may again be rotated to a third position (position A), such that a smallest cam area or surface of the adjustable guide 1016 engages or contacts the lace 1014. Stated differently, the adjustable guide 1016 may engage the lace 1014 by a minimal amount. In this position (i.e., position A), the path of the lace 1014 may be minimal so that the tension on the lace 1014 is at or near a minimum tension. When multiple adjustable guides 1016 are used in the lacing system 1010, each guide 1016 may be adjusted between positions A-C to vary the overall tension in the lace 1014.

Referring now to FIGS. 11A-I, illustrated are embodiments in which a guide component moves laterally along a track to incrementally decrease tension in the lace. For example, FIGS. 11A-D illustrate a guide 1102 having entrance and exit ports 1103 for the lacing system's lace as described herein. The guide 1102 is configured to move laterally along a track 1104, which is positioned laterally across a shoe or other article being tightened with the lacing system. The track 1004 includes teeth that engage with corresponding teeth 1112 of an internal ratchet component 1110 of the guide 1102. The engagement of the teeth of track 1104 and internal ratchet component 1110 allows the guide 1102 to incrementally move along the track 1104. Specifically, the ratchet component 1110 is positioned within a lumen of the guide 1102 such that the ratchet component 1110 is able to rotate within the lumen. Rotation of the ratchet component 1110 within the lumen of guide 1102 allows the ratchet component's teeth 1112 to engage with and move along the teeth of the track 1104 in a rack and pinion like manner. Movement of the ratchet component 1110 along the track 1104 in this manner enables the guide 1102 to move laterally along the track 1104.

Rotation of the ratchet component 1110 within the lumen is controlled via a pair of stop clutches 1106 that are positioned within the guide's lumen on opposing ends of the ratchet component 1110. The stop clutches 1106 control the rotation of the ratchet component 1110 in order to control the movement of the guide 1102 along the track 1104. The stop clutches 1106 are prevented from rotation within the guide's lumen via an interaction between the stop clutches' teeth 1122 and corresponding teeth 1128 positioned within the lumen of guide 1102. The stop clutches 1106 also include a plurality of axially arranged blocks 1124 that engage with corresponding blocks 1114 of the ratchet component 1110 to prevent rotation of the ratchet component 1110 within the lumen when the teeth 1122 of clutch 1106 disengage from the teeth 1128 of guide 1102.

To control rotation of the ratchet component 1110 when the teeth 1122 of clutch 1106 disengage from the teeth 1128 of guide 1102, the blocks 1124 of the stop clutches 1106 are arranged with a first level of blocks 1124*b* and a second axial level of blocks 1124*a* that are positioned axially inward of and circumferentially offset from the first level of blocks 1124*b*. The stop clutches 1106 are positioned within the lumen of the guide 1102 such that the second level of blocks 1124*a* initially engage the ratchet component's blocks 1114. The stop clutches 1106 may then be pressed axially inward within the lumen of guide 1102 such that the teeth 1122 of clutch 1106 disengage from the teeth 1128 of guide 1102 and the ratchet component's blocks 1114 slide out of engagement with the second level of blocks 1124*a* and into engagement with the first level of blocks 1124*b* positioned axially outward from the second level of blocks. Since the first level of blocks 1124*b* are circumferentially offset from the second level of blocks 1124*a* and the teeth 1122 of the clutches 1106 are disengaged from the teeth 1128 of the guide 1102, the ratchet component 1110 is able to rotate within the lumen of guide 1102 until the ratchet component's blocks 1114 contact or engage with the first level of blocks 1124*b*. Engagement of the blocks 1114 with the first level of blocks 1124*b* prevents further rotation of the ratchet component 1110.

A spring component 1126 is positioned within the lumen of guide 1102 and between the stop clutches 1106. Spring component 1126 biases the stop clutches 1106 axially outward such that when the stop clutches 1106 are released, the stop clutches 1106 slide axially outward relative to ratchet component 1110. The axially outward movement of the stop clutches 1106 causes the ratchet component's blocks 1114 to slide out of engagement with the first level of blocks 1124*b* and into engagement with the second level of blocks 1124*a* and causes the teeth 1122 of the clutches 1106 to reengage with the teeth 1128 of the guide 1102. As described above, since the second level of blocks 1124*a* are circumferentially offset from the first level of blocks 1124*b*, the ratchet component 1110 is able to rotate within the lumen of guide 1102 until the ratchet component's blocks 1114 contact or engage with the second level of blocks 1124*a*. In this manner, the guide 1102 is able to move incrementally along track 1104 each time the stop clutches 1106 are pressed axially inward and released.

Movement of the guide 1102 along the track 1104 is caused in response to tension within the lace of lacing system 1100. Stated differently, tension in the lacing system's lace is what drives or causes rotation of the ratchet component 1110 within the lumen of guide 1102 as the stop clutches 1106 are pressed axially inward and released. As such, when the lease tension is at or near a zero tension level, inward pressing of the stop clutches 1106 will not cause the ratchet component 1110 to rotate within the lumen of guide 1102 and/or cause incremental movement of the guide 1102 along the track 1104.

In some embodiments, guide 1102 may include a spring 1108 that is coupled with the shoe or other apparel and that biases the guide 1102 toward a distal end of the track 1104. In such embodiments, guide 1102 may automatically return to the distal end of track 1104 when the tension in the lace is fully loosened. To facilitate distal movement of the guide 1102 along the track 1104, the ratchet component's teeth 1112 and the teeth of track 1104 may be configured so as to prevent tooth engagement, or to allow the teeth to skip over one another, as the guide 1102 moves distally along the track 1104. In this manner, when the lace tension is loosened or released from lacing system 1100, the guide 1102 may be reset at a distal end of the track 1104 so that upon re-tensioning of the lace, the stop clutches 1106 may be operated to incrementally loosen the tension on the lace.

Figure 11A:
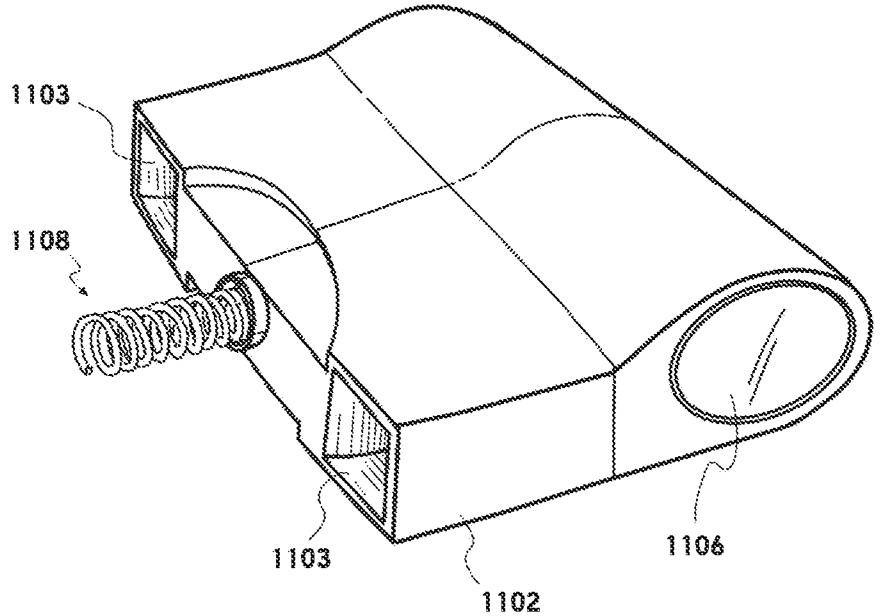
FIGS. 11A-D illustrate an embodiment of a tension member guide having a button system that enables the tension member guide to move along a track to loosen the tension member's tension.
Figure 11B:
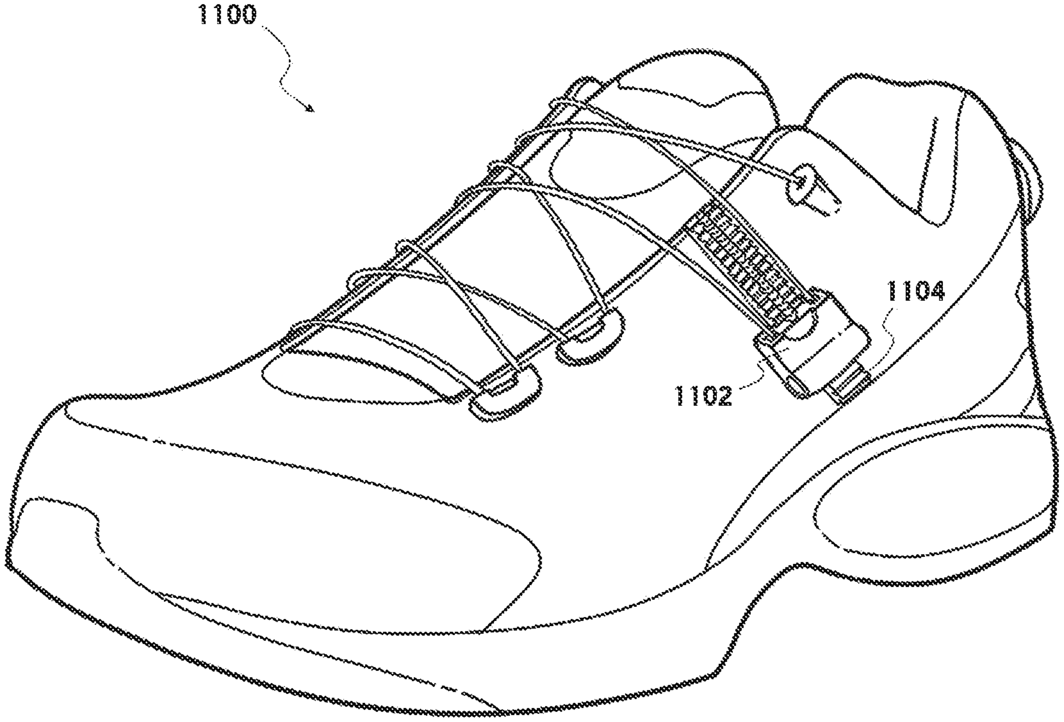
Figure 11C:
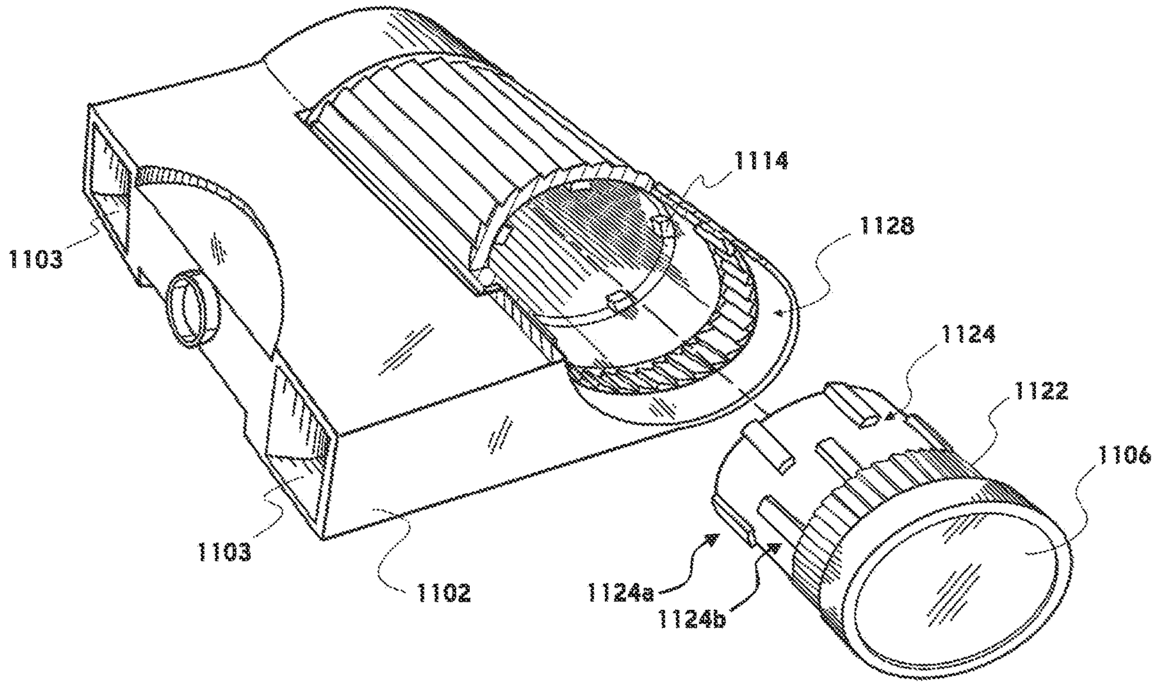
Figure 11D:
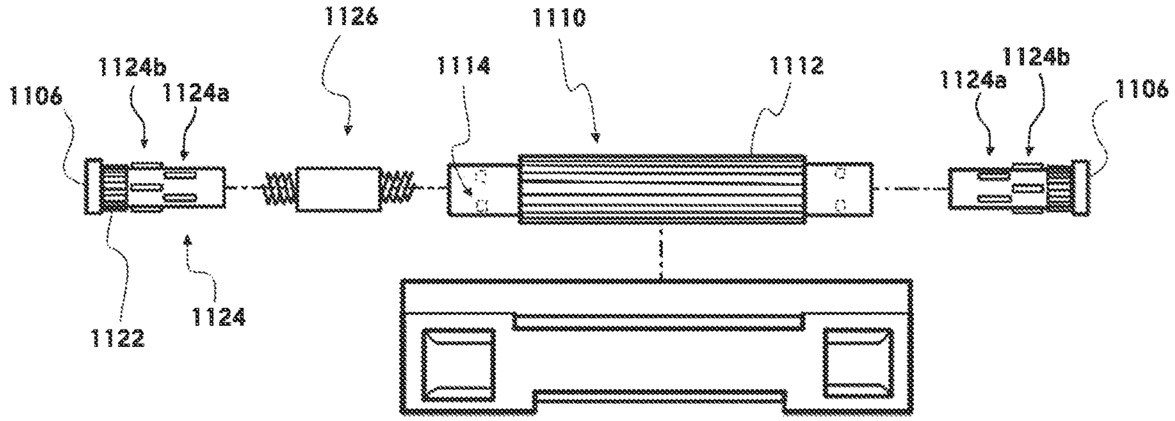
Figure 11E:
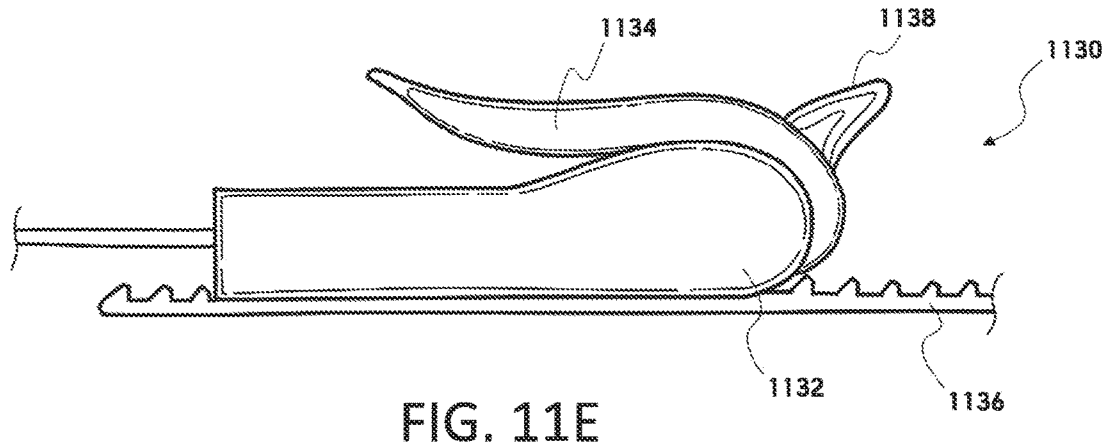
FIGS. 11E-G illustrate an embodiment of a tension member guide having a lever or arm that is operable to move the tension member guide along a track to loosen the tension member's tension.
Figure 11F:
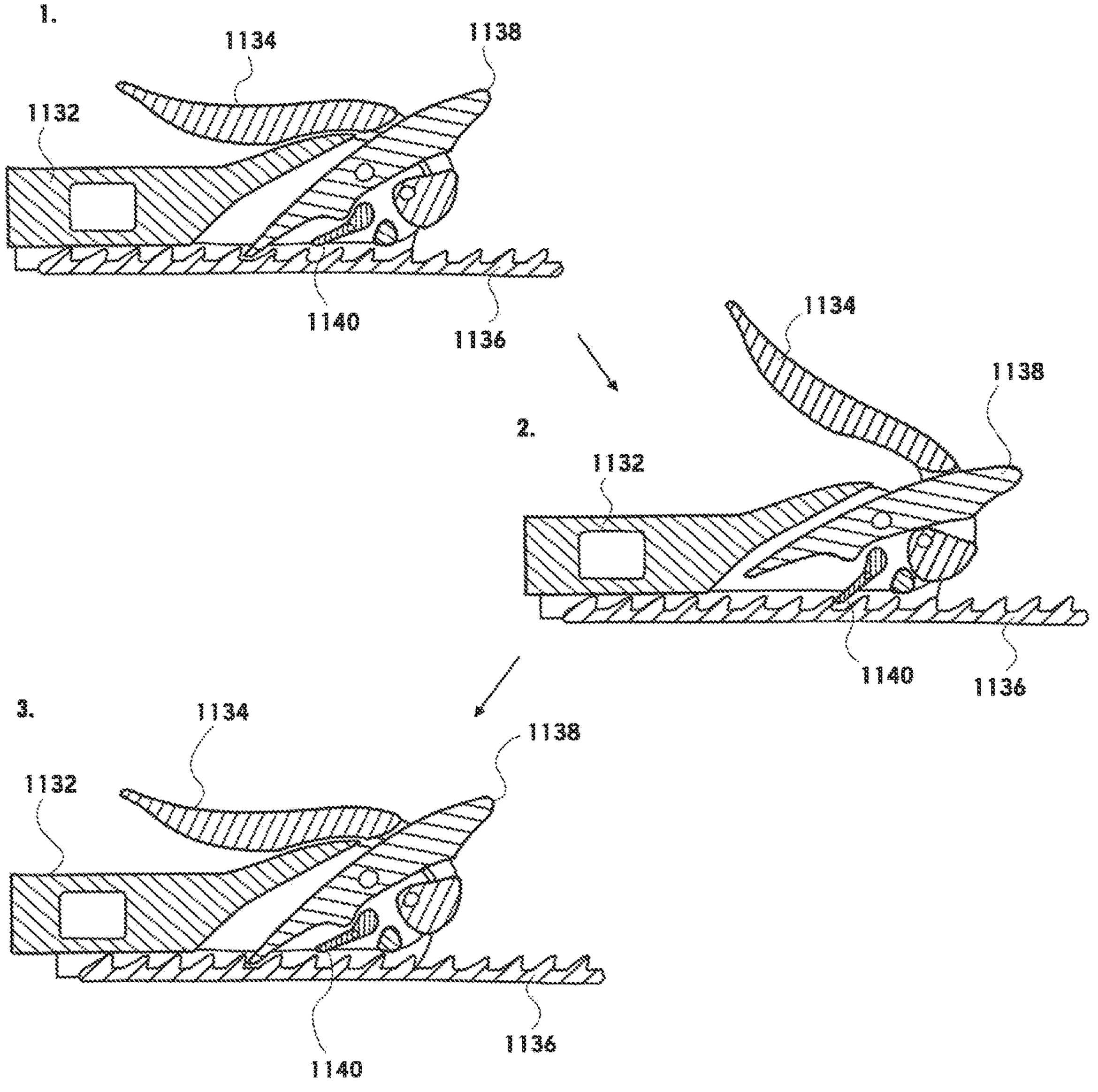
Figure 11G:
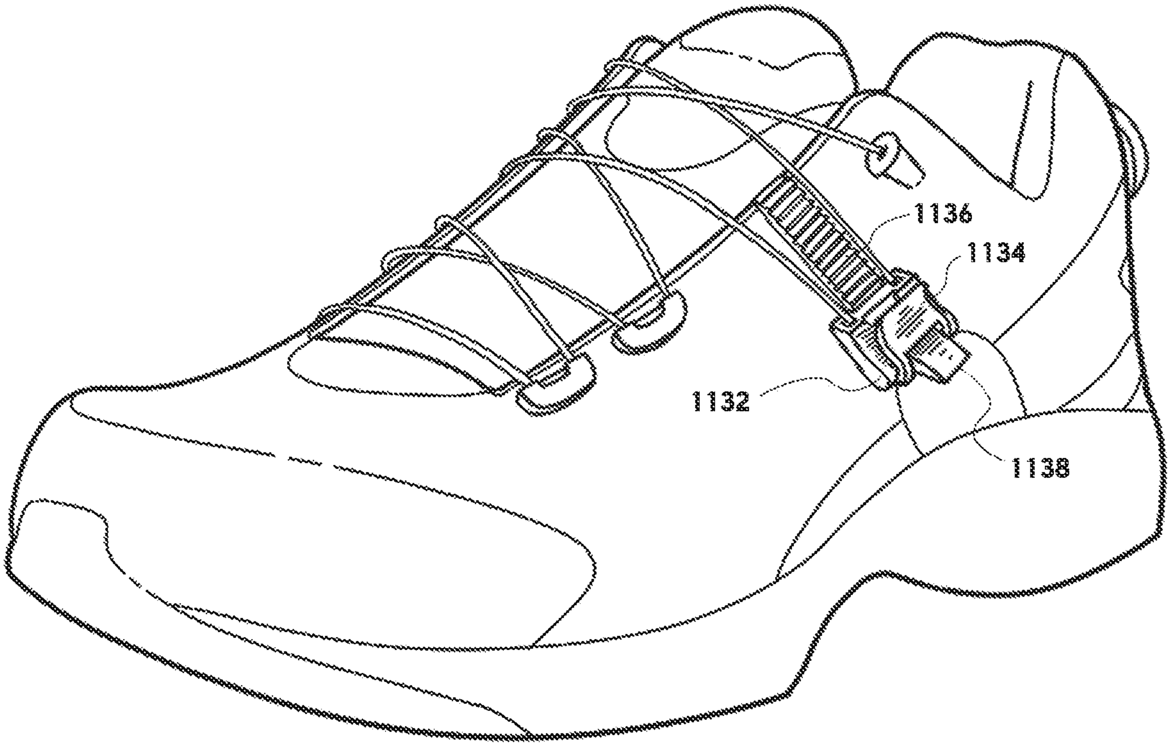

Referring now to FIGS. 11E-G, illustrated is another embodiment of a guide 1132 that is configured move laterally along a track 1136 in order to incrementally loosen or decrease the lace tension. The embodiment of FIGS. 11E-G is similar to FIGS. 11A-D in that the lace tension drives or causes proximal movement of the guide 1132 along the teeth of the track 1136. To effect proximal movement of the guide 1132, the guide 1132 include a pull tab 1134 that may be pulled by a user. The pull tab 1134 is connected to a first tooth 1138 that is initially engaged with a tooth of the track 1136 to prevent movement of the guide 1132 along the track 1136. As shown in FIG. 11F, pulling the tab 1134 causes the first tooth 1138 to disengage from the teeth of track 1136, such as by causing the tooth 1138 to rotate out of engagement with the tooth. The pull tab 1134 simultaneously causes a second tooth 1140 to rotate into position within track 1136 so that upon proximal movement of the guide 1132 (via tension in the lacing system 1130's lace), the second tooth 1140 engages with the teeth of track 1136.

The pull tab 1134 may then be released by the user to disengage the second tooth 1140 from engagement with the teeth of the track 1136, such as by rotating the second tooth 1140 out of engagement with the track's teeth. Releasing the pull tab 1134 may simultaneously reengage the first tooth 1138 with the track so that upon proximal movement of the guide 1132 via lace tension, the first tooth 1138 reengages with the teeth of track 1136. In this manner, the guide 1132 may be incrementally moved along the track 1136 to loosen the tension in the lacing system 1130's lace. In some embodiments, the first tooth 1138 and second tooth 1140 may be arranged approximately ½ step offset from one another so that pulling and releasing the tab 1134 cause the guide 1132 to move proximally one step (i.e., one tooth) along the track 1136.

In some embodiments the guide 1132 may include a spring component (not shown) that is configured to bias the guide 1132 distally along the track 1136 such that upon fully releasing the tension in the lace, the guide 1132 moves automatically to a distal end of the track 1136. In some embodiments, a distal end of the first tooth 1138 may be pressed to rotate the first and second teeth, 1138 and 1140, into and out of engagement with the track 1136 rather than, or in addition to, pulling on tab 1134.

Figure 11H:
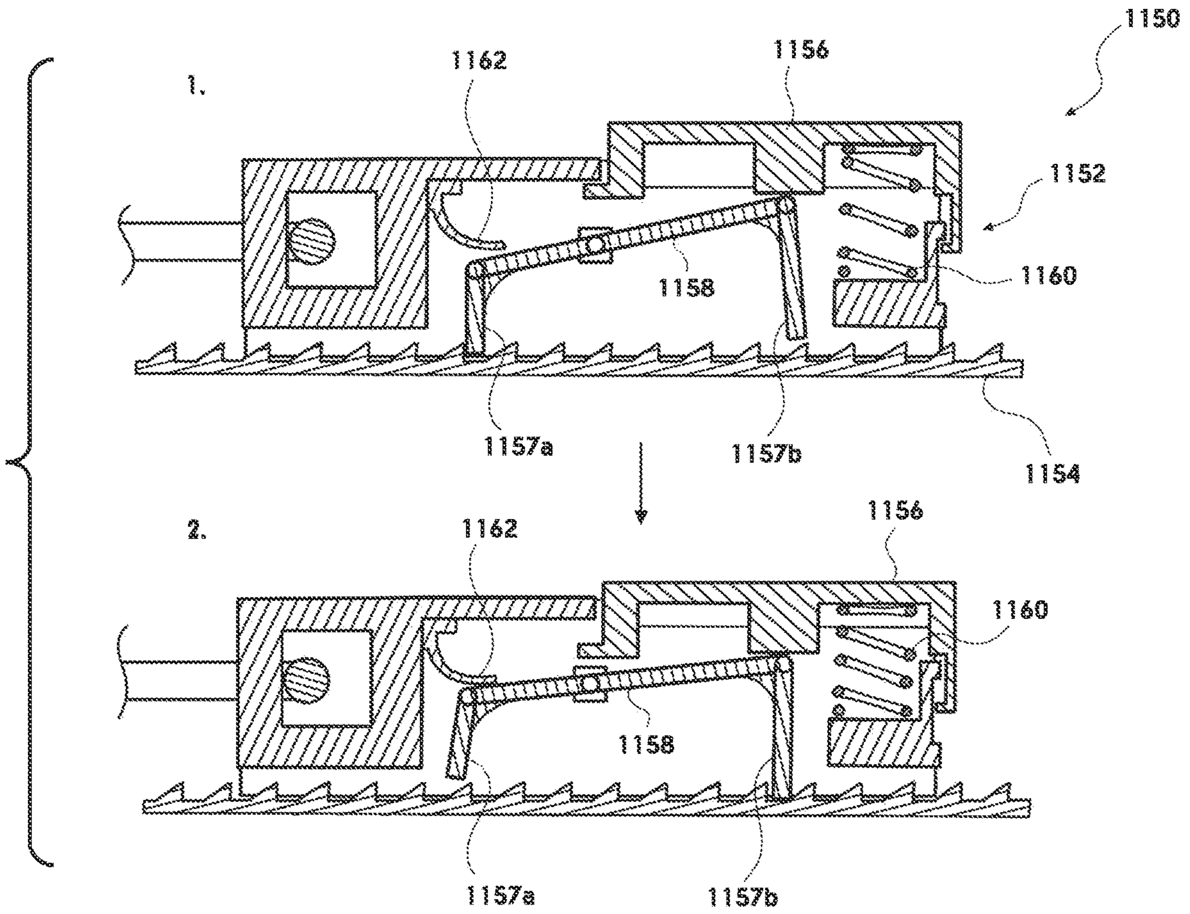
FIGS. 11H-I illustrate an embodiment of a tension member guide having a button system that is operable to move the tension member guide along a track to loosen the tension member's tension.
Figure 11I:
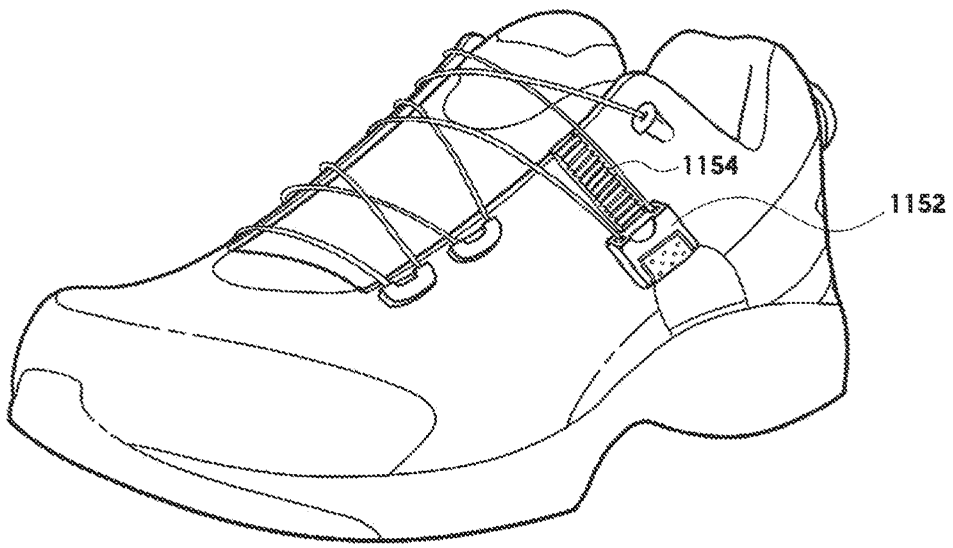

Referring now to FIGS. 11H and 11I, illustrated is another embodiment of a guide 1152 that is configured to move laterally along a track 1154 to incrementally loosen or decrease tension in the lacing system 1150's lace. The guide 1152 includes a button 1156 that may be pressed by a user to effectuate proximal movement of the guide 1152 along the track 1154. The guide 1152 includes an internal pivot mechanism 1158 having a first locking arm 1157*a* and a second locking arm 1157*b* that are positioned on opposing ends of a central pivoting member or arm. In an initial locked positioned, the first locking arm 1157*a* may be engaged with a tooth of the track 1154 so as to prevent proximal movement of the guide 1152 along the track 1154.

Pressing the button 1156 downward causes the button 1156 to contact the second locking arm 1157*b*, which causes the central pivoting arm to pivot within the guide 1152. Pivoting of the central pivot arm allows some proximal movement of the guide 1152 along the track 1154 by causing the first locking arm 1157*a* to pivot out of engagement with the teeth of track 1154 while the second locking arm 1157*b* pivots into engagement with the teeth. A first spring component 1160 is positioned within the guide and in contact with the button 1156 such that upon releasing the button 1156, the first spring component 1160 biases the button 1156 out of contact with the second locking arm 1157*b*. A second spring component 1162 is also positioned within the guide 1152 and in contact with the first locking arm 1157*a* such that upon releasing the button 1156, the second spring component 1162 presses on the first locking arm 1157*a* to cause the second locking arm 1157*b* to pivot out of engagement with the teeth of track 1154 while the first locking arm 1157*a* pivots into engagement with the teeth after some proximal movement of the guide 1152 along the track 1154. In this manner, the guide 1152 may move proximally along the track 1154 in incremental steps as the button 1156 is pressed and released by a user.

As with the previous embodiments, the guide 1152 may include a spring component (not shown) that is configured to bias the guide 1152 distally along the track 1154 such that upon fully releasing the tension in the lace, the guide 1152 automatically moves to a distal end of the track 1154. In such embodiments, upon re-tensioning of the lace, the button 1156 may then be used to incrementally loosen the lace tension.

According to one embodiment, a method for configuring a reel for use with a lacing system for tightening an article may include providing a housing having an interior region and positioning a spool within the interior region of the housing so that the spool is rotatable relative to the housing. The spool may have an annular channel formed therein. The method may also include operably coupling a knob with the spool to cause the spool to rotate within the interior region of the housing upon rotation of the knob. The knob may be rotatable relative to the housing so that 1) incremental rotation of the knob in a first direction causes a corresponding incremental rotation of the spool within the interior region of the housing that incrementally gathers a tension member in the annular channel formed in the spool and 2) incremental rotation of the knob in a second direction causes a corresponding incremental rotation of the spool that incrementally releases the tension member from the annular channel formed in the spool. The method may also include configuring the reel with a stop mechanism that is configured to prevent rotation of the spool in the second direction when a tension of the lace achieves or decreases beyond a tension threshold.

In some embodiments, the stop mechanism may be configured to engage only when the tension of the lace achieves or decreases beyond the tension threshold and engagement of the stop mechanism may prevent the spool from rotating in the second direction. In some embodiments, the spool may be axially moveable within the interior region of the housing and axial movement of the spool within the interior region may effect engagement and disengagement of the stop mechanism. In some embodiments, the stop mechanism is moveable between an engaged state and a disengaged state. In such embodiments, the stop mechanism may be configured to move into the engaged state only when the tension of the lace achieves or decreases beyond the tension threshold and may be configured to move into the disengaged state upon rotation of the knob in the first direction.

In some embodiments, the stop mechanism includes teeth, a rubber gasket, an abrasive material, a tacky material, and the like. In a specific embodiment, the stop mechanism includes a first set of teeth that are positioned on a bottom surface of the interior region of the housing and a second set of teeth that are positioned on a bottom flange of the spool. In such an embodiment, the spool is axially moveable within the interior region of the housing so that when the lace tension achieves or decreases beyond the tension threshold, the spool moves axially downward within the interior region of the housing to engage the first set of teeth and the second set of teeth and thereby prevent rotation of the spool in the second direction.

In some embodiments, the method further includes configuring the reel with a release mechanism that, upon actuation, enables the tension member to be automatically released from the annular channel formed in the spool by allowing free rotation of the spool in the second direction.

In another embodiment a closure system or reel assembly may provide incremental loosening of lace tension by displacing axially oriented teeth from corresponding teeth that are fixedly coupled with the housing. In such embodiments, the teeth that are fixedly coupled with the housing may be arranged on a disc or other component that is attachable to the housing, or may be integrated into the housing. The closure system or reel assembly may also provide a full release or lace tension loosening mechanism. In such embodiments, the closure system may include a housing having an interior region and a spool that is positioned within the interior region of the housing and rotatable relative thereto. A tension member may be coupled with the spool. A tensioning mechanism having a knob may be configured to effect tensioning of the tension member by winding the tension member around the spool upon rotation of the knob. An incremental release component may be operationally coupled with the spool. The incremental release component may have one or more axially oriented teeth that engage with corresponding teeth of a toothed disc that is attachable to the housing. The incremental release component may be configured to effect incremental tensioning of the tension member upon rotation of the knob in a first direction by engaging the axially oriented teeth. Engagement of the axially oriented teeth may allow the spool to rotate in a first direction while preventing rotation of the spool in a second direction. The incremental release component may also be configured to effect incremental loosening of the tension member's tension upon rotation of the knob in a second direction by disengaging the axially oriented teeth. Disengagement of the axially oriented teeth may allow the spool to rotate in a second direction by an incremental amount. The closure system may also include a full release mechanism that is transitionable between an engaged state and a disengaged state. When the full release mechanism is in the engaged state, the tension member's tension may be incrementally tensioned or loosened upon said rotation of the knob. When the full release mechanism is in the disengaged state, the tension member's tension may be automatically loosened.

In some embodiments, the full release mechanism may be transitionable between the engaged state and the disengaged state upon operation of a lever, button, or release component. In such embodiments, operation of the lever, button, or release component may move the spool axially downward within the housing's interior region and out of engagement with the incremental release component. In other embodiments, the full release mechanism may be transitionable between the engaged state and the disengaged state upon the knob being moved axially upward relative to the housing. In such embodiments, moving the knob axially upward relative to the housing may disengage the spool and the incremental release component.

Figure 12A:
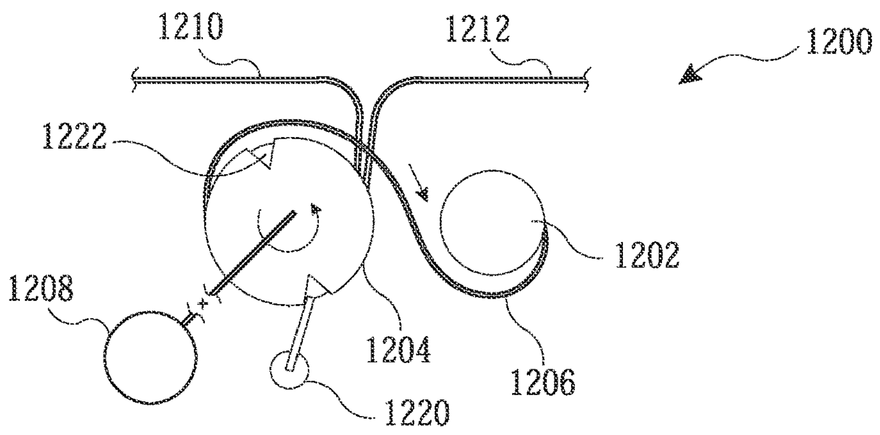
FIGS. 12A-C illustrate an embodiment of a mechanism that may be used with a tensioning device to hold or maintain an article in an open configuration.
Figure 12B:
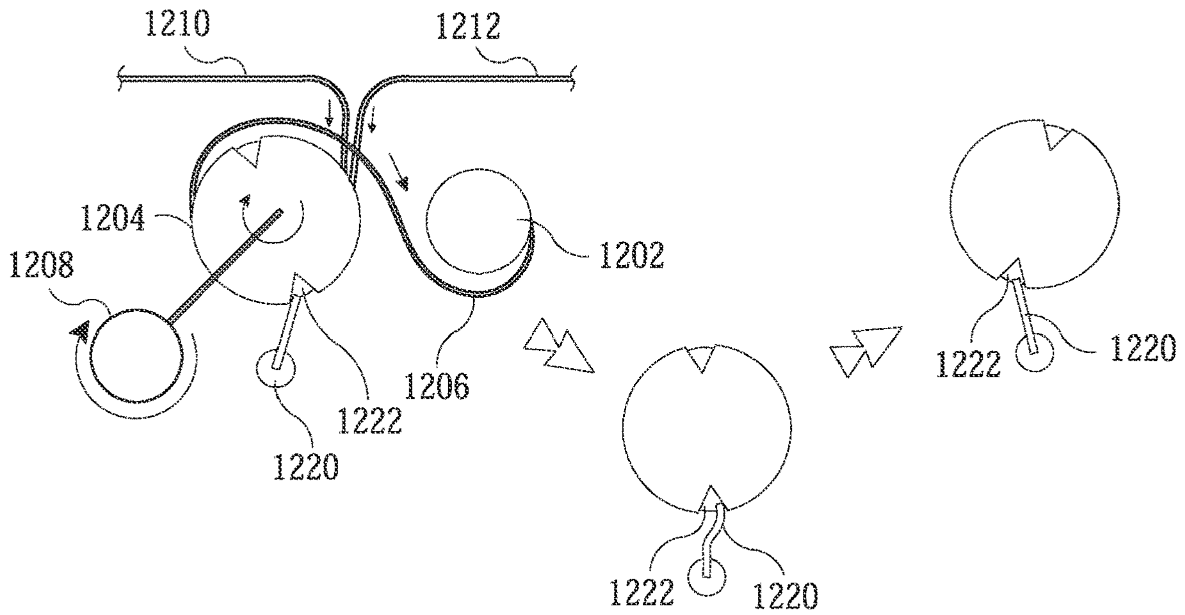
Figure 12C:
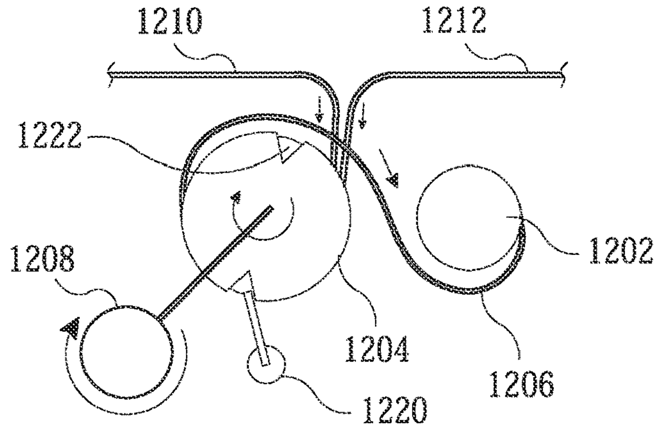

Referring now to FIGS. 12A-C, illustrated is an embodiment of a mechanism that may be used with a tensioning device to hold or maintain a shoe, brace, or other apparel in an open configuration. For example, the mechanism may find particular usefulness in shoes where a user desires to open opposing eyestays of the shoe and maintain the eyestays in an open configuration until the shoe is fit about the user's foot. The mechanism of FIGS. 12A-C may be particularly useful for secondary winding assemblies of tensioning devices that are used to quickly wind up lace, such as a motorized tensioning device or a manual based tensioning device that employs a spring (e.g., spiral torsion spring) that is configured to automatically rotate or wind the tensioning device's spool.

As shown in FIG. 12A, the mechanism 1200 includes a pawl 1220 or other member that is configured to catch and mechanically locked within a detent 1222 or recess of a spool 1204, such as the spools shown in the embodiments herein. The spool 1204 is coupled with a constant force spring 1202 via a spring component 1206. The constant force spring 1202 is configured to rapidly wind the spool 1204 via the spring component 1206. To prevent automatic winding of the spool 1204 via constant force spring 1202, the pawl 1220 engages with the detent 1222 and locks or maintains spool 1204 in position. This allows a first lace 1210 and/or second lace 1212 to remain relatively loose and/or un-tensioned, which aides in donning of the shoe about a foot. FIG. 12A shows the pawl 1220 being positioned in a rightward orientation relative to the spool 1204 and further shows the pawl 1220 positioned within the detent 1222 to prevent clockwise rotation of spool 1204 and thereby hold or maintain the spool 1204 in position. The rotational force exerted on spool 1204 via the constant force spring 1202 and the spring component 1206 is not sufficient to overcome the force imparted on the spool 1204 by the pawl 1220. Stated differently, the pawl 1220 counteracts rotation of the spool 1204 and as such, the spool 1204 remains stationary while the pawl 1220 is positioned in the rightward orientation.

After the shoe is donned and the user wishes to close and tighten the brace or shoe, the tensioning device is actuated to move the pawl 1220 into a disengaged position relative to the spool 1204 and the detent 1222. Specifically, as shown in FIG. 12B, the knob 1208 of the tensioning device, or a motor component of a motorized tensioning device, may be engaged to rotate the spool 1204 clockwise. The rotational force of the knob 1208 or motor is sufficient to cause the pawl 1220 to buckle within the detent 1222 or otherwise move relative thereto. As shown in FIG. 12B, buckling or moving of the pawl 1220 causes the pawl 1220 to shift or displace from the rightward orientation to a leftward orientation in which the pawl 1220 does not prevent clockwise rotation of the spool 1204. Rather, in the leftward orientation, the detent 1222 may cause the pawl 1220 to deflect as the spool 1204 is rotated in a tightening direction (e.g., clockwise). Movement of the pawl 1220 from the rightward orientation to the leftward orientation allows the constant force spring 1202 to quickly wind the spool 1204 via the spring component 1206, which allows the first lace 1210 and/or the second lace 1212 to be quickly wound around the spool 1204. Further tensioning of the first lace 1210 and/or second lace 1212 may be achieved via the knob 1208 or motor unit as described herein.

FIG. 12C illustrates the pawl 1220 in the leftward orientation relative to the spool 1204. FIG. 12C also illustrates the pawl 1220 being positioned within one of the detents 1222 in the leftward orientation. Positioning of the pawl 1220 within one of the detents 1222 may aid in preventing counter rotation of the spool 1204 (e.g., counterclockwise rotation of spool 1204). To unwind or loosen the first lace 1210 and/or the second lace 1212, the reverse of the above process may be performed. Specifically, the knob 1208 may be actuated to cause the spool 1204 to rotate in a loosening direction (e.g., counterclockwise), which causes the pawl 1220 to buckle or displace from the leftward orientation to the rightward orientation as shown in FIG. 12A. The first lace 1210 and/or the second lace 1212 may then be loosened via the knob/motor 1208 or via pulling open the eyestays of the shoe. The pawl 1220 then functions to maintain the shoe in an open configuration as described above.

Exemplary embodiments of constant force springs are further described in U.S. patent application Ser. No. 14/198,419, filed Mar. 5, 2014, entitled "Systems, Methods, and Devices for Automatic Closure of Medical Devices," and in U.S. patent application Ser. No. 14/228,075, filed Mar. 27, 2014, entitled "Reel Based Closure System," the entire disclosures of which are incorporated by reference herein.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the device" includes reference to one or more devices and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. A reel based closure device for tightening an article, the reel based closure device comprising:
- a housing having an interior region;
- a spool positioned within the interior region of the housing, the spool being rotatable in a first direction within the housing to wind a tension member about the spool and thereby tighten the article;
- a knob rotatably coupled with the housing and operably coupled with the spool to cause the spool to rotate within the housing in the first direction;
- a pawl that includes at least one pawl tooth and that is configured to prevent rotation of the spool in a second direction that is opposite of the first direction; and
- a stop mechanism that is operably couplable with the spool to prevent rotation of the spool in the second direction when a tension of the tension member is at or below a minimal tension threshold;
- wherein the stop mechanism is configured to contact the spool only when the tension of the tension member is at or below the minimal tension threshold.

2. The reel based closure device of claim 1, wherein the stop mechanism engages a bottom portion of the spool to prevent the spool from rotating in the second direction.

3. The reel based closure device of claim 2, wherein the spool is axially moveable within the interior region of the housing, and wherein axial movement of the spool within the interior region effects engagement and disengagement of the spool with the stop mechanism.

4. The reel based closure device of claim 1, wherein the stop mechanism is disengagable from the spool to allow the spool to rotate in the second direction.

5. The reel based closure device of claim 1, wherein the stop mechanism comprises one or more of the following:
- teeth;
- a rubber gasket;
- an abrasive material; or
- a tacky material.

6. The reel based closure device of claim 5, wherein the stop mechanism is arranged within the reel based closure device to engage a bottom surface of the spool.

7. The reel based closure device of claim 1, wherein the stop mechanism is disengaged from the spool until the tension of the tension member is at or below the minimal tension threshold, and wherein disengagement of the stop mechanism and spool allows the spool to rotate in the first direction and second direction.

8. The reel based closure device of claim 1, wherein the stop mechanism is separated from the spool by a gap when the stop mechanism and spool are disengaged.

9. A reel based closure device comprising:
- a housing;
- a spool positioned within the housing, the spool being rotatable in a first direction to wind a tension member about the spool;
- a tensioner that is operably coupled with the spool, the tensioner being configured to cause the spool to rotate in the first direction;
- a pawl that includes at least one pawl tooth that is configured to prevent rotation of the spool in a second direction; and
- a stop mechanism that is operable with the spool when a tension of the tension member is at or below a minimal tension threshold to prevent rotation of the spool in the second direction;
- wherein the stop mechanism is configured to contact the spool only when the tension of the tension member is at or below the minimal tension threshold.

10. The reel based closure device of claim 9, wherein the stop mechanism engages a bottom portion of the spool to prevent the spool from rotating in the second direction.

11. The reel based closure device of claim 10, wherein the spool is axially moveable within the housing, and wherein axial movement of the spool within the housing effects engagement and disengagement of the spool with the stop mechanism.

12. The reel based closure device of claim 10, wherein the stop mechanism is disengagable from the spool to allow the spool to rotate in the second direction.

13. The reel based closure device of claim 9, wherein the stop mechanism is disengagable from the spool until the tension of the tension member is at or below the minimal tension threshold, and wherein disengagement of the stop mechanism and spool allows the spool to rotate in the first direction and second direction.

14. The reel based closure device of claim 9, wherein the stop mechanism is separated from the spool by a gap when the stop mechanism and spool are disengaged.

15. A reel based closure device comprising:

a housing;

a spool positioned within the housing, the spool being rotatable in a first direction to wind a tension member about the spool;

a tensioner that is operably coupled with the spool, the tensioner being configured to cause the spool to rotate in the first direction;

a pawl component that includes at least one pawl that is configured to prevent rotation of the spool in a second direction that is opposite the first direction; and a stop mechanism that is operably coupled with the spool to prevent rotation of the spool in the second direction when a tension of the tension member is at or below a minimal tension threshold;

wherein the stop mechanism contacts the spool only when the tension of the tension member is at or below the minimal tension threshold.

16. The reel based closure device of claim 15, wherein the stop mechanism engages a bottom portion of the spool to prevent the spool from rotating in the second direction.

17. The reel based closure device of claim 16, wherein the spool is axially moveable within the housing, and wherein axial movement of the spool within the housing effects engagement and disengagement of the spool with the stop mechanism.

18. The reel based closure device of claim 16, wherein the stop mechanism is disengagable from the spool to allow the spool to rotate in the second direction.

19. The reel based closure device of claim 15, wherein the stop mechanism comprises one or more of the following:

teeth;

a rubber gasket;

an abrasive material; or a tacky material.

20. The reel based closure device of claim 15, wherein the stop mechanism is separated from the spool by a gap when the stop mechanism and spool are disengaged.

* * * * *